US006136310A

United States Patent [19]
Hanna et al.

[11] Patent Number: 6,136,310
[45] Date of Patent: *Oct. 24, 2000

[54] RECOMBINANT ANTI-CD4 ANTIBODIES FOR HUMAN THERAPY

[75] Inventors: Nabil Hanna, Olivenhain; Roland Anthony Newman; Mitchell Elliot Reff, both of San Diego, all of Calif.

[73] Assignee: IDEC Pharmaceuticals Corporation, San Diego, Calif.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/523,894

[22] Filed: Sep. 6, 1995

Related U.S. Application Data

[63] Continuation-in-part of application No. 08/476,237, Jun. 7, 1995, Pat. No. 5,756,096, which is a continuation-in-part of application No. 08/379,072, Jan. 25, 1995, Pat. No. 5,658,570, which is a continuation of application No. 07/912,292, Jul. 10, 1992, abandoned, which is a continuation-in-part of application No. 07/856,281, Mar. 23, 1992, abandoned, which is a continuation-in-part of application No. 07/735,064, Jul. 25, 1991, abandoned.

[51] Int. Cl.[7] .......................... A61K 39/395; C12P 21/08

[52] U.S. Cl. .................................... 424/154.1; 530/387.3; 424/133.1; 424/141.1

[58] Field of Search ...................... 530/387.3; 424/133.1, 424/141.1, 154.1

[56] References Cited

U.S. PATENT DOCUMENTS

| 4,816,397 | 3/1989 | Boss et al. ................................ 435/68 |
| 4,816,567 | 3/1989 | Cabilly et al. ........................... 530/387 |
| 4,973,745 | 11/1990 | Schoemaker et al. .................. 530/387 |
| 4,975,369 | 12/1990 | Beavers et al. ............................ 435/69 |

FOREIGN PATENT DOCUMENTS

| 0 451 216 B1 | 10/1991 | European Pat. Off. . |
| 0451216 B1 | 10/1991 | European Pat. Off. . |
| 0 523 949 A1 | 1/1993 | European Pat. Off. . |
| 0682040 A1 | 11/1995 | European Pat. Off. . |
| 9008198 | 7/1990 | WIPO . |

OTHER PUBLICATIONS

Proceedings of the National Academy of Sciences USA, vol. 88, No. 1, issued Jan. 1, 1991, Watanabe et al., "Soluble human CD4 elicts an antibody response in rhesus monkeys that inhibit simian immunodeficiency virus replication", pp. 120–124, see abstract, Issued Jan. 1988.
Surg. Gynecol. Obster., vol. 166, No. 1, Delmonico et al., "Monoclonal antibody treatment of human allograft recipients", pp. 89–98, see Abstract.
Infection and Immunity, vol. 61, No. 10, issued Oct. 1993, Lopez–Guerro et al., "Modulation of adjuvant arthritis in Lewis rats by recombinant vaccinia virus expressing the human 60–kilodalton heat shock protein", pp. 4225–4231, see entire document.
Dev. Comp. Immunol. vol. 17, No. 6, issued Nov.–Dec. 1993, Lewis et al. "Cloning and sequence analysis of kappa and gamma cynomolgus monkey immunoglobulin cDNAs", pp. 549–560.
Biotechnology, vol. 10, No. 11, issued Nov. 1992, Newman et al, "Primatization" of recombinant antibodies for immunotherapy of human diseases: a macaque/human chimeric antibody against CD4, pp. 1455–1460.
Jones, P.T. et al., Nature, 321:522, (1986).
Camerini, D. and Seed, B., Cell, 60:747, (1990).
McClure, M.O. et al., Nature 330:487, (1987).
Truneh, A. et al., Cell. Immun., 131:98, (1990).
Nishimura, Y. et al., Cancer Research, 47:999 (1987).
Ward, E.S. et al., Nature, 341:544 (1989).
Camerini, D. and Seed, B., Abstract No. T.C.P. 125, V International Conference on AIDS, p. 587, (1989).
Persson et al., Proc. Natl. Acad. Sci. USA, 88:2432, 1991.
Meek et al., J. Immun., 146:2434, 1991.
Allison et al., J. Immunological Methods, 95:157, 1986.
Ehrlich et al., Hybridoma, vol. 7, No. 4, pp. 385–395, 1988.
Ehrlich et al., Clin. Chem., 34:1681, 1988.
Van Meel et al., J. Immunological Methods, 80:267, 1985.
Ehrlich et al., Hum. Antibod. Hybridomas, 1990, vol. 1, No. 1.
Ehrlich et al., Hybridoma, vol. 6, No. 2, pp. 151–160, 1987.
Amoroso et al., J. Immun., 145:3155, 1990.
Huse et al., Science, 246:1275, 1989.
Letvin, et al., Effect of Recombinant Soluble CD4 in Rhesus Monkeys Infected With Simian Immunodeficiency Virus of Macaques, Abstract from the V Int. Conf. on AIDS, 1989, p. 535.
Rosenberg, M. et al., *Biotherapy*, "Soluble recombinant CD4—A potential therapeutic agent for HIV infector", 2:107, (1990).
Riechmann, L. et al., *Nature*, "Reshaping human antibodies for therapy", 332:323–327, (1988).
Houghton, A.N. et al., *Seminars in Oncology*, "Monoclonal antibodies potential applications to the treatment of cancer", 13:165, (1986).

(List continued on next page.)

*Primary Examiner*—Geetha P. Bansal
*Attorney, Agent, or Firm*—Burns, Doane, Swecker & Mathis, LLP

[57] ABSTRACT

Chimeric antibodies specific to human CD4 antigen, DNA encoding, pharmaceutical compositions containing and use thereof as therapeutic agents are taught. These chimeric antibodies contain Old World monkey variable sequences and human constant domain sequences, preferably human gamma 1, gamma 4 or mutated forms thereof. These antibodies possess desirable therapeutic properties including low antigenicity, reduced (or absent) T cell depleting activity, good affinity to human CD4 and enhanced stability (in vivo half-life).

16 Claims, 32 Drawing Sheets

OTHER PUBLICATIONS

Watanabe, M. et al., Proceedings of the National Academy of Sciences, 88:4616–4620, (1991).

Van Meurz et al. Journal of Immunological Methods (1986) 123.

Morrison Science, vol. 229, 1202 (1985).

Immunology Today 10:253 (1989).

Queen et al., PNAS 8610029 (1989).

Waldmann Science, vol. 252, 1657, (1991).

Hied et al., Genes and cancer (1990) p. 183.

VOPR Virusol, vol. 30, No. 5, issued Oct. 1985, Markova et al., "Monkey B lymphocyte subpopulations transformed by baboon herpes virus in vivo and in tissue cultures", pp. 549–553.

Harris et al., T.B. Tech., vol. 11, p. 42 (1993).

Truneh et al., "Humoral Response of Cynomolgus Macaques to Human Soluble CD4: Antibody Reactivity Restricted to Xeno–Human Determinants" Cellular Immunology, Nov. 1990, vol. 131, No. 1, pp. 98–108.

Van Meurs et al. "Production of Primate Monoclonal Antibodies" Journal of Immunological Methods, 1986, vol. 95, pp. 123–128.

Schroeder et al. "Early Restriction of the Human Antibody Repertoire" Science, Nov. 6, 1987, vol. 238, pp. 791–793.

Combriato et al. "V Lambda and J Lambda–C Lambda Gene Segments of the Human Immunoglobulin Lambda Light Chain Locus are Separated by 14 KB and Rearrange by a Deletion Mechanism" European Journal of Immunology, Jun. 1991, vol. 21, pp. 1513–1522.

Hughes–Jones et al. "Nucleotide Sequences and Three–Dimensional Modelling of the VH and VL Domains of Two Human Monoclonal Antibodies Specific for the D Antigen of the Human RH–Blood Group System" The Biochemical Journal, May 15, 1990, vol. 268, No. 1, pp. 135–140.

Stephens et al., "Antibodies are Produced to the Variable Regions of the External Envelope Glycoprotein of Human Immunodeficiency Virus Type 1 in Chimpanzees Infected with the Virus and Baboons Immunized with a Candidate Recombinant Vaccine" The Journal of General Virology, May 1992, vol. 73, No. 5, pp. 1099–1106.

Figure 1

```
         M   K   H   L   W   F   F   L   L   L   V   A   A   P   R
       GAC ATG AAA CAC CTG TGG TTC TTC CTC CTC CTG GTG GCA GCC CCC AGA

+1                                      10
         W   V   L   S   Q   V   Q   L   Q   E   A   G   P   G   L   V
       TGG GTC TTG TCC CAG GTG CAG CTG CAG GAG GCG GGC CCA GGA CTG GTG

20
         K   P   S   E   T   L   S   L   T   C   S   V   S   G   G   S
       AAG CCT TCG GAG ACC CTG TCC CTC ACC TGC AGT GTC TCT GGT GGC TCC 30                                      40
         I   S   G   D   Y   Y   W   F   W   I   R   Q   S   P   G   K
       ATC AGC GGT GAC TAT TAT TGG TTC TGG ATC CGC CAG TCC CCA GGG AAG 50                                      60
         G   L   E   W   I   G   Y   I   Y   G   S   G   G   T   N
       GGA CTG GAG TGG ATC GGC TAC ATC TAT GGC AGT GGT GGG GGC ACC AAT

70
         Y   N   P   S   L   N   N   R   V   S   I   S   I   D   T   S
       TAC AAT CCC TCC CTC AAC AAT CGA GTC TCC ATT TCA ATA GAC ACG TCC 80                                      90
         K   N   L   F   S   L   K   L   R   S   V   T   A   A   D   T
       AAG AAC CTC TTC TCC CTG AAA CTG AGG TCT GTG ACC GCC GCG GAC ACG

100
         A   V   Y   Y   C   A   S   N   I   L   K   Y   L   H   W   L
       GCC GTC TAT TAC TGT GCG AGT AAT ATA TTG AAA TAT CTT CAC TGG TTA 110                                     120
         L   Y   W   G   Q   G   V   L   V   T   S   S
       TTA TAC TGG GGC CAG GGA GTC CTG GTC ACC GTC TCC
```

Figure 2

```
        M   A   W   A   L   L   L   L   G   L   L   A   H   F   T
ACC ATG GCC TGG GCT CTG CTG CTC CTC GGC CTC CTT GCT CAC TTT ACA

+1                                          10
    D   S   A   A   S   Y   E   L   S   Q   P   R   S   V   S   V
GAC TCT GCG GCC TCC TAT GAG TTG AGT CAG CCT CGC TCA GTG TCC GTG

20
    S   P   G   Q   T   A   G   F   T   C   G   G   D   N   V   G
TCC CCA GGA CAG ACG GCC GGG TTC ACC TGT GGG GGA GAC AAC GTT GGA 30                                      40
    R   K   S   V   Q   W   Y   Q   Q   K   P   P   Q   A   P   V
AGG AAA AGT GTA CAG TGG TAC CAG CAG AAG CCA CCG CAG GCC CCT GTG 50                                          60
    L   V   I   Y   A   D   S   E   R   P   S   G   I   P   A   R
CTG GTC ATC TAT GCT GAC AGC GAA CGG CCC TCA GGG ATC CCT GCG CGA

70
    F   S   G   S   N   S   G   N   T   A   T   L   T   I   S   G
TTC TCT GGC TCC AAC TCA GGG AAC ACC GCC ACC CTG ACC ATC AGC GGG 80                                          90
    V   E   A   G   D   E   A   D   Y   Y   C   Q   V   W   D   S
GTC GAG GCC GGG GAT GAG GCT GAC TAT TAC TGT CAG GTG TGG GAC AGT

100
    T   A   D   H   W   V   F   G   G   G   T   R   L   T   V   L
ACT GCT GAT CAT TGG GTC TTC GGC GGA GGG ACC CGG CTG ACC GTC CTA

109
 G
GGT
```

Figure 3

```
Frame 1  Met Ala Trp Ala Leu Leu Leu Leu Gly Leu Leu Ala His Phe Thr Asp Ser Ala Ala
         ATG GCC TGG GCT CTG CTG CTC CTC GGC CTC CTT GCT CAC TTT ACA GAC TCT GCG GCC
                     9           18          27          36          45          54

Ser Tyr Glu Leu Ser Gln Pro Arg Ser Val Ser Val Ser Pro Gly Gln Thr Ala Gly Phe Thr
TCC TAT GAG TTG AGT CAG CCT CGC TCA GTG TCC GTG TCC CCA GGA CAG ACG GCC GGG TTC ACC
        66          75          84          93         102         111         120

Cys Gly Gly Asp Asn Val Gly Arg Lys Ser Val Gln Trp Tyr Gln Gln Lys Pro Pro Gln Ala
TGT GGG GGA GAC AAC GTT GGA AGG AAA AGT GTA CAG TGG TAC CAG CAG AAG CCA CCG CAG GCC
       129         138         147         156         165         174         183

Pro Val Leu Val Ile Tyr Ala Asp Ser Glu Arg Pro Ser Gly Ile Pro Ala Arg Phe Ser Gly
CCT GTG CTG GTC ATC TAT GCT GAC AGC GAA CGG CCC TCA GGG ATC CCT GCG CGA TTC TCT GGC
       192         201         210         219         228         237         246

Ser Asn Ser Gly Asn Thr Ala Thr Leu Thr Ile Ser Gly Val Glu Ala Gly Asp Glu Ala Asp
TCC AAC TCA GGG AAC ACC GCC ACC CTG ACC ATC AGC GGG GTC GAG GCC GGG GAT GAG GCT GAC
       255         264         273         282         291         300         309

Tyr Tyr Cys Gln Val Trp Asp Ser Thr Ala Asp His Trp Val Phe Gly Gly Gly Thr Arg Leu
TAT TAC TGT CAG GTG TGG GAC AGT ACT GCT GAT CAT TGG GTC TTC GGC GGA GGG ACC CGG CTG
       318         327         336         345         354         363         372

Thr Val Leu Gly Gln Pro Lys Ala Ala Pro Ser Val Thr Leu Phe Pro Pro Ser Ser Glu Glu
ACC GTC CTA GGT CAG CCC AAG GCT GCC CCC TCG GTC ACT CTG TTC CCG CCC TCC TCT GAG GAG
       381         390         399         408         417         426         435

Leu Gln Ala Asn Lys Ala Thr Leu Val Cys Leu Ile Ser Asp Phe Tyr Pro Gly Ala Val Thr
CTT CAA GCC AAC AAG GCC ACA CTG GTG TGT CTC ATA AGT GAC TTC TAC CCG GGA GCC GTG ACA
       444         453         462         471         480         489         498

Val Ala Trp Lys Ala Asp Ser Ser Pro Val Lys Ala Gly Val Glu Thr Thr Thr Pro Ser Lys
GTG GCC TGG AAG GCA GAT AGC AGC CCC GTC AAG GCG GGA GTG GAG ACC ACC ACA CCC TCC AAA
       507         516         525         534         543         552         561

Gln Ser Asn Asn Lys Tyr Ala Ala Ser Ser Tyr Leu Ser Leu Thr Pro Glu Gln Trp Lys Ser
CAA AGC AAC AAC AAG TAC GCG GCC AGC AGC TAC CTG AGC CTG ACG CCT GAG CAG TGG AAG TCC
       570         579         588         597         606         615         624

His Arg Ser Tyr Ser Cys Gln Val Thr His Glu Gly Ser Thr Val Glu Lys Thr Val Ala Pro
CAC AGA AGC TAC AGC TGC CAG GTC ACG CAT GAA GGG AGC ACC GTG GAG AAG ACA GTG GCC CCT
       633         642         651         660         669         678         687

Thr Glu Cys Ser TER
ACA GAA TGT TCA TGA
```

Figure 4

```
Frame 1  Met Lys His Leu Trp Phe Phe Leu Leu Leu Val Ala Ala Pro Arg Trp Val Leu Ser
         ATG AAA CAC CTG TGG TTC TTC CTC CTC CTG GTG GCA GCC CCC AGA TGG GTC TTG TCC
                       9          18          27          36          45          54

Gln Val Gln Leu Gln Glu Ser Gly Pro Gly Leu Val Lys Pro Ser Glu Thr Leu Ser Leu Thr
         CAG GTG CAG CTG CAG GAG TCG GGC CCA GGA CTG GTG AAG CCT TCG GAG ACC CTG TCC CTC ACC
                  66          75          84          93         102         111         120

Cys Ser Val Ser Gly Gly Ser Ile Ser Gly Asp Tyr Tyr Trp Phe Trp Ile Arg Gln Ser Pro
         TGC AGT GTC TCT GGT GGC TCC ATC AGC GGT GAC TAT TAT TGG TTC TGG ATC CGC CAG TCC CCA
                 129         138         147         156         165         174         183

Gly Lys Gly Leu Glu Trp Ile Gly Tyr Ile Tyr Gly Ser Gly Gly Gly Thr Asn Tyr Asn Pro
         GGG AAG GGA CTG GAG TGG ATC GGC TAC ATC TAT GGC AGT GGT GGG GGC ACC AAT TAC AAT CCC
                 192         201         210         219         228         237         246

Ser Leu Asn Asn Arg Val Ser Ile Ser Ile Asp Thr Ser Lys Asn Leu Phe Ser Leu Lys Leu
         TCC CTC AAC AAT CGA GTC TCC ATT TCA ATA GAC ACG TCC AAG AAC CTC TTC TCC CTG AAA CTG
                 255         264         273         282         291         300         309

Arg Ser Val Thr Ala Ala Asp Thr Ala Val Tyr Tyr Cys Ala Ser Asn Ile Leu Lys Tyr Leu
         AGG TCT GTG ACC GCC GCG GAC ACG GCC GTC TAT TAC TGT GCG AGT AAT ATA TTG AAA TAT CTT
                 318         327         336         345         354         363         372

His Trp Leu Leu Tyr Trp Gly Gln Gly Val Leu Val Thr Val Ser Ser Ala Ser Thr Lys Gly
         CAC TGG TTA TTA TAC TGG GGC CAG GGA GTC CTG GTC ACC GTC TCC TCA GCT AGC ACC AAG GGC
                 381         390         399         408         417         426         435

Pro Ser Val Phe Pro Leu Ala Pro Cys Ser Arg Ser Thr Ser Glu Ser Thr Ala Ala Leu Gly
         CCA TCC GTC TTC CCC CTG GCG CCC TGC TCC AGG AGC ACC TCC GAG AGC ACA GCC GCC CTG GGC
                 444         453         462         471         480         489         498

Cys Leu Val Lys Asp Tyr Phe Pro Glu Pro Val Thr Val Ser Trp Asn Ser Gly Ala Leu Thr
         TGC CTG GTC AAG GAC TAC TTC CCC GAA CCG GTG ACG GTG TCG TGG AAC TCA GGC GCC CTG ACC
                 507         516         525         534         543         552         561

Ser Gly Val His Thr Phe Pro Ala Val Leu Gln Ser Ser Gly Leu Tyr Ser Leu Ser Ser Val
         AGC GGC GTG CAC ACC TTC CCG GCT GTC CTA CAG TCC TCA GGA CTC TAC TCC CTC AGC AGC GTG
                 570         579         588         597         606         615         624

Val Thr Val Pro Ser Ser Ser Leu Gly Thr Lys Thr Tyr Thr Cys Asn Val Asp His Lys Pro
         GTG ACC GTG CCC TCC AGC AGC TTG GGC ACG AAG ACC TAC ACC TGC AAC GTA GAT CAC AAG CCC
                 633         642         651         660         669         678         687

Ser Asn Thr Lys Val Asp Lys Arg Val Glu Ser Lys Tyr Gly Pro Pro Cys Pro Ser Cys Pro
```

Figure 4 (Continued)

```
        AGC AAC ACC AAG GTG GAC AAG AGA GTT GAG TCC AAA TAT GGT CCC CCA TGC CCA TCA TGC CCA
            696         705         714         723         732         741         750

Ala Pro Glu Phe Leu Gly Gly Pro Ser Val Phe Leu Phe Pro Pro Lys Pro Lys Asp Thr Leu
GCA CCT GAG TTC CTG GGG GGA CCA TCA GTC TTC CTG TTC CCC CCA AAA CCC AAG GAC ACT CTC
    759         768         777         786         795         804         813

Met Ile Ser Arg Thr Pro Glu Val Thr Cys Val Val Val Asp Val Ser Gln Glu Asp Pro Glu
ATG ATC TCC CGG ACC CCT GAG GTC ACG TGC GTG GTG GTG GAC GTG AGC CAG GAA GAC CCC GAG
    822         831         840         849         858         867         876

Val Gln Phe Asn Trp Tyr Val Asp Gly Val Glu Val His Asn Ala Lys Thr Lys Pro Arg Glu
GTC CAG TTC AAC TGG TAC GTG GAT GGC GTG GAG GTG CAT AAT GCC AAG ACA AAG CCG CGG GAG
    885         894         903         912         921         930         939

Glu Gln Phe Asn Ser Thr Tyr Arg Val Val Ser Val Leu Thr Val Leu His Gln Asp Trp Leu
GAG CAG TTC AAC AGC ACG TAC CGT GTG GTC AGC GTC CTC ACC GTC CTG CAC CAG GAC TGG CTG
    948         957         966         975         984         993        1002

Asn Gly Lys Glu Tyr Lys Cys Lys Val Ser Asn Lys Gly Leu Pro Ser Ser Ile Glu Lys Thr
AAC GGC AAG GAG TAC AAG TGC AAG GTC TCC AAC AAA GGC CTC CCG TCC TCC ATC GAG AAA ACC
   1011        1020        1029        1038        1047        1056        1065

Ile Ser Lys Ala Lys Gly Gln Pro Arg Glu Pro Gln Val Tyr Thr Leu Pro Pro Ser Gln Glu
ATC TCC AAA GCC AAA GGG CAG CCC CGA GAG CCA CAG GTG TAC ACC CTG CCC CCA TCC CAG GAG
   1074        1083        1092        1101        1110        1119        1128

Glu Met Thr Lys Asn Gln Val Ser Leu Thr Cys Leu Val Lys Gly Phe Tyr Pro Ser Asp Ile
GAG ATG ACC AAG AAC CAG GTC AGC CTG ACC TGC CTG GTC AAA GGC TTC TAC CCC AGC GAC ATC
   1137        1146        1155        1164        1173        1182        1191

Ala Val Glu Trp Glu Ser Asn Gly Gln Pro Glu Asn Asn Tyr Lys Thr Thr Pro Pro Val Leu
GCC GTG GAG TGG GAG AGC AAT GGG CAG CCG GAG AAC AAC TAC AAG ACC ACG CCT CCC GTG CTG
   1200        1209        1218        1227        1236        1245        1254

Asp Ser Asp Gly Ser Phe Phe Leu Tyr Ser Arg Leu Thr Val Asp Lys Ser Arg Trp Gln Glu
GAC TCC GAC GGC TCC TTC TTC CTC TAC AGC AGG CTA ACC GTG GAC AAG AGC AGG TGG CAG GAG
   1263        1272        1281        1290        1299        1308        1317

Gly Asn Val Phe Ser Cys Ser Val Met His Glu Ala Leu His Asn His Tyr Thr Gln Lys Ser
GGG AAT GTC TTC TCA TGC TCC GTG ATG CAT GAG GCT CTG CAC AAC CAC TAC ACA CAG AAG AGC
   1326        1335        1344        1353        1362        1371        1380

Leu Ser Leu Ser Leu Gly Lys TER
CTC TCC CTG TCT CTG GGT AAA TGA
   1389        1398
```

Figure 5

```
Frame 1  Met Lys His Leu Trp Phe Phe Leu Leu Leu Val Ala Ala Pro Arg Trp Val Leu Ser
         ATG AAA CAC CTG TGG TTC TTC CTC CTC CTG GTG GCA GCC CCC AGA TGG GTC TTG TCC
                   9           18          27          36          45          54

Gln Val Gln Leu Gln Glu Ser Gly Pro Gly Leu Val Lys Pro Ser Glu Thr Leu Ser Leu Thr
         CAG GTG CAG CTG CAG GAG TCG GGC CCA GGA CTG GTG AAG CCT TCG GAG ACC CTG TCC CTC ACC
                   66          75          84          93         102         111         120

Cys Ser Val Ser Gly Gly Ser Ile Ser Gly Asp Tyr Tyr Trp Phe Trp Ile Arg Gln Ser Pro
         TGC AGT GTC TCT GGT GGC TCC ATC AGC GGT GAC TAT TAT TGG TTC TGG ATC CGC CAG TCC CCA
                  129         138         147         156         165         174         183

Gly Lys Gly Leu Glu Trp Ile Gly Tyr Ile Tyr Gly Ser Gly Gly Gly Thr Asn Tyr Asn Pro
         GGG AAG GGA CTG GAG TGG ATC GGC TAC ATC TAT GGC AGT GGT GGG GGC ACC AAT TAC AAT CCC
                  192         201         210         219         228         237         246

Ser Leu Asn Asn Arg Val Ser Ile Ser Ile Asp Thr Ser Lys Asn Leu Phe Ser Leu Lys Leu
         TCC CTC AAC AAT CGA GTC TCC ATT TCA ATA GAC ACG TCC AAG AAC CTC TTC TCC CTG AAA CTG
                  255         264         273         282         291         300         309

Arg Ser Val Thr Ala Ala Asp Thr Ala Val Tyr Tyr Cys Ala Ser Asn Ile Leu Lys Tyr Leu
         AGG TCT GTG ACC GCC GCG GAC ACG GCC GTC TAT TAC TGT GCG AGT AAT ATA TTG AAA TAT CTT
                  318         327         336         345         354         363         372

His Trp Leu Leu Tyr Trp Gly Gln Gly Val Leu Val Thr Val Ser Ser Ala Ser Thr Lys Gly
         CAC TGG TTA TTA TAC TGG GGC CAG GGA GTC CTG GTC ACC GTC TCA GCT AGC ACC AAG GGG
                  381         390         399         408         417         426         435

Pro Ser Val Phe Pro Leu Ala Pro Cys Ser Arg Ser Thr Ser Glu Ser Thr Ala Ala Leu Gly
         CCA TCC GTC TTC CCC CTG GCG CCC TGC TCC AGG AGC ACC TCC GAG AGC ACA GCC GCC CTG GGC
                  444         453         462         471         480         489         498

Cys Leu Val Lys Asp Tyr Phe Pro Glu Pro Val Thr Val Ser Trp Asn Ser Gly Ala Leu Thr
         TGC CTG GTC AAG GAC TAC TTC CCC GAA CCG GTG ACG GTG TCG TGG AAC TCA GGC GCC CTG ACC
                  507         516         525         534         543         552         561

Ser Gly Val His Thr Phe Pro Ala Val Leu Gln Ser Ser Gly Leu Tyr Ser Leu Ser Ser Val
         AGC GGC GTG CAC ACC TTC CCG GCT GTC CTA CAG TCC TCA GGA CTC TAC TCC CTC AGC AGC GTG
                  570         579         588         597         606         615         624

Val Thr Val Pro Ser Ser Ser Leu Gly Thr Lys Thr Tyr Thr Cys Asn Val Asp His Lys Pro
         GTG ACC GTG CCC TCC AGC AGC TTG GGC ACG AAG ACC TAC ACC TGC AAC GTA GAT CAC AAG CCC
                  633         642         651         660         669         678         687

Ser Asn Thr Lys Val Asp Lys Arg Val Glu Ser Lys Tyr Gly Pro Pro Cys Pro Ser Cys Pro
```

Figure 5 (Continued)

```
Ser Asn Thr Lys Val Asp Lys Arg Val Glu Ser Lys Tyr Gly Pro Pro Cys Pro Ser Cys Pro
AGC AAC ACC AAG GTG GAC AAG AGA GTT GAG TCC AAA TAT GGT CCC CCA TGC CCA TCA TGC CCA
        696         705         714         723         732         741         750

Ala Pro Glu Phe Glu Gly Gly Pro Ser Val Phe Leu Phe Pro Pro Lys Pro Lys Asp Thr Leu
GCA CCT GAG TTC GAG GGG GGA CCA TCA GTC TTC CTG TTC CCC CCA AAA CCC AAG GAC ACT CTC
        759         768         777         786         795         804         813

Met Ile Ser Arg Thr Pro Glu Val Thr Cys Val Val Val Asp Val Ser Gln Glu Asp Pro Glu
ATG ATC TCC CGG ACC CCT GAG GTC ACG TGC GTG GTG GTG GAC GTG AGC CAG GAA GAC CCC GAG
        822         831         840         849         858         867         876

Val Gln Phe Asn Trp Tyr Val Asp Gly Val Glu Val His Asn Ala Lys Thr Lys Pro Arg Glu
GTC CAG TTC AAC TGG TAC GTG GAT GGC GTG GAG GTG CAT AAT GCC AAG ACA AAG CCG CGG GAG
        885         894         903         912         921         930         939

Glu Gln Phe Asn Ser Thr Tyr Arg Val Val Ser Val Leu Thr Val Leu His Gln Asp Trp Leu
GAG CAG TTC AAC AGC ACG TAC CGT GTG GTC AGC GTC CTC ACC GTC CTG CAC CAG GAC TGG CTG
        948         957         966         975         984         993        1002

Asn Gly Lys Glu Tyr Lys Cys Lys Val Ser Asn Lys Gly Leu Pro Ser Ser Ile Glu Lys Thr
AAC GGC AAG GAG TAC AAG TGC AAG GTC TCC AAC AAA GGC CTC CCG TCC TCC ATC GAG AAA ACC
       1011        1020        1029        1038        1047        1056        1065

Ile Ser Lys Ala Lys Gly Gln Pro Arg Glu Pro Gln Val Tyr Thr Leu Pro Pro Ser Gln Glu
ATC TCC AAA GCC AAA GGG CAG CCC CGA GAG CCA CAG GTG TAC ACC CTG CCC CCA TCC CAG GAG
       1074        1083        1092        1101        1110        1119        1128

Glu Met Thr Lys Asn Gln Val Ser Leu Thr Cys Leu Val Lys Gly Phe Tyr Pro Ser Asp Ile
GAG ATG ACC AAG AAC CAG GTC AGC CTG ACC TGC CTG GTC AAA GGC TTC TAC CCC AGC GAC ATC
       1137        1146        1155        1164        1173        1182        1191

Ala Val Glu Trp Glu Ser Asn Gly Gln Pro Glu Asn Asn Tyr Lys Thr Thr Pro Pro Val Leu
GCC GTG GAG TGG GAG AGC AAT GGG CAG CCG GAG AAC AAC TAC AAG ACC ACG CCT CCC GTG CTG
       1200        1209        1218        1227        1236        1245        1254

Asp Ser Asp Gly Ser Phe Phe Leu Tyr Ser Arg Leu Thr Val Asp Lys Ser Arg Trp Gln Glu
GAC TCC GAC GGC TCC TTC TTC CTC TAC AGC AGG CTA ACC GTG GAC AAG AGC AGG TGG CAG GAG
       1263        1272        1281        1290        1299        1308        1317

Gly Asn Val Phe Ser Cys Ser Val Met His Glu Ala Leu His Asn His Tyr Thr Gln Lys Ser
GGG AAT GTC TTC TCA TGC TCC GTG ATG CAT GAG GCT CTG CAC AAC CAC TAC ACA CAG AAG AGC
       1326        1335        1344        1353        1362        1371        1380

Leu Ser Leu Ser Leu Gly Lys TER
CTC TCC CTG TCT CTG GGT AAA TGA
       1389        1398
```

Figure 6

```
Frame 1  Met Lys His Leu Trp Phe Phe Leu Leu Leu Val Ala Ala Pro Arg Trp Val Leu Ser
         ATG AAA CAC CTG TGG TTC TTC CTC CTC CTG GTG GCA GCC CCC AGA TGG GTC TTG TCC
                   9          18          27          36          45          54

Gln Val Gln Leu Gln Glu Ser Gly Pro Gly Leu Val Lys Pro Ser Glu Thr Leu Ser Leu Thr
         CAG GTG CAG CTG CAG GAG TCG GGC CCA GGA CTG GTG AAG CCT TCG GAG ACC CTG TCC CTC ACC
                   66          75          84          93         102         111         120

Cys Ser Val Ser Gly Gly Ser Ile Ser Gly Asp Tyr Tyr Trp Phe Trp Ile Arg Gln Ser Pro
         TGC AGT GTC TCT GGT GGC TCC ATC AGC GGT GAC TAT TAT TGG TTC TGG ATC CGC CAG TCC CCA
                  129         138         147         156         165         174         183

Gly Lys Gly Leu Glu Trp Ile Gly Tyr Ile Tyr Gly Ser Gly Gly Gly Thr Asn Tyr Asn Pro
         GGG AAG GGA CTG GAG TGG ATC GGC TAC ATC TAT GGC AGT GGT GGG GGC ACC AAT TAC AAT CCC
                  192         201         210         219         228         237         246

Ser Leu Asn Asn Arg Val Ser Ile Ser Ile Asp Thr Ser Lys Asn Leu Phe Ser Leu Lys Leu
         TCC CTC AAC AAT CGA GTC TCC ATT TCA ATA GAC ACG TCC AAG AAC CTC TTC TCC CTG AAA CTG
                  255         264         273         282         291         300         309

Arg Ser Val Thr Ala Ala Asp Thr Ala Val Tyr Tyr Cys Ala Ser Asn Ile Leu Lys Tyr Leu
         AGG TCT GTG ACC GCC GCG GAC ACG GCC GTC TAT TAC TGT GCG AGT AAT ATA TTG AAA TAT CTT
                  318         327         336         345         354         363         372

His Trp Leu Leu Tyr Trp Gly Gln Gly Val Leu Val Thr Val Ser Ser Ala Ser Thr Lys Gly
         CAC TGG TTA TTA TAC TGG GGC CAG GGA GTC CTG GTC ACC GTC TCC TCA GCT AGC ACC AAG GGG
                  381         390         399         408         417         426         435

Pro Ser Val Phe Pro Leu Ala Pro Cys Ser Arg Ser Thr Ser Glu Ser Thr Ala Ala Leu Gly
         CCA TCC GTC TTC CCC CTG GCG CCC TGC TCC AGG AGC ACC TCC GAG AGC ACA GCC GCC CTG GGC
                  444         453         462         471         480         489         498

Cys Leu Val Lys Asp Tyr Phe Pro Glu Pro Val Thr Val Ser Trp Asn Ser Gly Ala Leu Thr
         TGC CTG GTC AAG GAC TAC TTC CCC GAA CCG GTG ACG GTG TCG TGG AAC TCA GGC GCC CTG ACC
                  507         516         525         534         543         552         561

Ser Gly Val His Thr Phe Pro Ala Val Leu Gln Ser Ser Gly Leu Tyr Ser Leu Ser Ser Val
         AGC GGC GTG CAC ACC TTC CCG GCT GTC CTA CAG TCC TCA GGA CTC TAC TCC CTC AGC AGC GTG
                  570         579         588         597         606         615         624

Val Thr Val Pro Ser Ser Ser Leu Gly Thr Lys Thr Tyr Thr Cys Asn Val Asp His Lys Pro
         GTG ACC GTG CCC TCC AGC AGC TTG GGC ACG AAG ACC TAC ACC TGC AAC GTA GAT CAC AAG CCC
                  633         642         651         660         669         678         687

Ser Asn Thr Lys Val Asp Lys Arg Val Glu Ser Lys Tyr Gly Pro Pro Cys Pro Pro Cys Pro
```

Figure 6 (Continued)

```
        Ser Asn Thr Lys Val Asp Lys Arg Val Glu Ser Lys Tyr Gly Pro Pro Cys Pro Pro Cys Pro
        AGC AAC ACC AAG GTG GAC AAG AGA GTT GAG TCC AAA TAT GGT CCC CCA TGC CCA CCA TGC CCA
                696         705         714         723         732         741         750

Ala Pro Glu Phe Glu Gly Gly Pro Ser Val Phe Leu Phe Pro Pro Lys Pro Lys Asp Thr Leu
GCA CCT GAG TTC GAG GGG GGA CCA TCA GTC TTC CTG TTC CCC CCA AAA CCC AAG GAC ACT CTC
        759         768         777         786         795         804         813

Met Ile Ser Arg Thr Pro Glu Val Thr Cys Val Val Val Asp Val Ser Gln Glu Asp Pro Glu
ATG ATC TCC CGG ACC CCT GAG GTC ACG TGC GTG GTG GTG GAC GTG AGC CAG GAA GAC CCC GAG
        822         831         840         849         858         867         876

Val Gln Phe Asn Trp Tyr Val Asp Gly Val Glu Val His Asn Ala Lys Thr Lys Pro Arg Glu
GTC CAG TTC AAC TGG TAC GTG GAT GGC GTG GAG GTG CAT AAT GCC AAG ACA AAG CCG CGG GAG
        885         894         903         912         921         930         939

Glu Gln Phe Asn Ser Thr Tyr Arg Val Val Ser Val Leu Thr Val Leu His Gln Asp Trp Leu
GAG CAG TTC AAC AGC ACG TAC CGT GTG GTC AGC GTC CTC ACC GTC CTG CAC CAG GAC TGG CTG
        948         957         966         975         984         993         1002

Asn Gly Lys Glu Tyr Lys Cys Lys Val Ser Asn Lys Gly Leu Pro Ser Ser Ile Glu Lys Thr
AAC GGC AAG GAG TAC AAG TGC AAG GTC TCC AAC AAA GGC CTC CCG TCC TCC ATC GAG AAA ACC
        1011        1020        1029        1038        1047        1056        1065

Ile Ser Lys Ala Lys Gly Gln Pro Arg Glu Pro Gln Val Tyr Thr Leu Pro Pro Ser Gln Glu
ATC TCC AAA GCC AAA GGG CAG CCC CGA GAG CCA CAG GTG TAC ACC CTG CCC CCA TCC CAG GAG
        1074        1083        1092        1101        1110        1119        1128

Glu Met Thr Lys Asn Gln Val Ser Leu Thr Cys Leu Val Lys Gly Phe Tyr Pro Ser Asp Ile
GAG ATG ACC AAG AAC CAG GTC AGC CTG ACC TGC CTG GTC AAA GGC TTC TAC CCC AGC GAC ATC
        1137        1146        1155        1164        1173        1182        1191

Ala Val Glu Trp Glu Ser Asn Gly Gln Pro Glu Asn Asn Tyr Lys Thr Thr Pro Pro Val Leu
GCC GTG GAG TGG GAG AGC AAT GGG CAG CCG GAG AAC AAC TAC AAG ACC ACG CCT CCC GTG CTG
        1200        1209        1218        1227        1236        1245        1254

Asp Ser Asp Gly Ser Phe Phe Leu Tyr Ser Arg Leu Thr Val Asp Lys Ser Arg Trp Gln Glu
GAC TCC GAC GGC TCC TTC TTC CTC TAC AGC AGG CTA ACC GTG GAC AAG AGC AGG TGG CAG GAG
        1263        1272        1281        1290        1299        1308        1317

Gly Asn Val Phe Ser Cys Ser Val Met His Glu Ala Leu His Asn His Tyr Thr Gln Lys Ser
GGG AAT GTC TTC TCA TGC TCC GTG ATG CAT GAG GCT CTG CAC AAC CAC TAC ACA CAG AAG AGC
        1326        1335        1344        1353        1362        1371        1380

Leu Ser Leu Ser Leu Gly Lys TER
CTC TCC CTG TCT CTG GGT AAA TGA
        1389        1398
```

Figure 7-1

Primers for the Amplifcation of Monkey Immunoglobulin Heavy Chain Variable Regions

5' 'Sense' Primers

**A. Human or Monkey heavy chain early leader sequence primers with *Sal I* site**

$V_H1$  5' ACTAA<u>GTCGAC</u>ATGGACTGGACCTGG 3'

$V_H2$  5' ACTAA<u>GTCGAC</u>ATGGACATACTTTGTTCCAC 3'

$V_H3$  5' ACTAA<u>GTCGAC</u>ATGGAGTTTGGGCTGAGC 3'

$V_H4$  5' ACTAA<u>GTCGAC</u>ATGAAACACCTGTGGTTCTT 3'

$V_H5$  5' ACTAA<u>GTCGAC</u>ATGGGGTCAACCGCCATCCT 3'

$V_H6$  5' ACTAA<u>GTCGAC</u>ATGTCTGTCTCCTTCCTCAT 3'

**B. Human or Monkey heavy chain late leader sequence primers with *Mlu I* site**

$V_H1$  5' G GCA GCA GC(CT) <u>ACG CGT</u> GCC CAC TCC GAG GT 3'  $^{+1}$ $V_H2$  5' G ACC GTC CCG <u>ACG CGT</u> GT(TC) TTG TCC CAG GT 3'  $^{+1}$ $V_H3$  5' GCT ATT TTC <u>ACG CGT</u> GTC CAG TGT GAG 3'  $^{+1}$ $V_H4$  5' GCG GCT CCC <u>ACG CGT</u> GTC CTG TCC CAG 3'  $^{+1}$ $V_H5$  5' G GCT GTT CTC <u>ACG CGT</u> GTC TGT GCC GAG GT 3'  $^{+1}$

Figure 7-1 cont.

C. Human or Monkey framework 1 sequence primers with *Xho I* site $V_H1,3a,5$   CAGGTGCAGCTG<u>CTCGAG</u>TCTGG $V_H2$      CAGGTCAACTTA<u>CTCGAG</u>TCTGG $V_H3b$     GAGGTGCAGCTG<u>CTCGAG</u>TCTGG $V_H4$      CAGGTGCAGCTG<u>CTCGAG</u>TCGGG $V_H6$      CAGGTACAGCTG<u>CTCGAG</u>TCAGG (each sequence marked with +1)

3' 'Anti-Sense' Primers.

A. Human or Monkey Heavy Chain Constant Region Primers Anti-Sense Strand with *Nhe 1* site

+118                    +110

$IgG_{1-4}$   5' GGC GGA TGC <u>GCT AGC</u> TGA GGA GAC GG 3'

Nhe 1

Figure 7-2

Primers for the Amplification of Monkey Immunoglobulin Light Chain Variable Regions

5' 'Sense' Primers

A. Human or Monkey kappa light chain early leader primers with Bgl II site

1. 5' ATCAC<u>AGATCT</u>CTCACCATGGTGTTGCAGACCCAGGTC 3'

2. 5' ATCAC<u>AGATCT</u>CTCACCATGG(GA)G(AT)CCCC(TA)GC(TG)CAGCT 3'

3. 5' ATCAC<u>AGATCT</u>CTCACCATGGACATGAGGGTCCCCGCTCAG 3'

4. 5' ATCAC<u>AGATCT</u>CTCACCATGGACAC(GAC)AGGGCCCCACTCAG 3'

B. Human or Monkey lambda light chain early leader primers with Bgl II site

1. 5' ATCAC<u>AGATCT</u>CTCACCATGGCCTGGGCTCTGCTGCTCC 3'

2. 5' ATCAC<u>AGATCT</u>CTCACCATGGCCTGGGCTCCACTACTTC 3'

3. 5' ATCAC<u>AGATCT</u>CTCACCATGACCTGCTCCCCTCTCCTCC 3'

4. 5' ATCAC<u>AGATCT</u>CTCACCATGGCCTGGACTCCTCTCTTTC 3'

5. 5' ATCAC<u>AGATCT</u>CTCACCATGACTTGGACCCCACTCCTC 3'

Figure 7-2 cont.

3' 'Anti-Sense' Primers

A. <u>Human or Monkey kappa light chain constant region primer anti-sense strand with Kpn 1 and BsiW1 sites</u>

$C_{kappa}$
          +108                                                +97
5' CCG TTT GAT TTC CAG CTT <u>GGT ACC</u> TCC ACC GAA CGT 3'
                                      Kpn 1

+112                                +103
5' TGC AGC ATC <u>CGT ACG</u> TTT GAT TTC CAG CTT 3'
                    BsiW1

B. <u>Human or Monkey lambda light chain constant region primer anti-sense strand with Kpn 1, Hind III and Avr II sites</u>

$C_{Lambda}$
     +107                                +99
5' ACC TAG GAC GGT <u>AAG CTT</u> <u>GGT ACC</u> TCC GCC 3'
                        Hind III    Kpn 1

+107                                          +97
5' ACC TAG GAC GGT CA(C/G) (C/G)TT <u>GGT ACC</u> TCC GCC GAA CAC 3'
                                          Kpn 1

+110                           +102
5' CTT GGG CTG A<u>CC TAG G</u>AC GGT CAG CCG 3'
                     Avr II

Figure 8

A. Heavy Chain Variable Region:

| VH1 | 5' | CCATGGACTGGACCTGG | 3' |
| VH2 | 5' | ATGGACATACTTTGTTCCAC | 3' |
| VH3 | 5' | CCATGGAGTTTGGGCTGAGC | 3' |
| VH4 | 5' | ATGAAACACCTGTGGTTCTT | 3' |
| VH5 | 5' | ATGGGGTCAACCGCCATCCT | 3' |
| VH6 | 5' | ATGTCTGTCTCCTTCCTCAT | 3' |

B. Heavy Chain Constant Region Anti-Sense Strand:

IgM    5'    T TGG GGC GGA TGC ACT 3'
       (+119)                (+115)

IgG$_{1-4}$   5'   GA TGG GCC CTT GGT GGA 3'
              (+119)                (+115)

C. Light Chain Variable Region:

Kappa    5'    G ATG ACC CAG TCT CCA (G/T)CC TC 3'
               (+4)                           (+10)

Lambda   5'    CTC A(C/T)T (T/C)(G/A)C TGC (A/C)CA GGG TCC 3'
               (-9)                                      (-3)

D. Light Chain Constant Region Anti-Sense Strands:

Kappa    5'    AA GAC AGA TGG TGC AGC CA 3'
               (+115)                (+110)

Lambda   5'    G GAA CAG AGT GAC CGA GGG G 3'
               (+118)                  (+112)

Figure 16

PCR Primers for Human γ4 Constant Region

| 1) IDEC 462 3' PCR Primer |
|---|

5' GGGG <u>GGA TCC</u> TCA TTT ACC CAG AGA CAG GG 3'
     BamH I

| 2) IDEC 479 5' PCR Primer |
|---|

5' GGGG <u>GCT AGC</u> ACC AAG GGC CCA TCC GTC TTC 3'
     Nhe I

PCR Mutagenesis of Human γ4

| 3) IDEC 698 3' PCR Primer |
|---|

5' CCG GGA GA<u>T CAT GA</u>G AGT GTC CTT GGG TTT TGG GGG AAA CAG GAA GAC
     BspH I
             Glu                                         Pro
TGA TGG TCC CCC CTC GAA CTC AGG TGC TGG GCA TGG TGG GCA TGG GGG 3'

| 4) Midland GE212 5' PCR Primer |
|---|

Nhe I
5' TCC TCA <u>GCT AGC</u> ACC AA<u>G GGG CC</u>A TCC 3'
                            Destroys Apa I site

Figure 17

```
Frame 1  Met Lys His Leu Trp Phe Phe Leu Leu Leu Val Ala Ala Pro Arg Trp Val Leu Ser
         ATG AAA CAC CTG TGG TTC TTC CTC CTC CTG GTG GCA GCC CCC AGA TGG GTC TTG TCC
                      9          18          27          36          45          54
+1
Gln Val Gln Leu Gln Glu Ser Gly Pro Gly Leu Val Lys Pro Ser Glu Thr Leu Ser Leu Thr
CAG GTG CAG CTG CAG GAG TCG GGC CCA GGA CTG GTG AAG CCT TCG GAG ACC CTG TCC CTC ACC
            66          75          84          93         102         111         120

Cys Ser Val Ser Gly Gly Ser Ile Ser Gly Asp Tyr Tyr Trp Phe Trp Ile Arg Gln Ser Pro
TGC AGT GTC TCT GGT GGC TCC ATC AGC GGT GAC TAT TAT TGG TTC TGG ATC CGC CAG TCC CCA
           129         138         147         156         165         174         183

Gly Lys Gly Leu Glu Trp Ile Gly Tyr Ile Tyr Gly Ser Gly Gly Gly Thr Asn Tyr Asn Pro
GGG AAG GGA CTG GAG TGG ATC GGC TAC ATC TAT GGC AGT GGT GGG GGC ACC AAT TAC AAT CCC
           192         201         210         219         228         237         246

Ser Leu Asn Asn Arg Val Ser Ile Ser Ile Asp Thr Ser Lys Asn Leu Phe Ser Leu Lys Leu
TCC CTC AAC AAT CGA GTC TCC ATT TCA ATA GAC ACG TCC AAG AAC CTC TTC TCC CTG AAA CTG
           255         264         273         282         291         300         309

Arg Ser Val Thr Ala Ala Asp Thr Ala Val Tyr Tyr Cys Ala Ser Asn Ile Leu Lys Tyr Leu
AGG TCT GTG ACC GCC GCG GAC ACG GCC GTC TAT TAC TGT GCG AGT AAT ATA TTG AAA TAT CTT
           318         327         336         345         354         363         372

His Trp Leu Leu Tyr Trp Gly Gln Gly Val Leu Val Thr Val Ser Ser Ala Ser Thr Lys Gly
CAC TGG TTA TTA TAC TGG GGC CAG GGA GTC CTG GTC ACC GTC TCC TCA GCT AGC ACC AAG GGG
           381         390         399         408         417         426         435
```

Figure 17 Continued

```
Pro Ser Val Phe Pro Leu Ala Pro Cys Ser Arg Ser Thr Ser Glu Ser Thr Ala Ala Leu Gly
CCA TCC GTC TTC CCC CTG GCG CCC TGC TCC AGG AGC ACC TCC GAG AGC ACA GCC GCC CTG GGC
    444         453         462         471         480         489         498

Cys Leu Val Lys Asp Tyr Phe Pro Glu Pro Val Thr Val Ser Trp Asn Ser Gly Ala Leu Thr
TGC CTG GTC AAG GAC TAC TTC CCC GAA CCG GTG ACG GTG TCG TGG AAC TCA GGC GCC CTG ACC
    507         516         525         534         543         552         561

Ser Gly Val His Thr Phe Pro Ala Val Leu Gln Ser Ser Gly Leu Tyr Ser Leu Ser Ser Val
AGC GGC GTG CAC ACC TTC CCG GCT GTC CTA CAG TCC TCA GGA CTC TAC TCC CTC AGC AGC GTG
    570         579         588         597         606         615         624

Val Thr Val Pro Ser Ser Ser Leu Gly Thr Lys Thr Tyr Thr Cys Asn Val Asp His Lys Pro
GTG ACC GTG CCC TCC AGC AGC TTG GGC ACG AAG ACC TAC ACC TGC AAC GTA GAT CAC AAG CCC
    633         642         651         660         669         678         687

Ser Asn Thr Lys Val Asp Lys Arg Val Glu Ser Lys Tyr Gly Pro Pro Cys Pro Pro Cys Pro
AGC AAC ACC AAG GTG GAC AAG AGA GTT GAG TCC AAA TAT GGT CCC CCA TGC CCA CCA TGC CCA
    696         705         714         723         732         741         750

Ala Pro Glu Phe Glu Gly Gly Pro Ser Val Phe Leu Phe Pro Pro Lys Pro Lys Asp Thr Leu
GCA CCT GAG TTC GAG GGG GGA CCA TCA GTC TTC CTG TTC CCC CCA AAA CCC AAG GAC ACT CTC
    759         768         777         786         795         804         813

Met Ile Ser Arg Thr Pro Glu Val Thr Cys Val Val Val Asp Val Ser Gln Glu Asp Pro Glu
ATG ATC TCC CGG ACC CCT GAG GTC ACG TGC GTG GTG GTG GAC GTG AGC CAG GAA GAC CCC GAG
    822         831         840         849         858         867         876

Val Gln Phe Asn Trp Tyr Val Asp Gly Val Glu Val His Asn Ala Lys Thr Lys Pro Arg Glu
GTC CAG TTC AAC TGG TAC GTG GAT GGC GTG GAG GTG CAT AAT GCC AAG ACA AAG CCG CGG GAG
    885         894         903         912         921         930         939

Glu Gln Phe Asn Ser Thr Tyr Arg Val Val Ser Val Leu Thr Val Leu His Gln Asp Trp Leu
GAG CAG TTC AAC AGC ACG TAC CGT GTG GTC AGC GTC CTC ACC GTC CTG CAC CAG GAC TGG CTG
    948         957         966         975         984         993        1002

Asn Gly Lys Glu Tyr Lys Cys Lys Val Ser Asn Lys Gly Leu Pro Ser Ser Ile Glu Lys Thr
AAC GGC AAG GAG TAC AAG TGC AAG GTC TCC AAC AAA GGC CTC CCG TCC TCC ATC GAG AAA ACC
   1011        1020        1029        1038        1047        1056        1065

Ile Ser Lys Ala Lys Gly Gln Pro Arg Glu Pro Gln Val Tyr Thr Leu Pro Pro Ser Gln Glu
ATC TCC AAA GCC AAA GGG CAG CCC CGA GAG CCA CAG GTG TAC ACC CTG CCC CCA TCC CAG GAG
   1074        1083        1092        1101        1110        1119        1128

Glu Met Thr Lys Asn Gln Val Ser Leu Thr Cys Leu Val Lys Gly Phe Tyr Pro Ser Asp Ile
GAG ATG ACC AAG AAC CAG GTC AGC CTG ACC TGC CTG GTC AAA GGC TTC TAC CCC AGC GAC ATC
   1137        1146        1155        1164        1173        1182        1191

Ala Val Glu Trp Glu Ser Asn Gly Gln Pro Glu Asn Asn Tyr Lys Thr Thr Pro Pro Val Leu
GCC GTG GAG TGG GAG AGC AAT GGG CAG CCG GAG AAC AAC TAC AAG ACC ACG CCT CCC GTG CTG
   1200        1209        1218        1227        1236        1245        1254

Asp Ser Asp Gly Ser Phe Phe Leu Tyr Ser Arg Leu Thr Val Asp Lys Ser Arg Trp Gln Glu
GAC TCC GAC GGC TCC TTC TTC CTC TAC AGC AGG CTA ACC GTG GAC AAG AGC AGG TGG CAG GAG
   1263        1272        1281        1290        1299        1308        1317

Gly Asn Val Phe Ser Cys Ser Val Met His Glu Ala Leu His Asn His Tyr Thr Gln Lys Ser
GGG AAT GTC TTC TCA TGC TCC GTG ATG CAT GAG GCT CTG CAC AAC CAC TAC ACA CAG AAG AGC
   1326        1335        1344        1353        1362        1371        1380

Leu Ser Leu Ser Leu Gly Lys TER
CTC TCC CTG TCT CTG GGT AAA TGA
   1389        1398
```

SPR Association (left) and Dissociation (right) Phases

RECOMBINANT ANTI-CD4 ANTIBODIES FOR HUMAN THERAPY

FIELD OF THE INVENTION

This application is a continuation-in-part of U.S. Ser. No. 08/476,237 filed Jun. 7, 1995 (U.S. Pat. No. 5,756,096) which is a continuation-in-part of U.S. Ser. No. 08/379,072, filed Jan. 25, 1995 (U.S. Pat. No. 5,658,570), which is a continuation of U.S. Ser. No. 07/912,292, filed Jul. 10, 1992 (abandoned), which is a continuation-in-part of Newman et al., U.S. patent application Ser. No. 07/856,281, filed Mar. 23, 1992 (abandoned), which is a continuation-in-part of U.S. patent application Ser. No. 07/735,064, filed Jul. 25, 1991 (abandoned), the whole of which, including drawings, are hereby incorporated by reference. This invention relates to recombinant antibodies specific to CD4 which are useful for human therapy, and to methods for production of such antibodies.

BACKGROUND OF THE INVENTION

CD4 is a surface glycoprotein primarily expressed on cells of the T lymphocyte lineage including a majority of thymocytes and a subset of peripheral T cells. Low levels of CD4 are also expressed by some non-lymphoid cells although the functional significance of such divergent cellular distribution is unknown. On mature T cells, CD4 serves a co-recognition function through interaction with MHC Class II molecules expressed in antigen presenting cells. $CD4^+$ T cells constitute primarily the helper subset which regulates T and B cell functions during T-dependent responses to viral, bacterial, fungal and parasitic infections.

During the pathogenesis of autoimmune diseases, in particular when tolerance to self antigens breaks down, CD4+ T cells contribute to inflammatory responses which result in joint and tissue destruction. These processes are facilitated by the recruitment of inflammatory cells of the hematopoietic lineage, production of antibodies, inflammatory cytokines and mediators, and by the activation of killer cells.

Rheumatoid arthritis (RA), an inflammatory disease of the synovium, is one manifestation of an autoimmune phenomenon which results in erosion, deformity, and destruction of joints. Like most autoimmune diseases, the etiology of RA is not well defined. However, it is known that RA is characterized by elevated levels of activated $CD4^+$ T lymphocytes in the affected joints. Currently there is no cure for RA. First line therapy for RA is designed to provide relief for RA symptoms and to improve functional abilities over the short term. Second and third line immunosuppressors and steroids such as azathioprine, methotrexate and prednisolone, targeted at the underlying disease, are administered in more severe cases and are either only mildly effective or exhibit unacceptable toxicity for chronic therapy. Also, they do not protect against joint destruction.

Apart from RA, $CD4^+$ cells have also been implicated in other chronic conditions including psoriasis, insulin-dependent diabetes mellitus, systemic lupus erythematosus and inflammatory bowel diseases. Moreover, it is probable that CD4 expression may be involved in other autoimmune diseases.

Given the involvement of T cells in the development and maintenance of autoimmune diseases, immunosuppression has become an important treatment strategy. Available immunosuppressive drugs such as cyclosporin A have been used successfully for the treatment of transplant rejection. However, their toxic side effects renders them unacceptable for chronic therapy of autoimmune diseases.

Depletion of the entire T cell population, including the $CD4^+$ subset, in clinical settings, has been accomplished by methods including thoracic duct drainage, total lymphoid irradiation and lymphopheresis, resulting in clinical improvement in some patients. Current strategies are, however, focused on more selective agents that block unwanted immune responses without causing solid organ toxicity or other major side effects. One way this potentially can be achieved is by selective removal or inactivation of disease mediating T cells with monoclonal antibodies (mAbs). mAbs to CD4 represent one such strategy. In animal models of autoimmunity and transplantation, anti-CD4 mAbs arrest or reverse disease progression when administered prophylactically or therapeutically. In addition, initial results from some clinical trials with anti-CD4 mAbs in RA, psoriasis, inflammatory bowel disease and systemic vasculitis have provided some preliminary evidence of potential therapeutic efficacy.

Essentially, the objective of anti-CD4 mAb therapy is to arrest the autodestructive activity of $CD4^+$ cells, particularly during acute phases of autoimmune disorder. The ultimate therapeutic goal is to impose a state of immunological unresponsiveness (anergy) or long-term tolerance to the insulting antigens (or specific tissues) that sustain the underlying disease, without compromising normal host defenses against opportunistic infections. Apart from RA, CD4 mAbs may also be beneficial for the treatment of other autoimmune diseases, e.g., insulin-dependent diabetes mellitus, systemic lupus erythomatosis, psoriasis, inflammatory bowel disease, and multiple sclerosis.

Because of the potential importance of anti-CD4 mAbs as immunotherapeutics, numerous companies and research groups have reported anti-CD4 mAbs as potential therapeutic agents. For example, Centocor has reported an anti-CD4 mAb referred to as Centara which is a chimeric murine mAb to CD4. Further, Johnson & Johnson/Ortho has reported OKT-4a, an anti-CD4 mAb, which is a humanized murine mAb. Still further, Burroughs Wellcome has reported an anti-CD4 mAb which is a humanized rat mAb to CD4. Also, both Sandoz and MedImmune (in collaboration with Merck) have developed anti-CD 4 murine-humanized mAbs specific to CD4. Still further, Becton Dickinson, Immunotech and Boehringer Mannheim have both developed anti-CD4 mAbs.

Apart from anti-CD4 mAbs, various immunomodulators and drugs have been disclosed to possess potential applicability for treatment of RA. Such immunomodulators and drugs include, e.g., cellular adhesion blockers, cytokine receptor blockers, immunotoxins and T cell receptor antagonists. Specific examples include gamma interferon, anti-ICAM-1 (a murine anti-CD54 mAb which blocks leukocyte trafficking, adhesion), Campath-1H (rat-humanized anti-CDw52 mAb) IL-1 receptor, cA2 (a TNF-alpha chimeric mAb), CDP 571 (anti-TNF mAb), anti-IL-2R (humanized-murine anti-CD25 mAb), SDZ CHH 380 (murine-human anti-CD7 mAb), DAB486 IL-2 (IL-2 fusion toxin, non-specific for CD4 and CD8 cells), Antril (IL-1RA), anti-TCP (mAb's and proteins which target T cell receptor subsets), and XomaZyme-CD5 (murine anti-CD5 toxin conjugate).

Also, other immunomodulators and immunosuppressors having potential application for treatment of autoimmune diseases include Rapamycin (oral immunosuppressive), Therafectin, Leflunomide (immunosuppressive prodrug), Tenidap (cytokine modulator/CO-inhibitor), IMM-125 and RS-61443 (an oral immunosuppressive).

As noted, numerous monoclonal antibodies to CD4 having potential therapeutic applications have been reported.

For the most part, these antibodies comprise murine mAbs, chimeric or murine-humanized anti-CD4 mAbs.

Murine monoclonal antibodies have potential utility in the diagnosis of human disease as well as in clinical trials as therapeutics for treatment of both acute and chronic human diseases, including leukaemias, lymphomas, solid tumors (e.g., colon, breast, hepatic tumors), AIDS and autoimmune diseases. However, murine antibodies are disadvantageous because they often result in an immune antibody response in the host against the murine monoclonal antibodies.

Mouse/human chimeric antibodies have also been reported. These antibodies comprise the binding characteristics of the parental mouse antibody and effector functions associated with the human constant region. See, e.g., Cabilly et al., U.S. Pat. No. 4,816,567; Shoemaker et al., U.S. Pat. No. 4,978,775; Beavers et al., U.S. Pat. No. 4,975,369; and Boss et al., U.S. Pat. No. 4,816,397, all of which are incorporated by reference herein. Generally, these chimeric antibodies are constructed in preparing a genomic gene library from DNA extracted from pre-existing murine hybridomas (Nishman et al., 47 *Cancer Research,* 999 (1987)). The library is then screened for variable regions genes from both heavy and light chains exhibiting the correct antibody fragment rearrangement patterns. The cloned variable region genes are then ligated into an expression vector containing cloned cassettes of the appropriate heavy or light chain human constant region gene. The chimeric genes are then expressed in a cell line of choice, usually a murine myeloma line.

However, while such chimeric antibodies have been used in human therapy, they also are subject to some problems. Similar to murine monoclonal antibodies, human recipients may produce antibodies against the chimeric antibody. This is disadvantageous to the efficacy of continued therapy with the chimeric antibody.

As an improvement to conventional chimeric antibodies, some researchers have disclosed methods for the production of human monoclonal antibodies which should not be subject to such problems. See, e.g., Erlich et al., 34 *Clinical Chemistry,* 1681 (1988); Erlich et al., 7 *Hybridoma,* 385 (1988); Erlich et al., 6 Hybridoma, 151 (1987), and Erlich et al., 1 *Human Antibody Hybridomas,* 23 (1990). These references also hypothesize that non-human primate antibodies, e.g., chimpanzee monoclonal antibodies, should be well tolerated in humans because of their structural similarity to human antibodies. However, the production of antibodies in humans has obvious ethical constraints.

Because human antibodies are non-immunogenic in Rhesus monkeys (i.e., do not induce an antibody response), Erlich et al. also predict that primate antibodies should be non-immunogenic in humans. Erlich et al. (Id.) indicate that the testing of antibodies in humans is unnecessary if a primate antibody has a constant region identical to that of a human immunoglobulin or, at least, a structure no more different from a human immunoglobulin than different human antibodies differ from each other. Thus, they suggest that chimpanzee antibodies may be useful in human therapy.

As an improvement to known chimeric antibodies which are often antigenic in humans, related applications U.S. Ser. No. 08/476,237, filed Jun. 7, 1995, Ser. No. 08/347,072, filed Jan. 25, 1995, and Ser. No. 07/912,212, filed Jul, 10, 1992, Ser. No. 07/856,281, filed Mar. 23, 1992, and Ser. No. 07/735,064, filed Jul. 25, 1991, all incorporated by reference herein, describe the manufacture of Old World monkey monoclonal antibodies and chimeric antibodies derived therefrom produced by recombinant methods which contain the variable domain of an Old World monkey antibody (e.g., baboon or macaque), fused to a cloned human, chimpanzee or other monkey constant region or other monkey framework regions. These applications in particular describe the manufacture of such Old World monkey and chimeric antibodies derived therefrom against human antigens as well as the use of such chimeric recombinant antibodies as immunotherapeutic agents for the treatment of human disease.

These applications are based on the surprising discovery that evolutionarily distant monkeys (e.g., baboon or macaque monkeys (including cynomolgus and Rhesus monkeys)), unlike chimpanzees, are not only sufficiently different from humans to allow antibodies against human antigens to be raised in these monkeys even to relatively conserved human antigens, e.g., CD4 and CD54, but are sufficiently similar to humans to have antibodies that are structurally similar to human antibodies, so that no host anti-antibody response when such monkey antibodies, or recombinant chimeric antibodies derived therefrom, are introduced into a human.

These applications disclose that unlike some prior antibodies used for human therapy, including known chimeric antibodies, such chimeric antibodies do not suffer from several drawbacks, e.g., 1) immunogenicity and induction of human anti-antibody (HAA) response upon repeated administration necessary to treat chronic conditions, 2) relatively short half-life compared to human antibodies, and 3) lack of effector functions with human cells or complement.

The lack of these drawbacks is a significant advantage for human therapy. For example, in the case of chronic human diseases, including autoimmune diseases, or any disease where prolonged administration of an antibody is necessary, one of the major obstacles to repetitive antibody therapy is the host response to the therapeutic antibody. HAA responses are often unpredictable from one patient to another. Also, such responses are predominately, though not exclusively, directed against the constant region of the antibody molecule, and once they occur they often preclude, or reduce the effectiveness of therapy with that antibody, or another antibody of the same isotype. The recombinant chimeric antibodies described in the above-referenced applications will circumvent this problem and allow for the generation of antibodies of the appropriate specificity and desired effector function, and their use in production of recombinant antibodies.

These recombinant antibodies generally include an appropriate portion of the variable region of an antibody derived from an immunized monkey, which is necessary for antigen binding, and the constant region of an antibody from a human or chimpanzee. Therefore, this allows for maintaining specificities and high affinities of the monkey monoclonal antibodies, and desired effector functions by the appropriate selection of human or chimpanzee constant region.

Several of these related applications exemplify in particular a monkey/human chimeric antibody with specificity for CD4, referred to as CE9.1, which contains the heavy and light chain variable domain of an anti-CD4 monoclonal antibody produced in a cynomolgus monkey and the human immunoglobulin light chain lambda constant region and the human immunoglobulin heavy chain gamma 1 constant region. This antibody possesses some T cell depletion activity, but which is lower in comparison to previous CD4 monoclonal antibodies. However, it is desirable to produce antibodies which possess less or which are devoid of T cell depleting activity because this would potentially enhance their therapeutic potential.

These applications further describe preferred vector systems for the production of such chimeric antibodies, in particular TCAE 5.2 and TCAE 6 which comprise the following:

1) Four transcriptional cassettes in tandem order:
   (a) a human immunoglobulin light chain constant region. In TCAE 5.2 this is the human immunoglobulin Kappa light chain constant region (Kabat numbering amino acids 108–214, allotype Km 3) and in TCAE 6 the human immunoglobulin light chain lambda constant region (Kabat numbering amino acids 108–215, genotype Oz minus, Mcg minus, Ke minus allotype).
   (b) a human immunoglobulin heavy chain constant region; in both constructs the human immunoglobulin heavy chain is a gamma/constant region (Kabat numbering amino acids 114–478 allotype Gm1a, Gm 12).
   (c) DHFR; containing its own eukaryotic promoter and polyadenylation region; and
   (d) NEO; also containing its own eukaryotic promoter and polyadenylation region.

2) The human immunoglobulin light and heavy chain cassettes contain synthetic signal sequences for secretion of the immunoglobulin chains; and 3) The human immunoglobulin light and heavy chain cassettes contain specific DNA links which allow for the insertion of light and heavy immunoglobulin variable regions which maintain the translational reading frame and do not alter the amino acids normally found in immunoglobulin chains.

However, notwithstanding what has been previously described, there still exists a need in the art for improved antibodies which are specific to CD4, which possess low antigenicity in humans which may be used therapeutically, e.g., for the treatment of autoimmune diseases such as rheumatoid arthritis. In particular, there is a need for producing anti-CD4 antibodies which exhibit improved properties, e.g., longer half-life and/or which substantially lack or are devoid of depleting activity.

OBJECTS OF THE INVENTION

Toward this end, it is an object of the present invention to provide novel monoclonal and chimeric antibodies specific to CD4 having improved properties, e.g., longer half-life, low immunogenicity in humans and/or reduced or absence of T cell depleting activity. More specifically, it is an object of the invention to produce anti-CD4 chimeric antibodies which contain the antigen-recognition portion of an Old World money immunoglobulin specific to CD4 and human or monkey constant domain sequences, in particular human Kappa or lambda light chain constant region and human gamma 1 or gamma 4 or a mutated gamma 4 human heavy chain constant region sequences with altered effector functions and improved stability over the gamma 4 isotype.

It is a more specific object of the present invention to provide novel monoclonal and chimeric antibodies containing the specific monkey anti-CD4 variable heavy sequence shown in FIG. 1 and the monkey anti-CD4 variable light sequence shown in FIG. 2, fused to monkey or human constant domain sequences, preferably the human Kappa or lambda light chain constant domain sequence and the human gamma 1 or gamma 4 constant domain sequence or a mutated gamma 4 heavy chain with altered effector functions and improved stability over the gamma 4 isotype.

It is another object of the present invention to provide DNA sequences which provide for the expression of such improved chimeric anti-CD4 antibodies and vectors and host cells which may be used for the expression of such chimeric anti-CD4 antibodies. Preferably, such vectors will comprise the expression vectors referenced in the applications which are incorporated by reference herein, and the host cells will preferably be CHO cells.

It is still another object of the present invention to provide pharmaceutical compositions for use in the treatment or prophylaxis of CD4 related disorders, in particular autoimmune diseases, which contain a prophylactically or therapeutically effective amount of the subject improved chimeric anti-CD4 antibodies in combination with a pharmaceutically acceptable carrier.

It is yet another object of the present invention to provide methods of treatment or prophylaxis of CD4 related disorders, in particular autoimmune diseases and other conditions wherein immunosuppression is desirable by the administration of a therapeutically or prophylactically effective amount of the subject novel chimeric anti-CD4 antibodies in combination with a pharmaceutically acceptable carrier.

BRIEF DESCRIPTION OF THE FIGURES

FIG. 1 (SEQ ID NOS: 1–2) depicts the amino acid and DNA sequence of the light variable domain of CE9.1.

FIG. 2 (SEQ ID NOS: 3–4) depicts the amino acid and DNA sequence of the heavy variable domain of CE9.1.

FIG. 3 (SEQ ID NOS: 5–6) depicts the amino acid and DNA sequence of the human lambda variable and constant domains contained in CE9.1.

FIG. 4 (SEQ ID NOS: 7–8) depicts the DNA and amino acid sequence encoding the heavy chain variable and constant gamma 4 sequence.

FIG. 5 (SEQ ID NOS: 9–10) depicts the DNA and amino acid sequence encoding human heavy chain gamma 4 containing the E mutation.

FIG. 6 (SEQ ID NOS: 11–12) depicts the DNA and amino acid sequence encoding human heavy chain gamma 4 containing the P and E mutation.

FIGS. 7-1, 7-2 and 8 (SEQ ID NOS: 13–55) show the nucleic acid sequence of various leader sequences useful in the invention.

FIG. 12 shows the antibody dependent cellular cytotoxic properties of CE9.1 where lysis of SupT-18 target cells in the presence of γ interferon stimulated effector cells and where 4D9 is a murine anti-CD4 monoclonal antibody IgG2a.

FIG. 16 (SEQ ID NOS: 56–59) depicts suitable PCR primers for obtaining he human γ4 constant region.

FIG. 17 (SEQ ID NOS: 11–12) depicts the CE9γ4PE heavy chain sequence.

DETAILED DESCRIPTION OF THE INVENTION

Figure 9:
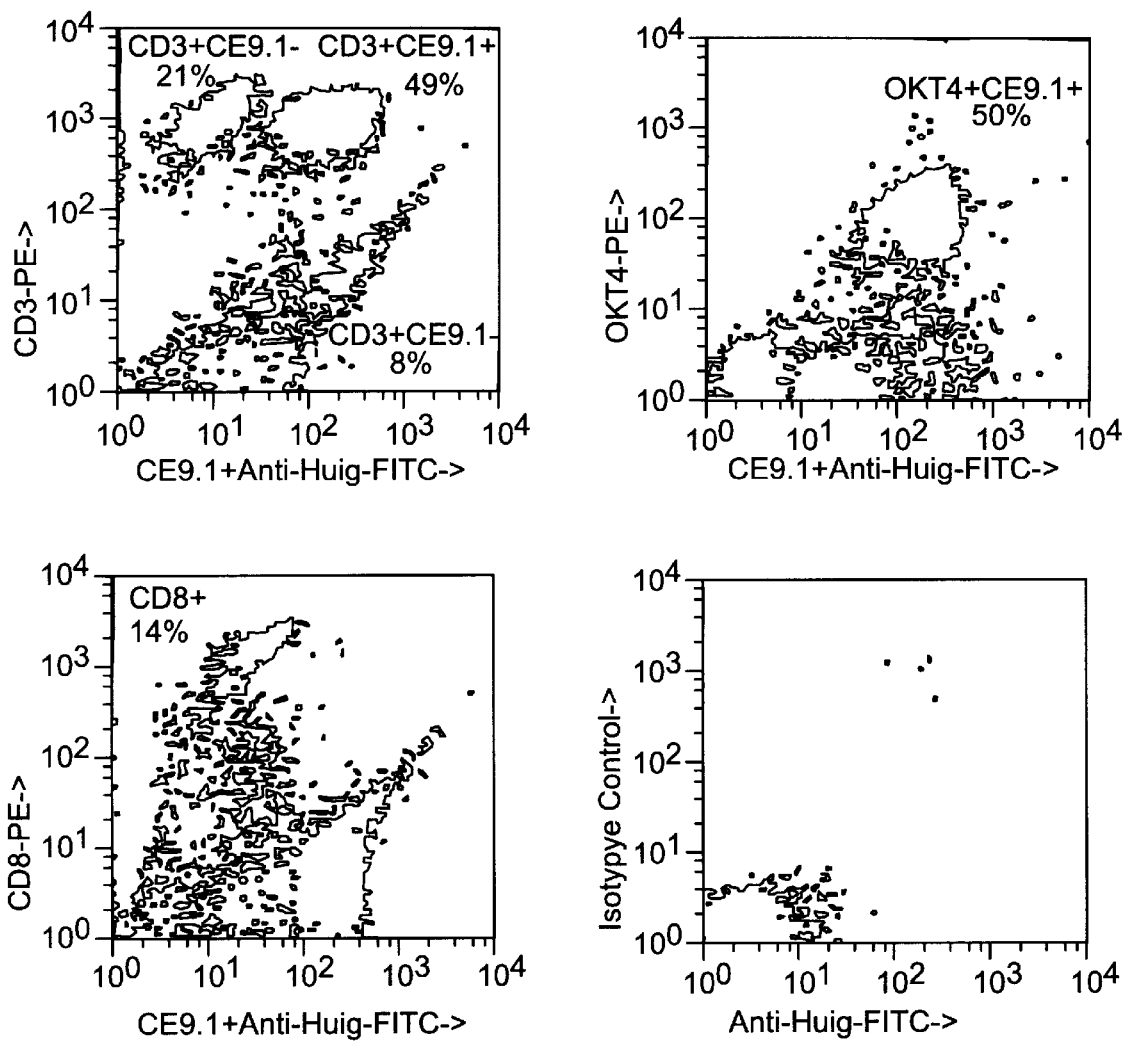
FIG. 9 shows a scattergram of the binding of CE9.1 to fresh human PMNCs where Panel A top right quadrant shows lymphocytes doubly stained with CE9.1 and OKT3, Panel B top right quadrant shows population doubly stained with CE9.1 and OKT4, Panel C top right quadrant shows absence of cells doubly stained with CD8 and CE9.1, and Panel D control shows cells stained with normal and human IgG.

The present invention provides novel monoclonal chimeric antibodies specific to CD4 which contain the antigen-binding portion of a variable region of an Old World monkey anti-CD4 monoclonal antibody fused to desired monkey or human constant domain sequences, preferably the human gamma 1, gamma 4 or a mutated gamma 4 human heavy chain constant domain and human Kappa or lambda light chain constant domain sequence. These antibodies exhibit improved properties in relation to conventional anti-CD4 monoclonal antibodies, e.g., high affinity to human CD4 and have little or no immunogenicity in humans. The gamma 4 versions show reduced or absence of effector function, e.g., Fc receptor binding activity or complement fixation, and little or no T cell depleting activity.

Methods for obtaining Old World monkey monoclonal antibodies specific to CD4 and clones which produce Old World monkey monoclonal antibodies specific to CD4 may be found in the afore-referenced related patent applications which are incorporated by reference herein.

In general, this comprises immunizing an Old World monkey against human CD4 antigen under conditions such that the Old World monkey produces anti-CD4 antibodies; immortalizing the cells of the monkey which are responsible for producing the anti-CD4 antibodies, e.g., by hybridoma fusion, viral transformation with *Herpes papio*, single B-cell cloning (also called "transient immortalization"), and production of a library of recombinant immunoglobulins. In preferred embodiments, this method includes selecting a B-cell from the monkey from either a peripheral blood leukocyte, the spleen, bone marrow or a lymph node; selecting a core which produces the appropriate antibody; rescuing the immunoglobulin genes encoding that antibody from the immortalized cell line; and expressing the genes in a producer cell line (i.e., a cell line which enables sufficient production of the antibody to be useful for human therapy). As is defined in the above-referenced applications, Old World monkeys include baboons and macaque monkeys (including Rhesus monkey and cynomolgus monkey).

As discussed supra, in the preferred embodiment the subject chimeric antibodies will comprise the anti-CD4 Old World monkey variable heavy and variable light sequences shown in FIG. 1 and FIG. 2, fused to human constant domain sequences. Suitable means for obtaining these specific variable heavy and variable light domain sequences are described in detail in U.S. application Ser. No. 08/476,237, filed Jun. 7, 1990 and Ser. No. 08/397,072, filed Jan. 25, 1995, as well as Ser. No. 07/912,292, filed Jul. 10, 1992, all of which are incorporated by reference in their entirety herein. These applications further disclose the entire nucleic acid and amino acid sequence of these sequences.

These variable heavy and domain sequences may be fused to any desired human constant domain sequences. The particular selection will affect the effector function of the resultant chimeric anti-CD4 antibody. Preferably, the human heavy chain constant domain will comprise gamma 1, gamma 4 or a mutated gamma 4 constant domain referred to herein as gamma 4E or a mutated gamma 4 referred to herein as gamma 4PE. The selection of gamma 4 is advantageous because it has been found to result in chimeric antibodies lacking T cell or substantially lacking T cell depleting activity (80–100% relative to gamma 1). This is believed to be because the gamma 4 constant domain is unable to bind complement. The constant domain may also be mutated to enhance the properties of the resultant chimeric antibody, e.g., stability and/or to eliminate depleting activity. In particular, the P and E modifications of the gamma 4 domain, which are described infra, are modifications of the gamma 4 in the hinge region which confer activity enhanced stability and eliminate depleting activity. Moreover, it is expected that other modifications should also provide chimeric antibodies having enhanced properties.

The human light chain constant domain contained in the subject chimeric anti-CD4 antibodies will preferably be the human Kappa or lambda light chain constant region, more preferably the human lambda light chain constant region. The amino acid and DNA sequences which encode human gamma 1, gamma 4, Kappa and lambda constant domains are known in the art. Also, the amino acid and nucleic acid sequences for human gamma 4 and E and PE mutants and lambda constant domain sequences may be found in FIGS. 4–6 and FIG. 3, respectively.

The exemplified embodiments of the invention include a specific chimeric anti-CD4 monoclonal antibody referred to as CE9.1 which comprises the antigen binding domains obtained from human sCD4-immunized cynomolgus macaques (shown in FIGS. 1 and 2), in combination with the constant domains of human IgG1, and monoclonal chimeric antibodies derived therefrom, e.g., CE9γ4, CE9γ4λK and CE9γ4E, CE9γ4PE which have the same antigen binding domains of CE9.1, but have been genetically engineered with a human IgG4 Fc binding domain framework. Monoclonal antibody CE9γ4E contains a leucine to glutamic acid mutation (L236E) near the hinge region of the antibody (the E modification). Monoclonal antibody CE9γ4PE contains the same leucine to glutamic acid mutation plus a serine to proline mutation (S229P) ("E" and "P" modification). The CE9γ4Kλ antibody differs from CE9γ4 by the replacement of its light chain constant region from a human K to a human λ subtype.

These constant domain switches and mutations were made because it is known that the biological responses of IgG antibodies depends on the composition of their carboxyterminal domains, i.e., their isotype. Thus, by altering the antibody isotype by protein engineering, it is potentially possible to modify the biological response of an IgG antibody, and more specifically the subject chimeric anti-CD4 monoclonal antibodies.

The desired outcome of this engineering strategy was that isotype switching of the Fc portion of the antibody would not diminish binding affinity of the CD4 antigen binding Fab regions. However, this was not known at the outset. It was possible that the change of the constant region or modification thereof could have adversely affected CD4 binding. Therefore, the resultant antibodies were assayed to determine the effects of modification on antibody properties, in particular CD4 antigen binding. In order to measure the possible effects of constant domain switching on antigen binding, known assay methods may be used. In particular, a study of the interaction between CD4 and CE9.1, CE9γ4, CE9γ4λk, CE9γ4E and CE9γ4PE was made by Scatchard analysis and surface plasmon resonance (SPR). The results of these assays demonstrated that CD4 binding to each of the tested antibodies was equivalent. Equilibrium dissociation constants at 25° C. for CD4 binding to the antibodies were all found by SPR to be approximately 1.0 nanomolar. The measurements further demonstrate that:

1) CD4 binding to the antibodies occurs by a two-site independent and identical binding model; and 2) the functional binding properties of the antigen binding domains are independent of structural modifications made to the Fc portion of the antibody including the gamma 1, gamma 4 or mutated gamma 4 isotypes. Therefore, the present invention provides evidence that isotype switching between IgG1 and IgG4 may be a useful strategy for engineering antibodies without loss of antigen binding affinity and more specifically, antibodies to CD4.

Also, as described infra, it was also found that the substitution of the gamma 1 constant domain with gamma 4 substantially reduced Fc receptor binding, complement fixation and T cell depleting activity and further that the E and P modifications respectively further eliminate Fc receptor binding and T cell depleting activity and provide for enhanced antibody stability. Therefore, it is reasonable to assume that other chimeric antibodies produced according to the invention (engineered to contain the human gamma 4 constant domain or mutated forms thereof) may be selected with altered Fc effector function, which substantially lack or are totally devoid of T cell depleting activity, and/or which exhibit enhanced stability. Methods of assaying T cell depleting activity, Fc effector function, and antibody stability are known in the art.

Therefore, the present invention provides specific recombinant antibodies which are primate/human chimeric monoclonal antibodies which are directed against the human CD4 antigen which exhibit improved properties, e.g., low T cell depleting activity and greater stability. Given these properties, these recombinant antibodies have particular utility as immuno-modulators and are especially useful for the treatment of autoimmune diseases such as rheumatoid arthritis, psoriasis, systemic lupus erythematosus (SLE) as well as non-auto immune indications such as graft-versus-host disease (GVHD) transplant rejection, asthma and HIV. Also, the subject antibodies possess utility as adjuncts in genetic therapy. In particular, the subject antibodies may be administered prior to, concurrent or after administration of a vector (containing a therapeutic DNA) to prevent or reduce the host humoral response to said vector. These diseases are exemplary of CD4 related conditions.

As described in greater detail in the Examples, the CE9.1 recombinant antibody is generated by grafting the antigen binding variable Fv domains from cynomolgus macaque to human constant regions e.g., IgG1 constant domains. More particularly, the CE9.1 antibody contains a human gamma 1 domain and the lambda constant domain. CE9γ4, CE9γ4λK, CE9γ4E and CE9γ4PE contain the gamma 4 constant domain or a mutated form thereof, and either the lambda or Kappa constant region. The resultant recombinant antibody sequences are indistinguishable from human immunoglobulin sequences. As a result, these antibodies, as well as the other CD4 antibodies produced by similar methods, upon in vivo administration in humans should exhibit reduced or no immunogenicity and slower serum clearance compared to similar murine monoclonal or mouse-human chimeric antibodies directed to CD4.

The CE9.1 antibody binds to domain 1 of human, but not macaque, CD4, a region which is involved in the interaction with MHC Class II molecules on antigen presenting cells. Also, assays have demonstrated that the other exemplified antibodies comprise the same antigen binding properties as CE9.1.

Potent immunomodulatory activity has been observed with the CE9.1 antibody both in vitro and in vivo. Given these properties, i.e., reduced immunogenicity, slower serum clearance and potent immuno-modulation, in comparison to other known anti-human CD4 mAbs that are murine or rodent derived, this antibody as well as the other antibodies described herein should be particularly suitable for long term therapy of diseases where immunosuppression is desirable, e.g., autoimmune disorders and chronic inflammatory diseases such as rheumatoid arthritis. However, it is expected that these antibodies should be useful for the treatment of many other disease conditions including, by way of example, Hashimoto's thyroiditis, primary myxoedema, thyrotoxicosis/Graves disease, pernicious anaemia, autoimmune atrophic gastritis, autoimmune carditis, Addison's disease, premature menopause, type I-diabetes mellitus, Good pasture's syndrome, myasthenia gravis, multiple sclerosis, male infertility, pemphigus vulgaris, pemphigoid, sympathetic ophthalmia, phacogenic uveitis, autoimmune haemolytic anaemia, idiopathic thrombocytopenic purpura, idiopathic leucopenia, primary biliary cirrhosis, active chronic hepatitis (HBs Ag negative), cryptogenic cirrhosis, inflammatory bowel disease syndrome, Sjogren's syndrome, psoriasis, rheumatoid arthritis, dermatomyositis, scleroderma, mixed tissue connective disease, discoid lupus erythematosus, systemic vasculitis, and systemic lupus erythematosus (SLE).

As discussed above, rheumatoid arthritis (RA) is an inflammatory disease of the synovium which comprises one manifestation of an autoimmune phenomenon which results in erosion, deformity, and destruction of joints. As is true with most autoimmune diseases, the etiology of RA is not well defined but is characterized by elevated levels of activated $CD4^+$ T-lymphocytes in the affected joints. Currently there is no cure for RA and therapy for treatment of this debilitating disease is designed only to provide relief of symptoms and improvement in functional abilities over the short term. Moreover, second and third line immunosuppressants and steroids such as azathioprine, methotrexate and prednisolone aimed at the underlying disease are only given in more severe cases and are usually mildly effective or exhibit unacceptable toxicity when used for chronic therapy. By contrast, it is expected that the subject antibody will be suitable over prolonged and chronic administration given the fact that it exhibits reduced immunogenicity, longer half life and potent immunomodulatory activity as compared to other known anti-human CD4 mAbs that are murine or rodent derived.

Essentially, the exemplified recombinant anti-CD4 monoclonal antibodies described in this application or other antibodies produced according to the present invention and as described in the above-referenced application (incorporated by reference) will likely mediate therapeutic activity by arresting or altering the destructive activity of $CD4^+$ cells, particularly during acute phases of autoimmune disorders such as rheumatoid arthritis. Thus, administration of antibodies according to the invention will result in a state of immunological unresponsiveness (anergy) or long term tolerance to the insulting antigens (or specific tissues) that sustain the underlying disease without compromising normal host defenses against opportunistic infections. Apart from RA, CD4 monoclonal antibodies should be beneficial in the treatment of the above-identified diseases and afford particular application for the treatment of insulin-dependent diabetes mellitus, systemic lupus erythematosus, cirrhosis, inflammatory bowel disease, multiple sclerosis, as well as other auto-immune diseases. They may also be useful in the treatment of non-autoimmune diseases such as leukemia lymphoma graft-versus-host disease, transplant rejection, asthma and HIV.

Recombinant anti-CD4 monoclonal antibodies produced according to the invention should mediate the desired in vivo therapeutic effect through one or more of the following mechanisms:

i) blocking the interaction of CD4 with MHC class 2 molecules;

ii) down modulation of cell surface CD4;

iii) causing anergy and/or apoptosis;

iv) depletion of CD4 cells; or v) induction of tolerance to autoantigens.

Although transient depletion of $CD4^+$ cells results in immunosuppression and perhaps normalization of an otherwise hyperactive immune system, the main mechanism by which anti-CD4 antibodies exhibit their in vivo effect is not necessarily dependent on T cell depletion. Rather, it is believed that antibody binding to the CD4 molecule prevents helper T cell activation by antigens bound to T cell receptor leading to antigen-specific T cell anergy or tolerance. For example, the CE9.1 antibody which comprises a human gamma 1 domain exhibits substantial immunosuppression activity. However, it only partially depletes CD4 cells in chimpanzees. Moreover, results in humans indicate that this antibody results in substantially less cell depletion compared to other monoclonal antibodies now in clinical trials.

Also, in in vivo experimental models, allograft specific tolerance has been induced by non-depleting anti-CD4 antibodies administered at the time of transplantation. The maintenance of the tolerance state did not require a depleting anti-CD4 antibody but does appear, however, to be dependent on the continued presence of antigen. Based on these findings, it is expected that the subject recombinant antibodies or other recombinant anti-CD4 antibodies produced according to the invention should be suitable for treatment of autoimmune diseases. Brief treatment schedules with anti-CD4 antibodies will interfere with helper T cell responses against auto antigens leading to long-lasting clinical improvements in the absence of generalized immunosuppression.

Based on the information contained in the subject application, and using known methods, one skilled in the art can readily ascertain a safe, tolerated and effective regimen of the exemplified recombinant anti-CD4 antibodies disclosed herein as well as other antibodies produced substantially according to the invention.

As noted, CE9.1 is an anti-CD4 monoclonal antibody macaque-human chimeric antibody which is of the IgG1 molecule which is expressed in Chinese hamster ovary (CHO) cells which exhibits 91–92% homology with human immunoglobulin framework regions. Therefore, this molecule should exhibit reduced or even no immunogenic response in humans and should exhibit longer serum half-life compared to murine monoclonal or mouse-human chimeric antibodies. Also, the antibody exhibits limited cross reactivity with human tissues. For example, no evidence of binding of this antibody to non-lymphoid tissues was observed in testing. As expected, the antibody binds to some but not all of the lymphoid cells from peripheral blood and other organs. Also, it has been found that this antibody reacts with chimpanzee $CD4^+$ T cells but does not react with $CD4^+$ T cells from rhesus, cynomolgus or pigtail macaques, baboons, rats, mice, or rabbits. Therefore, based on this reactivity, chimpanzees comprise a relevant species to confirm the in vivo pharmacological affects of this antibody, i.e., its ability to function as an effective immunosuppressant.

The CE9.1 antibody exhibits reversible T cell depleting activity in chimpanzees. Moreover, it is likely to be improved over current murine and murine/chimeric anti-CD4 monoclonal antibodies by virtue of its expected longer half-life in human serum and reduced potential adverse immunogenic effects. Also, given the presence of human constant domain sequences, it is expected that the subject antibody upon administration in humans will maintain the normal effector functions of human antibodies. In fact, the effector functions of the CE9.1 antibody as well as the other referenced antibodies has been evaluated in several different assays. The CE9.1 antibody was found to exhibit inhibitory activity in mixed lymphocyte reaction (MLR), to exhibit weak C1q binding, but not to exhibit complement mediated cellular cytotoxicity. Also, it was found to exhibit antibody dependent complement cellular cytotoxicity activity (ADDC) and to bind FcR. Also, the CE9.1 antibody has been evaluated in vivo in chimpanzees wherein it was found that administration results in partial depletion of CD4 cells, and modulation of the CD4 receptor.

The CE9.1 antibody has been administered to chimpanzees at various dosages. More specifically, the effects of dosages of 0.1, 0.3, 1, 5, and 10 milligrams/per kilogram were studied in a chimpanzee dosed at 7 to 14 day intervals. No clinical evidence of toxicity was observed. Dosages of 10 milligram per kilogram or greater caused an 80–95% reduction in circulating $CD4^+$ cells 24 hours after dosing. Significant depression of $CD4^+$ cells was not observed seven days after a dose of 1 milligram/kilogram. After a dose of 5 milligrams/kilogram circulating $CD4^+$ cell counts recovered to approximately 40% of base line after seven days and approximately 60% of base line after fourteen days. After a dose of 10 milligrams/kilogram circulating $CD4^+$ cell counts had not recovered seven days after treatment and recovered to only 40% of base line forty-two days after dosing. No changes in other clinical pathology parameters were observed.

The CE9.1 antibody has also been tested in humans. For example, the activity of the CE9.1 antibody has also been evaluated in single dose-escalating phase 1 trials in rheumatoid arthritis patients. These results were very promising. Specifically, about half of the patients who were administered exhibited at least a 30% improvement in their tender joint scores, with the adverse event profile being extremely benign. Moreover, as discussed supra, while it was initially assumed that CE9.1 would be depleting, in fact this antibody exhibited only partial and transient depletion upon single administration. The partial non-depleting nature of this antibody may be beneficial because in a number of animal studies it has been reported that $CD4^+$ T cell depletion is apparently not necessary for efficacy of CD4 monoclonal antibodies. (See Carteron et al., Induction of Immune Tolerance During Administration of Monoclonal Antibody to L3 T4 Does not Depend on L3 T4+ Cells, Underlying Journal of Immunology, 140:713–716 (1988); Carteron et al, F(ab')2 Anti-CD4 and Intact Anti-CD4 Monoclonal Antibodies Inhibit the Accumulation of $CD4^+$ T Cells, $CD8^+$ T cells and BT T Cells and P cells in the Kidneys of Lupus-Prone NZB/NZW Mice, Clinical Immunology Immunopathology, 56:373–383 (1990).) Thus, this antibody may function like a classical receptor antagonist by: i) blocking interaction of CD4 with its counter receptor MHC II; or ii) causing modulation of CD4 from the cell surface. Under these conditions, $CD4^+$ T cell responses that require the participation of the CD4 receptor would be attenuated or blocked. The fact that the subject CE9.1 antibody apparently exhibits little depleting activity in humans is advantageous because it may improve safety, may obviate the need for frequent monitoring of $CD4^+$ cell counts, and may also improve efficacy.

The CE9.1 antibody was designed to reduce CD4 cell numbers in vivo via Fc receptor and complement binding mechanisms. Studies in chimpanzees indicate that CE9.1 causes partial depletion of CD4 cells, and initial results indicate that cell depletion in humans is much reduced compared to other known CD4 mAbs. However, it is also desirable to produce antibodies which are devoid of depleting activity.

The utility of "non-depleting" CD4 mAbs should be improved because of the following:

i) depletion of CD4 cells is not required for efficacy of CD4 mAbs;

ii) absence of CD4 cell depletion should enhance the safety thereof;

iii) superior safety permits mAbs to be used earlier in the disease process;

iv) absence of CD4 cell depletion should improve efficacy; and v) absence of CD4 cell depletion will obviate or reduce the need to frequently monitor CD4 cell counts, thus increasing convenience and cost of the overall treatment.

This is supported by the fact that in a number of animal models, it has been shown that $CD4^+$ T cell depletion is not required for efficacy of CD4 mAbs. Thus, a non-depleting CD4 mAb would function like a classical receptor antagonist by:

i) blocking the interaction of CD4 with its counter receptor MHCII, ii) causing modulation of CD4 from the cell surface, or iii) causing T cell anergy and/or apoptosis.

Thereby, $CD4^+$ T cell responses that require the participation of the CD4 receptor would be altered or blocked.

Generally, T cell responses which are driven by strong or high affinity antigens appear to be independent of $CD4^-$ co-receptor functions and thus would not be effectively blocked by CD4 mAbs. Conversely, T cell responses to weak antigens (such as autoantigens) require $CD4^-$ co-receptor function and therefore would be inhibited by CD4 mAb. Normally, strongly autoreactive T cells (T cells with high affinity TCRs to self antigens) are removed in the thymus by "clonal deletion" and therefore never appear in the periphery. By contrast, T cells which drive the autoimmune response are believed to be weakly self-reactive cells which have escaped the normal mechanisms of peripheral tolerance. Such cells depend on the participation of co-receptors, such as CD4, for the full elaboration of a response. Therefore, blocking the co-receptors would deprive these T cells of crucial co-signaling functions which would result in partial activation or anergy. Also, as noted above, it is further desirable to produce chimeric antibodies specific to CD4 having greater stability (longer in vivo half-life).

Toward that end, various chimeric antibodies were synthesized which contain the gamma 4 human constant domain. This domain was selected because it apparently does not bind human complement or $FCT\gamma 1$ receptors. Therefore, it was hypothesized that chimeric antibodies containing this constant domain would lack or substantially lack T cell depleting activity. Also, several chimeric antibodies were made which contained known modifications of the gamma 4 constant domain. In particular, several contain the "E" modification which is described by Duncan et al., Nature, 332:563–564 (1988), and Winter et al., WO 88/07089 (1988), which modification has been disclosed to reduce complement and $FC\gamma 1$ receptor binding. This modification comprises the change of leucine to glutamic acid at position 236 (248 Kabat numbering) to abate any residual Fc receptor binding. Also, several chimeric antibodies contain the "P" modification which is disclosed by Angal et al., Mol. Immunol., 30:105–8 (1993). This modification which comprises the change of a serine at position 229 (241 Kabat numbering) to a proline enhances stability (serum half-life) by stabilizing disulfide bonds between the heavy chains and has been reported to enhance improved tissue distribution relative to a chimeric IgG4 lacking the modification.

More specifically, the rationale for development of $CE9\gamma 4$ was to abrogate complement fixing and decrease FcR binding activities. This antibody differs from CE9.1 in that it contains the human gamma 4 constant domain (not gamma 1). However, while this was desired the outcome was not of a routine or predictable nature. Indeed, the present inventors found that chimeric antibodies containing unmodified γ9 had the same Fc receptor binding as the γ2 antibody. By contrast, the rationale for making CE9γ4λK was to enhance productivity of γ4 construct. This antibody differs from the CE9.1 in that it contains the human Kappa light chain rather than lambda. Assessment of CE9γ4 in vitro by an Fc receptor binding assay which measures the binding of antibody to stimulated monocytes and monocytic cell lines, showed that CE9γ4 still possessed significant Fc receptor binding activity. Furthermore, in this assay system, CE9γ4 binding was indistinguishable from CE9.1 (gamma 1). Thus, the rationale for manufacture of CE9γE was to completely abrogate any residual FcR binding over chimeric antibodies containing unmodified γ4. CE9γE contains the gamma 4 constant domain modified at one site (E modification). Finally, the rationale for the manufacture of CE9γ4PE was to enhance the stability over chimeric antibodies containing unmodified γ4 or a mutation at one site (E modification). This antibody contains the gamma 4 constant domain modified at two sites (P and E modification).

As discussed, the human γ4 constant domain was selected as the isotype for abrogation of effector functions, i.e., reactivity with human Fcγ receptors or C1q, and absence of depletion of CD4+ cells in vivo. These four candidates were selected and expressed in CHO cells.

Two of these candidate monoclonal antibodies were selected for more extensive study, i.e., CE9γ4E and CE9γ4PE. As noted, both of these contain a glutamic acid substitution in the CH2 region introduced to eliminate residual FcR binding associated with γ4 constant region. In addition, CE9γ4PE contains a proline substitution in the hinge region, intended to enhanced the stability of the heavy chain disulfide bond interaction.

These antibodies were found to be indistinguishable in their affinity for CD4, molecular weight, stability to heat denaturation, suppression of MLR, absence of binding to FcR, and lack of activity in ADCC and CDC. Thus, both of these antibodies exhibit in vitro criteria for a high affinity CD4 mAb with no FcR and complement effector functions.

The properties of CE9.1 and CE9γ4PE are compared in Table 1. Reduced Fc receptor binding is intended to refer to chimeric antibodies which bind to the Fc receptor less than 1 γ1 containing chimeric antibodies, preferably at least 30 to 80% reduced in comparison thereto and more preferably at least 50 to 80% reduced and most preferably totally abrogated. However, as evidenced by the results with the unmodified gamma 4 chimeric antibody the desired outcome was not of a predictable nature.

TABLE 1

Comparison of Effector Functions of CE9.1 and CE9γ4PE

| Activity | CE9.1 | CE9γ4PE |
|---|---|---|
| In vitro | | |
| MLR | Yes | Yes |
| C1q Binding | Weak | No |
| CDC | No | No |
| ADCC | Yes | No |
| FcR Binding | Yes | No |
| In vivo (Chimpanzee) | | |
| Depletion of CD4 Cells | Partial | No |
| CD4 Receptor Modulation | Yes | Yes |

TABLE 1-continued

Comparison of Effector Functions of CE9.1 and CE9γ4PE

| Activity | CE9.1 | CE9γ4PE |
|---|---|---|
| In vivo (HuCD4+ Transgenic mice) | | |
| Depletion of CD4 cells | Partial | No |
| CD4 Receptor Modulation | Yes | Yes |

ADCC = Antibody Dependent Cellular Cytotoxicity
CDC Complement Mediated Cellular Cytotoxicity
FcR Fc Receptor
MLR Mixed Lymphocyte Reaction Thus, these results confirm that chimeric antibodies may be produced according to the invention which bind human CD4, which lack certain effector functions by virtue of the selection of specific constant domain sequences.

In using the exemplified chimeric anti-CD4 antibodies or other chimeric antibodies produced according to the invention as immunosuppressants or CD4 modulators for the treatment of autoimmune disorders, including for example rheumatoid arthritis, such antibodies may be administered alone or in combination with other compounds suitable for treatment of the particular disease condition. For example, the subject antibody may be administered in combination with other proteins, for example monoclonal antibody soluble receptor proteins to TNF-alpha, monoclonal antibodies to IL2 receptor, monoclonal antibodies and receptor fusion proteins which antagonize the CD40/gp39 interaction and CTLA 4-Ig in monoclonal antibodies which antagonize the B7/CD28 interaction. Also, in the case of treatment of rheumatoid arthritis, the subject antibody may be administered in combination with other therapeutics, for example Rapamycin, Leflunomide, Tenidap, RS-61443 (Mycophenolate Mofetil), Surenyl (sodium Hyaluronate), anti-TCP (Vβ17) peptide vaccine, Anerva X (anti-MHC vaccine), and extracorporeal protein A immunoabsorbents or combinations thereof. Additionally, the subject antibody may be administered in combination with other antibodies produced according to the invention or known in the art which are specific to human CD4. This may result in synergistic effects, for example, if these antibodies bind to different epitopes of the CD4 protein.

The following examples are presented to further describe the invention.

EXAMPLE 1

Cloning and Expressing a Monkey/Human Chimeric Antibody with Specificity for CD4

The following is a specific example of the methods and antibodies of this invention.

Generation of Monkey Immortalized B-cell Lines

An adult cynomolgus monkey (White Sands New Mexico Primate Center) was immunized intramuscularly, at multiple sites, with 150–300 μg of soluble CD4 (sCD4) or cell membranes ($1 \times 10^8$ cells) from the CD4 positive cell line SupT1 using a standard adjuvant. Immunization was repeated every 2–3 weeks a total of six times. The monkey was boosted by injection of 100 μg of sCD4 into the inguinal region of one thigh and one week later the draining lymph node from the same thigh surgically removed. Lymphocytes were removed from the lymph node by slicing the tissue and rinsing with sterile DMEM medium. The cell suspension was passed through a nylon gauze and collected by centrifugation at 1000× g for 10 minutes.

Approximately 1×10⁸ lymphocytes were suspended in Tris-ammonium chloride buffer (16 mM, pH 7.5) and warmed to 37° C. for 5 minutes to lyse the erythrocytes. Lymphocytes were collected by centrifugation and resuspended in L-leucine methyl ester (LME) and incubated at 37° C. for 45 minutes. The LME treated cells were filtered through a nylon screen and centrifuged. 1 ml of fetal calf serum was added, the cells suspended and washed twice in serum-free RPMI. The cells were counted and mixed into a single 50 ml conical centrifuge tube together with an equal number of K6H6/B5 heteromyeloma cells, prewashed twice in serum free medium. Cells were gently suspended in 1 ml of 50% PEG (polyethylene glycol) added slowly with gentle stirring over a 1 minute period. The cells were then resuspended by the addition of 20 ml of serum-free medium over a 5 minute period, with gentle mixing to dilute out the PEG. After washing twice with serum-free medium cells were resuspended at a concentration of 5×10⁵/0.1 ml in RPMI medium, containing 20% fetal calf serum and gentamycin and placed into 96 well micro tissue culture plates at 0.1 ml per well. An equal volume of HAT medium (0.1 ml) was added to each well and the hybrids allowed to grow for 14–17 days before screening.

Screening of Fused Cell Hybrids for the Production of Anti-CD4

The assay to determine anti-CD4 specificity was as follows: ELISA plates were coated with recombinant sCD4 at a concentration of 100 ng per well and blocked with 1% bovine serum albumin in PBS. 50 μl aliquots of hybridoma supernatant were removed from each well and allowed to incubate with the sCD4 coated plates for 60 minutes. Binding was detected by incubation with $^{125}$I labeled goat anti-human or goat anti-monkey Ig for 60 minutes. After washing four times with distilled water, the wells were counted in a gamma counter. Positive wells were re-assayed in duplicate and the hybridoma cells from those wells subcloned three times, first at 5 cells per well then twice at 1 cell per well. At this stage anti-sCD4 positives were screened for the ability to bind to cell surface CD4. This was done by inhibition of binding of an anti-CD4 murine monoclonal, termed 1F3, to the CD4 positive cell line supT1. Briefly this was done by co-incubating different amounts of monkey anti-CD4 and 10 μg of $^{125}$I-labeled 1F3 with 3×10⁵ supT1 cells/well in a 96 well plate. After incubation for 1 hour at room temperature (about 20–25° C.) cells were removed by vacuum onto glass fiber filters. After extensive washing with PBS the filters were counted in a gamma counter to determine the inhibition of 1F3 binding to supT1 cells by the monkey hybridoma supernatants.

A candidate clone was chosen which produced an antibody that showed strong inhibition against 1F3. The clone was isotyped using human isotyping reagents and found to be an IgG2 possessing a lambda light chain. This cell line was grown up to larger numbers for cloning of its immunoglobulin genes.

Cloning of Heavy and Light Chain Variable Region Genes from Monkey Immortalized B-cells Total RNA was isolated from 1×10⁷ monkey immortalized B-cells using the guanidinium isothiocyanate method. One tenth of the total RNA was used to make single stranded cDNA using an oligo-dT oligonucleotide primer and reverse transcriptase. One tenth of the amount of single stranded cDNA was used to set up PCR reactions. The six PCR reactions each included one of six 5' $V_H$ family specific oligonucleotide primers containing a Sal I restriction site together with an IgG 3' constant region oligonucleotide containing an Nhe I site, both shown in FIG. 7-1. Similarly, five PCR reactions, utilizing one of five 5' lambda leader sequence oligonucleotide primers containing a Bql II site and a 3' lambda constant region prime containing an Avr II site, were run. Reaction conditions were as described above. Each PCR reaction was run in triplicate. The products of each of the heavy chain and light chain amplification reactions were run on 1.2% agarose gels. The VH4 heavy chain primer (SEQ ID NO: 16) (5'-ACTAAGTCGACATGAAACACCTGTGGTTCTT 3') and lambda primer (SEQ ID NO: 36) (5' ATCACAGATCTCT-CACCATGACCTGCTCCCCTCTCCTCC 3') gave strong bands on agarose gel electrophoresis. The products of these reactions were used for cloning into the vector TCAE 6, which contains human IgG1 and human lambda constant region sequences.

Cloning of the two variable region genes into the expression vector TCAE 6 was done sequentially. First, the heavy chain PCR product and the vector TCAE 6 were digested with the restriction enzymes Sal I and Nhe I, the products extracted with phenol/chloroform, and passed through a SEPHADEX G-25 spin column. The PCR product was ligated to the cut vector overnight at 14° C. in the presence of T4 DNA ligase. Approximately 500 ng total DNA was ligated in a volume of 10 μl with an insert/vector molar ratio of 10:1. Ligated material was used to transform XL-1 Blue competent cells (Stratagene) and the transformed cells plated onto LB agar plates containing 50μg/ml ampicillin. Colonies of ampicillin resistant bacteria were picked and grown as 5 ml minicultures. Plasmid DNA was extracted from each of these cultures by a standard alkaline lysis method, cut with the restriction enzymes Sal I and Nhe I and the products run on a 1.2% agarose gel. Plasmids with inserts of approximately 450bp were used as templates for the subsequent cloning of light chain variable regions. The products of the light chain PCR reaction as well the plasmid containing the heavy chain insert were cut with the restriction enzymes Bgl II and Avr II and ligated together. Plasmid minicultures were screened by cutting with Bgl II and Avr II. Digests giving an insert of approximately 400–450 bp were scored positive. Plasmids containing both Sal I/Nhe I and Bgl II/Avr II inserts were grown up in larger quantities for DNA sequencing.

The tandem chimeric antibody expression vectors TCAE 5.2 and TCAE 6 were derived from the vector CLDN, which itself is a derivative of the vector RLDN10b (253 *Science,* 77–79 (1991)). RLDN10b in turn is a derivative of the expression vector TND (7 DNA, 651–661 (1988)).

RLDN10b differs from the vector TND in the following ways. The dihydrofolate reductase (DHFR) transcriptional cassette (promoter, cDNA, and polyadenylation region) was placed in between the tissue plasminogen activator cassette (t-PA expression cassette) and the neomycin phosphotransferase (NEO) cassette so that all three cassettes are in tandem and in the same transcriptional orientation. In addition, the DHFR gene promoter in CLDN has been replaced by the mouse beta globin major promoter (3 *Mol. Cell Biol.,* 1246–54 (1983)) and the t-PA cDNA replaced by a polylinker. All three eukaryotic transcriptional cassettes (Expression, DHFR, NEO) can be separated from the bacterial plasmid DNA (pUC9 derivative) by digestion with the restriction endonuclease NotI.

CLDN differs from RLDN10b because the Rous LTR in front of the polylinker has been replaced by the human cytomegalo-virus immediate early gene promoter enhancer (41 *Cell,* 521 (1985)).

The expression vectors TCAE 5.2 and TCAE 6 differ from CLDN in that:

1) They contain four transcriptional cassettes (instead of three), in tandem order:
   (a) A human immunoglobulin light chain constant region derived via amplification of cDNA by a polymerase chain reaction. In TCAE 5.2 this is the human immunoglobulin light chain kappa constant region (Kabat numbering amino acids 108–214, allotype Km3), and in TCAE 6 the human immunoglobulin light chain lambda constant region (Kabat numbering amino acids 108–215, genotype Oz minus, Mcg minus, Ke minus allotype).
   (b) A human immunoglobulin heavy chain constant region; in both constructs the human immunoglobulin heavy chain was a gamma 1 constant region (Kabat numbering amino acids 114–478 allotype Gm1a, Gm1z), which was derived via amplification of cDNA by a polymerase chain reaction.
   (c) DHFR; containing its own eukaryotic promoter and polyadenylation region.
   (d) NEO; also containing its own eukaryotic promoter and polyadenylation region.

2) The human immunoglobulin light and heavy chain cassettes contain synthetic signal sequences for secretion of the immunoglobulin chains 3) The human immunoglobulin light and heavy chain cassettes contain specific DNA linkers which allow for insertion of light and heavy immunoglobulin variable regions which maintain the translational reading frame and do not alter the amino acids normally found in immunoglobulin chains. The incorporation of the changes described, led to the construction of the vectors TCAE 5.2 and TCAE 6. The cloning of the immunoglobulin light and heavy variable region genes, from the anti-CD4 heterohybridoma cell line E9.1, into TCAE 6 led to the construct which is deposited in the ATCC. The construct, which has been deposited, and which encodes for the CE9.1 antibody contains the cynomolgus monkey immunoglobulin heavy chain variable region and cynomolgus monkey immunoglobulin light chain variable region, whose sequences are shown in FIGS. 1 and 2, respectively, cloned from the anti-CD4 hybridoma cell line E9.1. The heavy chain constant region is of human origin of the gamma 1 isotype and Gm1a, Gm1z allotype. The lambda light chain constant region is also of human origin, of the Oz minus, mcg minus genotype and Ke minus allotype. The immunoglobulin genes are cloned into the mammalian expression vector TCAE 6, described in the afore-referenced applications incorporated by reference, which, when electroporated into the mammalian cell line CHO produced a monkey/human anti-CD4 chimeric antibody. The DNA construct described herein, has been used to transform the bacterial strain XL-1 Blue, selected in the antibiotic ampicillin and deposited as a bacterial cell suspension in sterile LB medium containing 15% glycerol.

DNA Sequencing

Plasmid DNA was prepared from 100 ml cultures. It was further purified by precipitating (1 volume) with a mixture of 2.5M sodium chloride and 20% polyethylene glycol (6 volumes) on ice for 15 minutes. After centrifugation at 10,000× g for 20 minutes, the pellet was washed with 70% ethanol, recentrifuged and dried in a Speedivac (Savant). The pellet of DNA was resuspended in deionized water at a concentration of 150–250 μg/ml. Sequencing was carried out on 5 μg of double stranded DNA using the technique of Sanger. Sequencing primers which were homologous to sequences within the expression vector upstream and downstream of either the light chain or heavy chain inserts were used. The inserts were sequenced in both 5' to 3' and 3' to 5' directions. Two clones of anti-CD4 light chain and two clones of anti-CD4 heavy chain each generated from separate PCR reactions were sequenced in parallel in order to determine whether any nucleotide changes had been introduced during the PCR reaction. Both of the chosen heavy chain and both light chain clones were found to be identical over their entire length, confirming that no errors had been introduced during the amplification process. The sequence of the anti-CD4 heavy and light chains are shown in FIGS. 1 and 2.

Expression of Monkey/Human Chimeric Anti-CD4

The expression vector TCAE 5.2 and TCAE 6 are not only able to be used for stable integrated expression into the cell lines Sp2/0 and CHO but, because it includes the SV40 origin, is also able to be expressed transiently in the cell line COS. COS cell expression was performed as follows: COS cells were seeded one day before the transfection so that they would be 50–70w confluent the following day. Culture medium was removed and the cells washed twice with Transfection Buffer (TB—140 mM NaCl, 25 mM Tris, 5 mM KCl, 0.5 mM $Na_2HPO_4$ 1 mM $MgCl_2$, 1 mM $CaCl_2$). 30 μg of cesium chloride purified TCAE 6 plasmid containing the anti-CD4 monkey/human chimeric heavy and light immunoglobulin chains were mixed with 3 ml of DEAE dextran per dish (1 mg/ml in TB). The DNA was allowed to incubate with the cells for 1 hour at 37° C. DNA solution was removed and replaced with 3 ml of 20% glycerol for 1.5–2.5 minutes, after which the cells were twice washed with TB. Cells were incubated in 5 ml of fresh medium containing 100 μM chloroquine for 3–5 hours at 37° C., after which they were washed twice with medium and incubated with normal DMEM for 72 hours. Supernatant (100 μl) from the transfected COS cells was assayed at various dilutions for the presence of antibody by an ELISA-based technique. Goat anti-human lambda was used to coat 96 well assay plates and a peroxidase-labeled goat anti-human IgG as the detection antibody, under standard ELISA conditions. COS cells were found to produce between 10 and 40 ng/ml of monkey/human chimeric antibody. Larger volumes of supernatant were concentrated 10 fold and used in a direct binding RIA to CD4 positive SupT1 cells. The parental whole monkey antibody and an irrelevant human immunoglobulin were used as a positive and negative controls respectively. Also, the monkey anti-CD4 and the monkey/human chimeric anti-CD4 were used to inhibit the binding of a high affinity mouse anti-CD4 (1F3) antibody. These results demonstrated that the monkey/human recombinant antibody (ATCC No. 69030) not only binds to CD4 positive cells but is able to inhibit the binding of 1F3 to CD4 positive cells in approximately the same concentrations of wholly monkey antibody or 1F3 itself.

EXAMPLE 2

This example relates to the in vitro functional characterization of CE9.1, including its effects on T cell proliferation and IL-2 production in MLR, its Fc receptor and complement binding properties, and its capacity to mediate ADCC and CDC responses. In addition, the in vivo effects on CD4 receptor mediation and lymphoid subsets in peripheral blood were analyzed. The following were analyzed. The following materials and methods were used in this example. [Anderson et al, "In vitro and in vivo characterization of a primatized mAb to human CD4: mAb causes CD4 receptor modulation but not CD4 T cell depletion in chimpanzees".]

Materials and Methods

Molecular Construction and Expression of PRIMATIZED™ Anti-CD4

Variable region immunoglobulin genes were amplified by PCR and cloned from a heterohybridoma derived from a monkey immunized with sCD4, as previously described [Newman, R. A., et al, "Primatization of recombinant antibodies for immunotherapy of human disease: a macaque/human chimeric antibody against human CD4", *Biotechnology*, 10:1455 (1992)]. Heavy and light chain variable region genes were inserted into a cassette expression vector, TCAE 6, in a tandem fashion and expressed as an IgG1λ after stable integration into DHFR$^-$ CHO cells [Newman, supra]. Three rounds of amplification in increasing amounts of methotrexate allowed cell lines to be developed which expressed levels of antibody in excess of 750 μg/mL over 8 days. A production cell line was generated that was grown in suspension culture and progressively expanded before inoculation of a hollow fiber reactor [Evans et al, "Large-scale production of murine monoclonal antibodies using hollow fiber bioreactors", *BioTechniques* 6(8):762 (1988)].

The mAb CE9.1, was purified by passing culture supernatant from the reactor through a Prosep A column (300 ml, Bioprocessing Inc.), previously equilibrated with phosphate buffered saline pH 7.2, at a rate of 125 ml/min. The column was washed with PBS until a baseline was established and bound antibody eluted with 5 column volumes of 0.2M acetic acid/0.1 M glycine buffer pH 4.0. Recovery was around 90%. The eluate was brought to pH 5.5 and passed through a Q-Sepharose column (Pharmacia). CE9.1 bound to the column which was washed with 25 MM Tris-HCl, pH 8.5. Antibody was eluted with 50 mM Tris-HCl, pH 6.5 containing 100 mM NaCl and concentrated by defiltration (Millipore Pellicon) against USP injectable normal saline. CE9.1 was finally filtered through a 0.04 um Nylon$_{66}$ NDP filter (Pall Filtration).

Binding Specificity: Binding of CE9.1 to CD4$^+$ SupT-18 cell

Ninety-six well U-bottomed microliter plates (Corning) were preblocked for 1 hr. on ice with PBS containing 0.2% bovine serum albumin and 0.1% sodium azide. SupT-18 cells (1×10$^5$), prewashed with the same buffer, were incubated for 30 min. on ice with varying concentrations of CE9.1 (2.4 pg/mL–10 μg/mL). Cells were washed twice and incubated for 30 min. on ice with a second layer antibody (FITC-labeled goat anti-mouse Ig). Cells were washed twice, resuspended in fixation buffer (2% formaldehyde in PBS) and analyzed using a FACScan flow cytometer (Becton Dickinson).

Binding Specificity: Analysis by flow of binding of CE9.1 to human peripheral blood leucocytes Mononuclear cells were isolated from human peripheral blood using the standard Ficoll/Hypaque centrifugation technique [Boyum, A., "Separation of blood leukocytes, granulocytes and lymphocytes", *Tissue Antigens* 4:269 (1974)]. The interface layer containing peripheral blood mononuclear cells (PMNC) were removed, washed with Hank's balanced salt solution (HBSS) and counted. 5×10$^6$ cells were incubated with 20 μl of CE9.1 (25 μg/mL), for 30 min. at 4° C. Cells were then washed with HBSS and incubated with 20 μl goat anti-human IGG-FITC (Fisher Scientific). After incubation on ice for an additional 30 minutes, cells were analyzed on a Becton Dickinson FACScan instrument using auto compensation and pre-calibration with Calibrite beads. Viable lymphocyte populations were identified by forward vs. right angle light scatter and the total lymphocyte population isolated by gating out all other events. Subsequent fluorescent measurements reflected only gated lymphocyte events. mAbs used for quantification of doubly stained cells and subsequent studies on chimpanzee blood included, anti-human CD3 (Leu-4-FITC; Becton Dickinson); fluorescein-conjugated anti-human CDS (Leu-2a-FITC; Becton Dickinson); phycoerythrin-conjugated anti-human CDS (Leu-2a-PE; Becton Dickinson); phycoerythrin-conjugated anti-human CD20 (Leu-16-PE; Becton Dickinson); fluorescein-conjugated goat antihuman IgG F(ab')2 (Cappel); and phycoerythrin-conjugated murine anti-CD4 (OKT4; Ortho Pharmaceuticals).

Human Tissue Cross-Reactivity

CE9.1 was evaluated for cross-reactivity on normal human tissues. Biotinylated CE9.1 was tested on cryostat-cut frozen sections from 32 different tissues using the avidin-biotin immunoperoxidase technique [Wilchek, M. et al, "The avidin-biotin complex in bioanalytical applications", *Anal. Biochem.*, 171:1 (1983)]. SupT1 cells (CD4$^+$) were used as the positive control and SB cells (CD4$^-$) as a negative control cell line. An irrelevant biotinylated mouse/human (IgG1) chimeric antibody was used as the negative antibody control.

For most tissues, three separate specimens were examined and reactivity with CE9.1 scored on a scale from 0 to 3$^+$. In some tissues different structures within the tissue were scored separately. For example, in the liver, hepatocytes, bile ducts and Kupffer cells were scored independently.

Species Specificity

Peripheral blood from several common laboratory primates and non-primates was screened with CE9.1 for identification of possible cross reactivity of CD4 positive T cells. The group included chimpanzees, baboons, rhesus, cynomolgus and pig tail macaques rats, mice, rabbits and dogs. Blood cells were isolated from 1–5 mL of whole blood by centrifugation (1500 rpm for 5 min) at 4° C. and washed by resuspension in equal volumes of PBS. The process was repeated once more and the cells resuspended in equal volumes of fetal bovine serum. Two-hundred microliters of the cell suspension from each species was placed into a 15 mL conical centrifuge tube with 20 μl of CE9.1 (25 mg/mL). The antibody and cells were mixed, placed on ice for 30 minutes then washed thoroughly with HBSS. 20 μl of goat anti-human IgG-FITC (Fisher Scientific) were then added and the samples mixed. After incubation on ice for an additional 30 minutes, samples were removed from ice and 10 mL of lysis buffer (0.01 M potassium bicarbonate, pH 7.4, containing 0.16 M ammonium chloride and 0.1 M sodium EDTA), prewarmed to 37° C., was added. Samples were incubated at room temperature for 15 min. followed by centrifugation at 1500 rpm for 5 min. Labeled cell pellets were washed two additional times in HBSS (pH 7.4) containing 1% bovine serum albumin and 0.05% sodium azide. The labeled cells were fixed by resuspending in fixation buffer (0.5 M sodium chloride containing 1.0%. formaldehyde; filtered through a 0.22 um filter). Samples were analyzed on a Becton Dickinson FACScan instrument, as above.

In Vitro Functional Assays: One way and three way mixed lymphocyte reaction

Human or chimpanzee T cells (1.3×10$^5$) were cultured with or without CE9.1 in flat bottomed microwells for seven days with mitomycin C-treated PBMCs (6.0×10$^4$) obtained from an unrelated donor of human or chimpanzee origin respectively. 1 uCi/well of tritiated thymidine was added to the culture during the last 18 hrs of culture. Microtiter plates were centrifuged, the cell pellets washed with HBSS and then counted in a liquid scintillation counter. Each sample was assayed in triplicate.

Human MLRs were conducted using three separate, unrelated donors as stimulator and responder mixes. This protocol was adopted to maximize the chances of a good response in the HLA-uncharacterized random samples of red cross buffy coat blood. In this protocol, none of the donor blood was treated with mitomycin C or irradiated.

THP-1 cell adhesion assay to measure Fc receptor binding activity of CE9.1

This assay depends on the bridging of two cell lines, one expressing CD4 and the other Fc receptors, by an anti-CD4 antibody. The CD4 expressing partner used was the adherent murine fibroblast cell line DAP which had been transfected with human CD4 (DAP/CD4). The Fc receptor bearing cells were THP-1. DAP/CD4 cells were placed in 96 well flat bottom plates (100 ul/well; 25,000 cells/well) and allowed to adhere overnight. THP-1 cells were resuspended in 50 mL of RPMI medium ($1\times10^6$ cells/mL) and induced for 24 hrs. at 37° C. by the addition of 50 U/mL of γIFN.

γIFN-induced THP-1 cells were loaded with calcine acetomethoxy ester (CAM, Molecular Probes) as follows; cells were washed with loading buffer (Dulbecco's PBS with Calcium and Magnesium and 0.1% bovine serum albumin) and resuspended at $5\times10^6$ cells/mL in 10 mL of the same buffer. CAM (1 mg/mL in DMSO) was diluted (1:50) with loading buffer and added to THP-1 cell suspensions 1:1 v/v. After incubation for 20 min. at room temperature, 25 mL of fresh loading buffer was added to each 4 mL of cell/CAM mixture and incubated a further 40 min. at room temperature. Cells were then washed twice with loading buffer and resuspended at $8\times10^6$ cells/mL. Serial dilutions of CE9.1 in PBS (without calcium, magnesium or BSA) were added to wells containing CD4$^+$ DAP cells and incubated for 5 minutes at room temperature. 50 ul of CAM loaded THP-1 cell suspension was then added and the plates incubated at room temperature for 1 hr. in the dark. Control wells without DAP cells were also assayed. After incubation wells were washed 3 times with PBS. After the final wash, 100 ul PBS was added per well, followed by 10 ul of 20% Triton X-100. After placing on a shaker for 10–15 seconds, plates were read in a Fluoroscan (MTX Lab systems Inc.).

Activated monocyte binding assay to measure Fc receptor binding activity of CE9.1

The Fc receptor assay was set up as described for THP-1 cells above except for the following differences. Monocytes were prepared from fresh human peripheral blood by standard Ficoll/hypaque and Percoll gradient separation. Monocytes were stimulated with γIFN, as above, but for 48 hrs. Plates were coated with stimulated monocytes for 24 hrs. and, in this assay, the CD4$^+$ line supT-18 was loaded with CAM, described above. SupT-18 cells were then added to the plates coated with stimulated monocytes as described above. The main difference in this assay is the CD4$^+$ cell line CAM loaded and added to the FcR bearing cell on the plate. In the above assay using THP-1 cells, the order was reversed.

Binding to FcγRII transfected murine fibroblasts

A murine fibroblast cell line (CDW32-L), which had been transfected with human FCRH, was obtained from the ATCC. Direct binding of CE9.1 was determined by incubating the antibody in the presence and absence of sCD4. Binding of CE9.1 was detected by incubation with goat anti-human Ig-antibodies conjugated to horseradish peroxidase (Southern Biotech). Fab fragments of CE9.1 were generated by enzymatic digestion and used as negative controls. Absorbance values obtained from CE9.1 (and Fab fragments) preincubated with cells in the presence of sCD4 were subtracted from absorbances obtained for the antibodies in absence of sCD4.

ADCC Assay (lysis of supT1 cells)

Fresh heparinized human blood samples were collected and PMNCs isolated by standard centrifugation procedures on Ficoll/Hypaque. Red blood cells in the buffy coat were lysed with ammonium chloride buffer and the cells were washed twice in Hank's Balanced Salt Solution. Peripheral blood lymphocytes (PBLs) were stimulated with 10 units of IL-2 per mL of RPMI/10% fetal calf serum (FCS) for 24 hours at 37° C., 5% $CO_2$. After 24 hours, the PBLs were resuspended in RPMI/5% FCS.

SupT1–18 cells ($1\times10^6$) were labeled by incubating with 100 uCi $^{51}$Cr for 1 hour at 37° C., 5% $CO_2$. The cells were washed twice with RPMI/5% FCS and $1\times10^4$ cells were added to each well. Three lots of CE9.1 antibody were serially diluted 1:2 with RPMI/5% FCS and aliquots added in triplicate to the SUPT1–18 containing wells for 30 minutes at 37° C., 5% $CO_2$. 100 uL of 1% Triton X-100 and 100 uL of media was used as maximal and spontaneous release controls respectively. The IL-2 stimulated PBLs ($8\times10^5$ cells) were added to the wells. The plates were centrifuged for 3 minutes at 900 rpm and incubated for 16 hours at 37° C., 5% $CO_2$. The supernatant from each well was collected and the amount of radioactivity counted in a gamma counter. The assay was performed in triplicate. Percent cell lysis was determined using the following formula:

$$\% \text{ Lysis} = \frac{(\text{Sample count} - \text{Spontaneous})}{\text{Maximal} - \text{Spontaneous}} \times 100$$

C1q binding assay

The C1q assay was performed using the SupT1–18 CD4 positive cell line in a suspension of $4\times10^6$ per mL. CE9.1 and control affinity purified monkey anti-CD4 antibody (50 ul) at equivalent concentrations of 20 ug/mL were added to $2\times10^5$ CD4 positive target cells. The cell suspension and antibodies were incubated for 1 hour on ice then washed twice with 1% BSA in PBS. Fifty uL of human C1q (10 ug/mL) was added to each tube and incubated 1 hour on ice. Each tube was washed twice, then incubated (1 hour, on ice, in the dark) with a 1:15 dilution of rabbit anti-human C1q FITC (50 uL). Cells were washed again twice and fixed in 0.5 mL of 1% formaldehyde/PBS. The cells were analyzed on a Becton Dickinson FACScan flow cytometer using Consort 30 software for data acquisition and analysis.

Complement mediated cytotoxicity assay

SupT1–18 cells ($1\times10^6$) were labeled by incubating with 100 uCi $^{51}$Cr for 1 hour at 37° C., 5% $CO_2$. The cells were washed twice with RPMI/5% FCS and $1\times10^4$ cells were added to each well. CE9.1 and control anti-CD4 antibodies were serially diluted 1:2 with RPMI/5% FCS and 50 ul aliquots added in triplicate to the SUPT1–18 containing wells. 100 uL of 1% Triton X-100 or 100 uL of media were added to wells to measure maximal and spontaneous release of $^{51}$Cr respectively. Following a 90 minute incubation at 37° C., 5% $CO_2$, a 1:5 dilution of rabbit complement (Cappel) was added to the wells. The plates were incubated another 90 minutes at 37° C., 5% $CO_2$ and then centrifuged for 3 minutes at 900 rpm. The supernatant from each well was collected and the amount of radioactivity counted on a gamma counter. The assay was performed in triplicate. Percent cell lysis was determined using the following formula:

$$\% \text{ Lysis} = \frac{(\text{Sample count} - \text{Spontaneous})}{\text{Maximal} - \text{Spontaneous}} \times 100$$

In vivo studies in chimpanzees

Six chimpanzees were divided into three groups of two animals each: group I (saline control); group II (10.0 mg/kg CE9.1 antibody) and, group III (10.0 mg/kg CE9.1 antibody). Group II animals were retreated with 10 g/kg of CE9.1 after 30 days, providing their $CD4^+$ T cell counts had returned to 30% of baseline. Group III animals were retreated with 10.0 mg/kg after 30 days providing their $CD4^+$ T cell counts had returned to 70% of baseline. If these values were not achieved by day 30, the animals would be screened for $CD3^+$, $CD4^+$, and $CD8^+$ T cell values at biweekly intervals until the $CD4^+$ T cell values attained the respective target value for that group. At this time the animals would again receive 10.0 mg/Kg of CE9.1 antibody intravenously, up to a maximum of three doses.

Baseline determinations of the total white blood cell count, lymphocyte and granulocyte values, and of the $CD3^+$, $CD4^+$ and $CD8^+$ lymphocyte subpopulations were performed on day −6, on day 0 immediately prior to dosing and again at 24 hours and 14 days after dosing. Three treatment cycles each with 10 mg/kg doses were administered to the chimpanzees on this study.

Results

Binding specificity of mAb CE9.1

Affinity measurements by SPR for the binding of CE9.1 to soluble CD4 show a Kd of 1.0 nM (Brigham-Burke et al. North American BIAsymposium 1995 (in press)). No binding was seen to $CD4^-$ cell lines and inhibition studies demonstrated that binding to $CD4^+$ cells could be completely abolished by soluble CD4 in a stoichiometric manner.

To determine the specificity of CE9.1 reactivity, binding to freshly isolated human PBMCs was determined by dual color flow cytometry analysis. FIG. 9 shows that about ⅔ of the $CD3^+$ cells bind CE9.1. Within the lymphoid subpopulation, all cells which bound OKT4 were also positive for CE9.1, while $CD8^+$ cells were all negative. Some CD3-cells also showed reactivity with CE9.1, although the nature of this reactivity has not been clearly determined.

Immunohistochemical analysis was conducted to determine tissue reactivity of CE9.1, including 32 different normal human tissues of lymphoid and non-lymphoid origin. Non-lymphoidal tissue included the major organs, brain, heart, skeletal muscle skin, liver, kidney, glandular and reproductive tissues. Such analysis showed no cross reactivity to any tissue other than those of lymphoid origin including lymph nodes, spleen, tonsil and peripheral blood (data not shown). Staining, confined to lymphoid aggregates was also observed in large intestine, lung, esophagus and skin.

Inhibition of human MLR by CE9.1

The effect of CE9.1 on T cell responses was evaluated by human MLR, as IL-2 production or proliferative responses. CE9.1 blocked both proliferation and IL-2 production with $IC$_of 10–30 ng/ml, with about 80% inhibition at 60 ng/ml (FIG. 10).

Fc Receptor Binding Activity of CE9.1

CD4 and Fc receptor based cell—cell adhesion assays were developed to determine the reactivity of CE9.1 with Fc receptors on monocytic cells. In one assay configuration, monocytes were isolated from fresh PBMCs by percoll gradient centrifugation, seeded into microliter plates and stimulated with γIFN for 48 hours. After 48 hours, dye loaded CD4+SupT1 cells were added to the activated adherent monocytes in the presence or absence of CE9.1. In a second configuration of this adhesion assay, the monocytic, non-adherent cell line, THP-1 was stimulated with γIFN. After 24 hours, the activated THP-1 cells were loaded with a marker dye and added, in the presence or absence of CE9.1, to adherent, $CD4^+$, fibroblast transfectants which had previously (24 hours earlier) been plated into microliter plates. In both cases, cell-cell adhesion is dependent on binding of the mAb to CD4 on one cell and Fc receptors on the other cell.

Figure 10C:
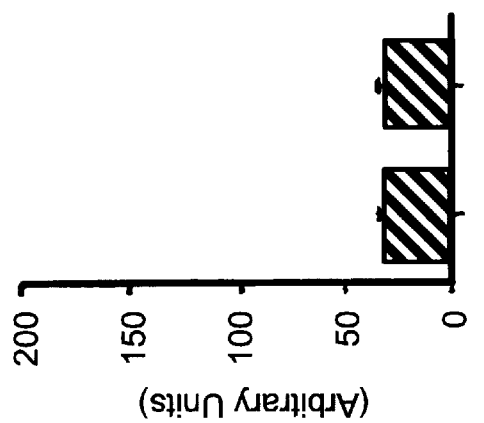
FIGS. 10a, 10b and 10c show a Fc receptor binding characteristics of CE9.1 where measurements show the agglutination of CD4$^+$flow cytomeric histogram of the binding fibroblasts with a) γIFN induced fresh monocytes, where a negative control utilized F(ab')2 fragments of CE9.1, b) fresh monocytes with or without γIFN induction, and c) in the presence of sCD4 or in the absence of antibody.
Figure 10B:
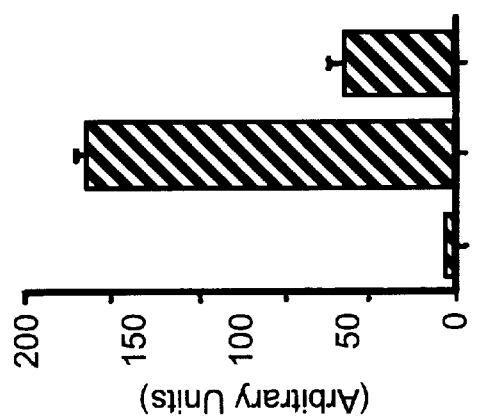
Figure 10A:
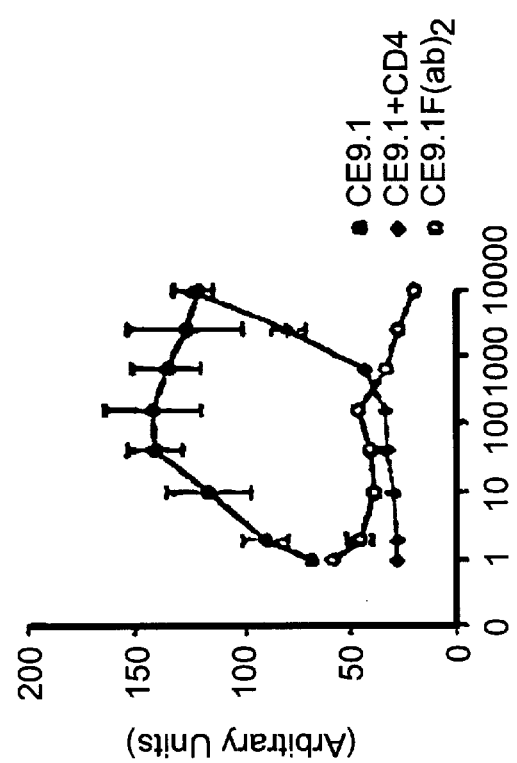
Figure 11:
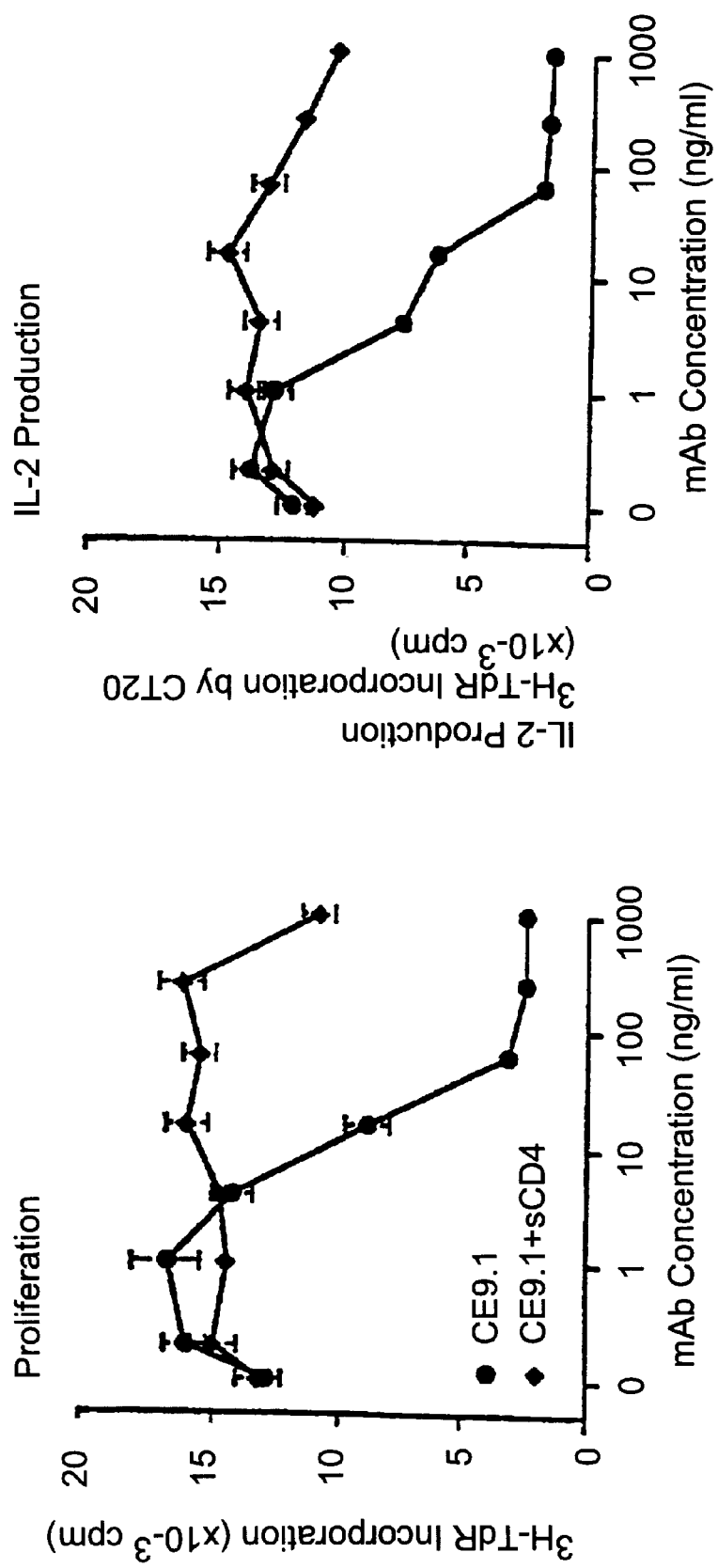
FIG. 11 shows inhibition of a human mixed lymphocyte reaction by CE9.1 where a) fresh human PBLs were used as responders and mitomycin C-treated stimulator cells from an unrelated donor were used for testing the inhibitory properties of a range of concentrations of CE9.1 and inhibition was measured by the amount of thymidine incorporation of IL-2 production, and b) MLR using chimpanzee responders and unrelated chimpanzee stimulators, where Leu3a, a murine anti-human CD4, was used as a control.

Data presented in FIGS. 10*a*, 10*b* and 10*c*, based γIFN activated fresh monocytes and the $CD4^+$ SupT1 T cells, shows CE9.1 mediates cell—cell adhesion in a dose dependent manner, with an approximate $ED_{50}$ of 20 ng/ml. Adhesion was completely blocked by sCD4, and could not be mediated by the F(ab')2 fragment of CE9.1. Monocytes not activated by γIFN were unable to bind CE9.1 9 (FIG. 10*b*). Similar data was also obtained with the assay based on the THP-1 and CD4+fibroblast assay (data now shown). Direct binding of CE9.1 to a murine fibroblast line transfected with human FCγRII receptors was also observed (data not shown).

Antibody Dependent Cell Mediated Cytotoxicity (ADCC)

Figure 12:
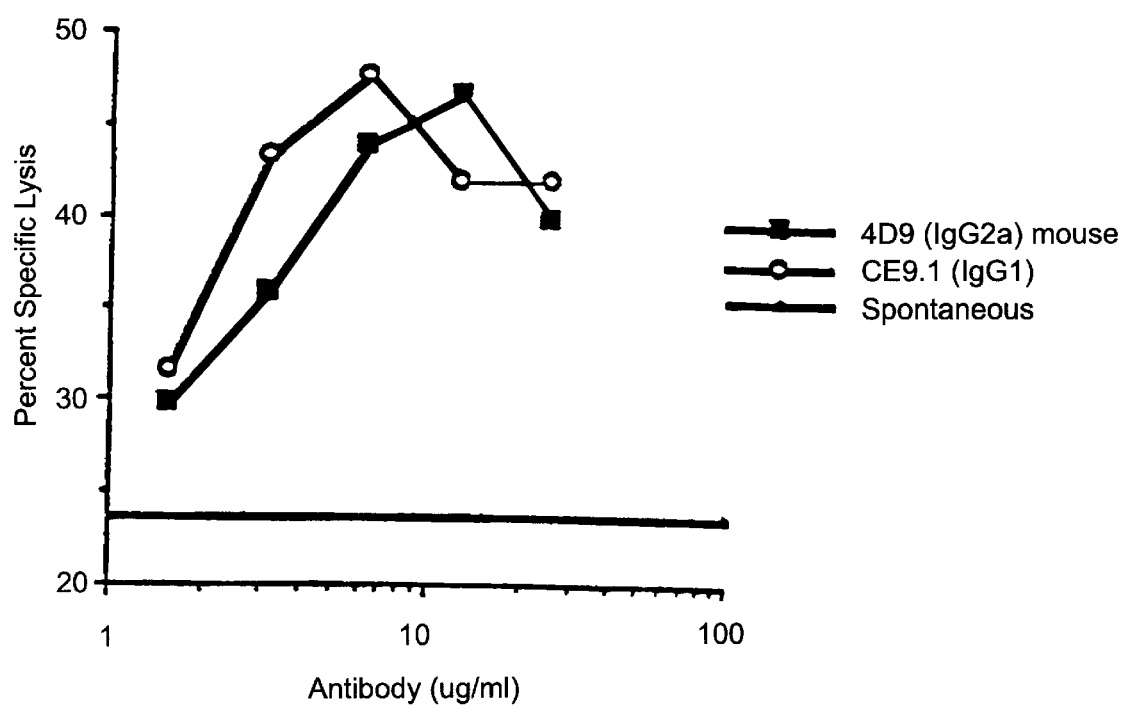

Radiolabeled SupT1 cells, used as targets in an ADCC assay were shown to be specifically lysed by effector cells in the presence of CE9.1. Maximal cytotoxicity was reached at approximately 6 ug/mL with a total specific lysis of around 50% (FIG. 12). As a positive control, a murine anti-CD4 of the IgG2a isotype (4D9) was used. This antibody behaved very similarly to CE9.1 giving the same level of total cell lysis. CE9.1 therefore was very effective in binding Fc receptors on effector cells and mediating the killing of $CD4^+$ target cell lines.

Complement fixation by CE9.1

Figure 13:
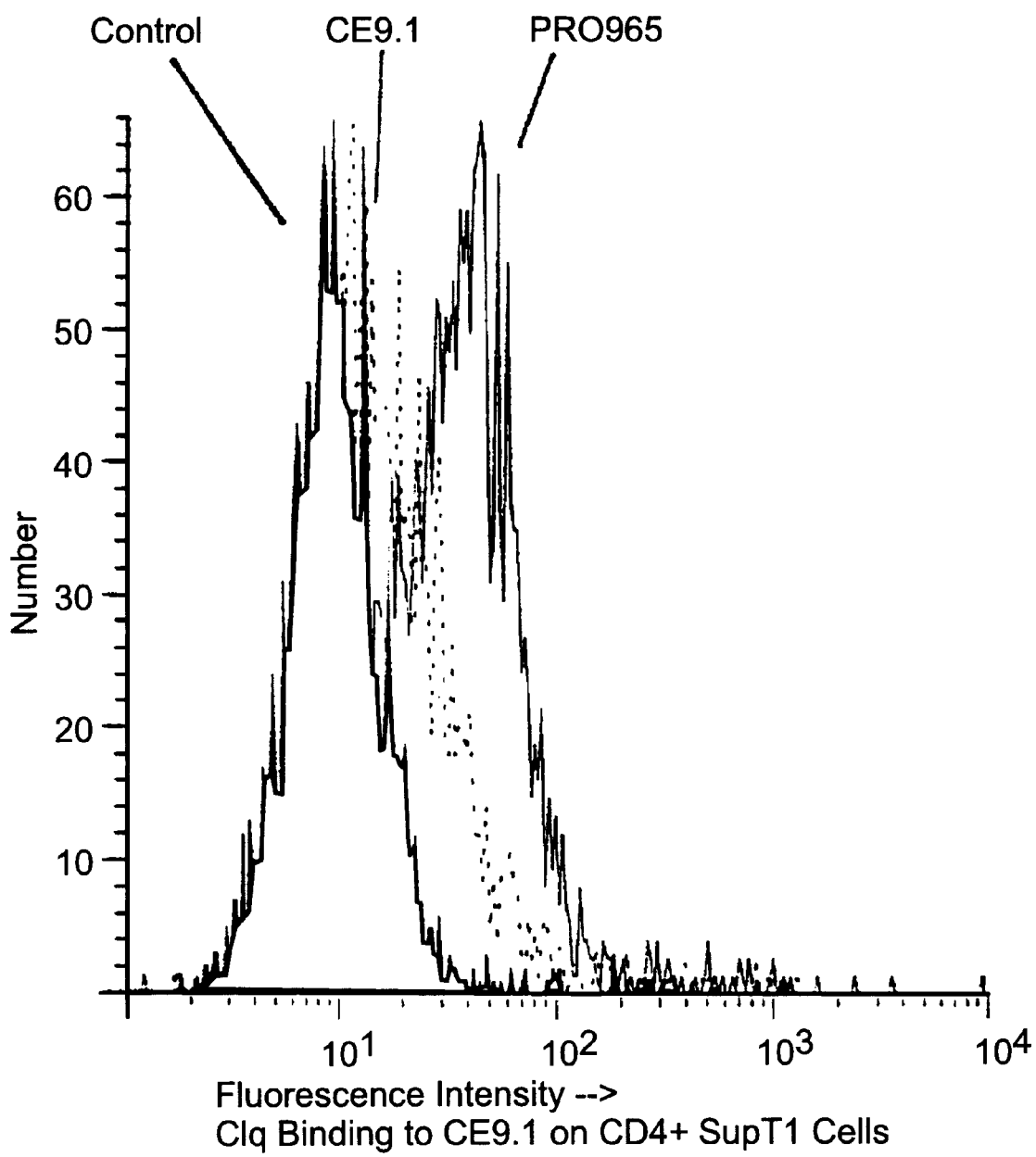
FIG. 13 shows a flow cytometric histogram of the binding of C1q to SupT1–18 cells in the presence and absence of CE9.1 where 10,000 events were recorded and the results expressed as a histogram, PRO945 are polyclonal antibodies from a monkey with high anti-CD4 serum titer, and the negative control was C1q plus anti-C1q in the absence of CE9.1.
Figure 14:
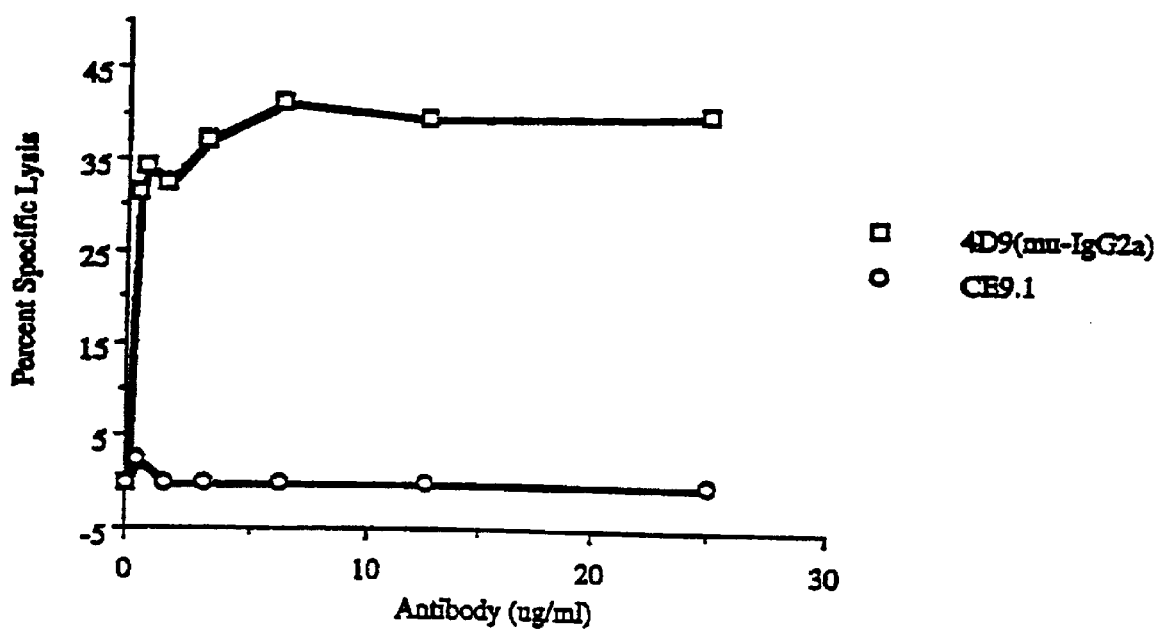
FIG. 14 shows the complement dependent cytotoxicity assay of CE9.1 where lysis of SupT-18 cells in the presence of CE9.1 and rabbit complement, where 4D9 is a murine anti-CD4 control of the subclass IgG2a which is able to fix complement, and where PRO965 is a polyclonal mixture of antibodies from the serum of a cynomolgus monkey with a high anti-CD4 titer.

Binding of C1q was measured by flow cytometry, as described above (Materials and Methods). As shown in FIG. 13, despite the fact that CE9.1 contained a human heavy chain constant region of the gamma 1 subtype, it showed only minimal binding of C1q (FIG. 13). Affinity purified monkey anti-CD4 serum antibodies were effective in mediating C1q binding, suggesting that the lack of C1q binding by CE9.1 is a property specific to this antibody. The lack of C1q binding by CE9.1 is reflected in the inability to fix complement (FIG. 14). Affinity purified anti-CD4 antibodies from monkey serum and a murine monoclonal IgG2a both produce significant lysis over the same concentration range.

CE9.1 species cross reactivity

Flow cytometry analysis of lymphocytes from different species showed that only chimpanzee and human cells bound CE9.1 strongly. Baboon was the only other species to show a weak reactivity with CE9.1 (10-fold lower than human). Human and chimpanzee lymphocytes reacted equally well with the mAb (Table 2). This was reflected in a comparable inhibition of T cell proliferation and IL-2 production in chimpanzee MLR by CE9.1 antibody (data not shown).

TABLE 2

| Species | Reactivity |
| --- | --- |
| Human | +++ |
| Chimp | +++ |
| Baboon | + |
| Rhesus | − |
| Cynomolgus | − |

| Species | Reactivity |
| --- | --- |
| Pigtail macaque | − |
| Dog | − |
| Rabbit | − |
| Rat | − |
| Mouse | − |

In vivo study in 6 chimpanzees

Figure 15:
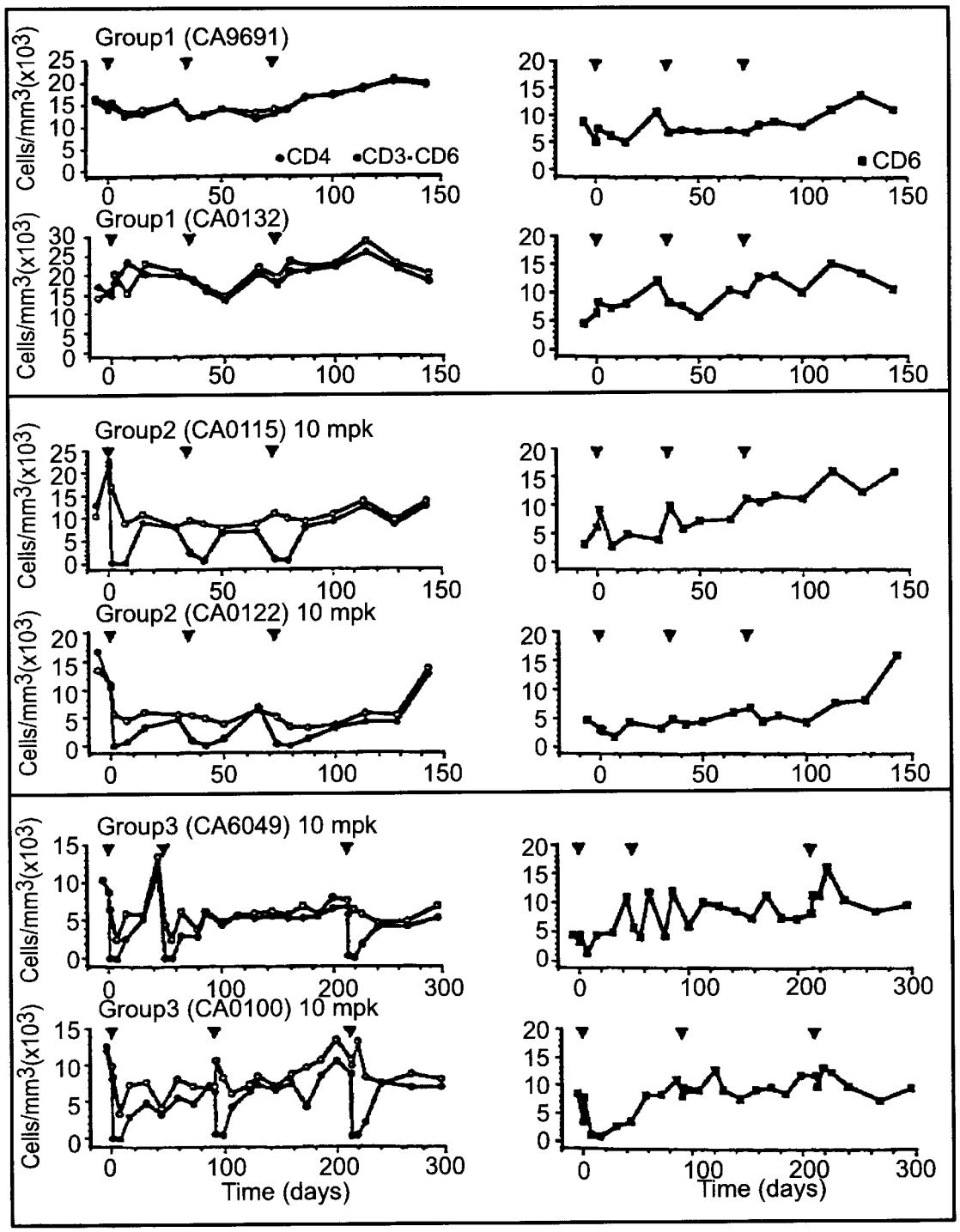
FIG. 15 shows high dose pharmacological study in six chimpanzees, where CD4, CD8 levels in peripheral blood expressed over a period of 150–300 days, CD3–CD8 curves indicating the number of CD4 modulated cells are also shown; top panel: Group 1—chimpanzees counts monitored. Arrows indicate CE9.1 doses. (2) saline control group, Middle Panel: Group 2—chimpanzees (2) receiving 10 mg/kg CE9.1. Dosing was repeated when CD4 counts returned to within 30% of baseline. Lower Panel: Group 3—chimpanzees (2) receiving 10 mg/kg CE9.1. Dosing was repeated when CD4 counts returned to within 70% of baseline.

Based on the lack of depletion of CD4 cells in the escalating dose study in a single chimpanzee, a dose of 10 mg/kg was given to 4 chimpanzees (in addition 2 animals in a control group received saline). As described in the Materials and Methods, the two dose groups were each given 10 mg/kg on day 0 of the study. FIG. 15 summarizes the effects on CD4 and CD8 counts in these animals. It can be seen that there was a decrease in cells expressing the CD4 receptor immediately following antibody administration. The reduction in CD4 counts was only seen immediately after each dose of antibody given. No similar change in CD4 counts was seen in the saline control group. CD8 counts remained unaffected throughout the course of treatment although variability on a daily basis was observed (FIG. 15, left hand panel, open circles). By examining the $CD3^+$-$CD8^+$ population, less dramatic drops in CD4 numbers were observed. The data suggest the appearance of $CD3^+$ CD8-T cell populations which may be the result of CD4 antigen modulation. The exact mechanism of modulation is unclear at this stage, but may include internalization or shedding of CD4 molecules as a result of cross-linking by Fc receptors expressed on other lymphoid or monocytic cells. Comparison of the cell numbers in FIG. 15 show that some depletion of $CD4^+$ cells may be occurring although the major effect is due to CD4 receptor modulation. In most cases the modulatory effect appears to last for about 7–10 days directly following the administration of antibody, after which, CD4 expression returns to just below baseline levels.

The total CD4 counts remain depressed relative to the baseline time point by 10–50% but after cessation of treatment, return to the normal range. The chimpanzees were followed for a period of up to 150 days (groups 1 and 2) or 300 days (group 3). The group 2 animals' CD4 counts had returned to normal levels at 80 days post final treatment whereas the group three animals had returned to within 20% of baseline within the same time frame.

EXAMPLE 3

This example describes the genetic construction of the DNA expression vector used in mammalian cells to produce CE9γ4PE which is a macaque/human chimeric anti-CD4 antibody containing a human γ4 isotype incorporating the P and E changes.

Construction of DNA Expression Vector

Human gamma 4 heavy chain gene was isolated by PCR from the cell line TPIT10.4 (obtained from S. Morrison, UCLA) using the 5' IDEC primer # 479 and the 3' IDEC primer # 462 (see FIG. 16) which contained Nhe I and BamH I sites respectively. The entire cloned fragment of the human gamma 4 has been sequenced and found to be identical to that described in Kabat et al (NIH Publication Fifth Edition No. 91–3242, U.S. Dept. of Health and Human Services (1991)) (see FIG. 17). The Nhe I/BamH I fragment was cloned into an expression vector Anex 2. The entire light and heavy chain immunoglobulin genes from this plasmid were moved to another expression plasmid on a Bgl II to Sac I fragment. This plasmid was called anti-CD4 (G4,L,Oz-) in NEOSPLA3F.

PCR mutagenesis was used to change amino acids # 229 and 236 in the gamma 4 constant region. PCR was performed using a 5' primer GE212 (Midland) and the 3' IDEC primer # 698 containing Nhe I and BspH I restriction sites respectively (see FIG. 16), and the fragment was cloned into the anti-CD4(G4,L,Oz-) plasmid in a three part ligation and sequence plasmid was called anti-CD4 (G4(PE),L Oz-) in NEOSPLA3F.

EXAMPLE 4

Expression in Chinese Hamster Ovary (CHO) Cells

Integration of plasmid and selection for antibody producing clones

CHO cells (DG44) (Urlaub et al., *Som. Cell Mol. Genet.*, 16:555–566 (1986)) were grown in CHO-S-SFM II media containing (GIBCO/BRL, CHO media), 50 uM Hypoxanthine and 8 uM Thymidine (GIBCO/BRL, CHO media). This media is called CHO media plus HT.

Five electroporations were performed with $4 \times 10^6$ cells and 5 ug of plasmid DNA [Anti-CD4(γ4(PE), Lambda, OZ-) in NEOSPLA3F] using a BTX 600 electroporation device (BTX, San Diego, Calif.) in 0.4 ml disposable cuvettes. Prior to electroporation the plasmid had been restricted with Pac I which separates the genes expressed in mammalian cells the portion of the plasmid used to grow the plasmid in bacteria. Conditions for electroporation were 230 volts, 400 microfaradays, 13 ohms. Each electroporation was plated into a single 96 well dish (about 40,000 cells/well). Dishes were fed with CHO media+HT containing G418 (Geneticin, GIBCO), at 400 ug/ml active compound, two days following electroporation, and thereafter as needed until colonies arose. Supernatant from confluent colonies was assayed for the presence of chimeric immunoglobulin by an ELISA specific for human antibody. Twenty eight G418 resistant colonies arose on five plates (out of 480 wells). The G418 resistant colony expressing the most antibody, clone, 5C1 was confluent 30 days after electroporation. Southern blot analysis shows that clone 5C1 is a single copy integrant (data not shown). In a four day culture seeded at $10^5$ cells/ml in a 125 ml spinner, this clone doubled every 28 hours, and had an antibody production rate of 0.5 pg/cell/day (0.9 mg/L).

Amplification

Clone 5C1 was scaled up and plated at various concentrations from $10^6$ cells/plate to $3 \times 10^4$ cells/plate into 96 well dishes containing CHO media+5 nM Methotrexate (MTX, Sigma (+) Amethopterin). Twenty days later clone 5C1-5B9 became confluent on the $3 \times 10^5$ cells/plate (49 of the 96 wells grew on this plate). This clone was scaled up. In a four day culture seeded at $10^5$ cells/ml in a T150, this clone doubled every 35.5 hours, and had an antibody reduction rate of 15.3 pg/cell/day (18 mg/L). Clone 5C1-5B9 was scaled up and plated at various concentrations from 100 cells/plate to $3 \times 10^4$ cells/plate into 96 well-dishes containing CHO media+50 nM Methotrexate. Thirty six days later clone 5C1-5B9 -50C1 became ~60% confluent on the $10^5$ cells/ plate (50 of the 96 wells grew on this plate). This clone was scaled up.

Cell Banks for Phase I Supplies of CE9γ4PE Parent Seed Stock (PSS)

A 50 nM MTX PSS of the clone 5C1-5B9-50Cl was frozen down. The cells were cultured in a 500 ml spinner containing CHO medium plus 50 nM MTX. At the time of the freezing, the culture had attained a density of $1.1 \times 10^6$ cells/ml with a 96-. viability and a doubling time of 29.3 hours. Antibody production was determined by a sandwich ELISA to be approximately 27 pg/cell/day. The cells were centrifuged out of the medium and vialed at a density of 2.0×10⁷ cells/ml in 95% JRH Biosciences Fetal Bovine Serum and 5% Sigma this common master mixture, 1 ml of freeze medium with cells was vials frozen. The vials were frozen at −70° C. and the following day placed in a liquid nitrogen tank.

One 50 nM MTX PSS vial was thawed and seeded into a 100 ml spinner containing CHO medium plus 50 nM MTX. Three days later this spinner was split into 2×125 ml spinners at 2×10⁵ cells/ml; one spinner containing CHO medium plus 50 nM MTX and the other CHO medium only.

Three days later 15 mls of the cells and medium from the CHO medium only spinner were frozen and sent to Tektagen for Points to Consider Mycoplasma testing. Production runs both with and without MTX were continued for eight weeks. Results from Tektagen showed Anti-CD4 (gamma 4(PE), Lambda, OZ-) NEOSPLA3F in CHO; clone 5C1-5B9-50C1 Parent Seed Stock to be Mycoplasma free. Ten vials of the of the 50 nM NM PSS were transferred for storage in liquid nitrogen.

Master Cell Bank (MCB)

Two 50 mM MTX PSS vials of clone 5C1-5B9-50C1 were thawed and seeded into a 100 mL spinner flask containing CHO medium, plus 50 nM MTX. The culture was expanded for six days into progressively larger spinner flasks until it had attained a volume of 2000 mL, with a density of 9.5×10⁵ and a viability of 98%. The cells were centrifuged out of the media and resuspended at a density of 2.0×10⁷ cells/ml in 95% JRH Biosciences Fetal Bovine Serum, and 5% Sigma Hybrimax DMSO. The cell suspension in freezing medium was aliquoted (10 mL) into each of 80 cryovials designed as MCB G4PE50-M-A. The vials were frozen at −70° C. Twenty four hours later the cell bank was transferred for storage in liquid nitrogen.

EXAMPLE 5

Stability of CD4 mAbs

Figure 18:
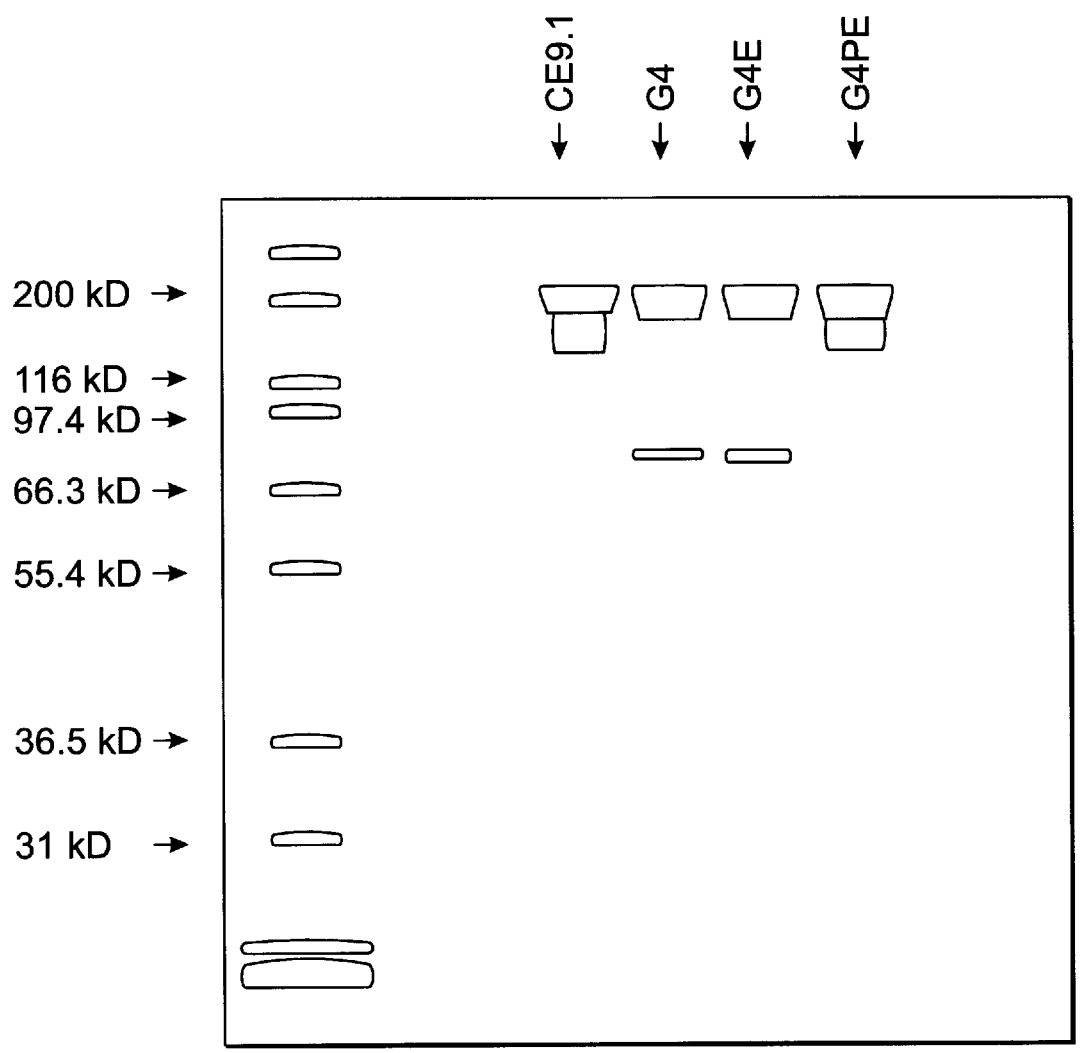
FIG. 18 depicts non-reducing SDS-polyacrylamide gel electrophoresis of CE9.1, CE9γ4(G4), CE9γ4E(G4E) and CE9γPE(G4PE). Halfmer molecule is seen at a molecular weight of approximately 80 kD.

The physical and chemical stability of CE9γ4PE and CE9γ4E solutions are monitored over 3 months at 5°, 40° C., and diffused light by SDS-PAGE (reduced and non-reduced), IEF, reverse phase-HPLC, size exclusion chromatography (SEC), and ELISA. Initial testing by RP-HPLC and non-reduced SDS-PAGE suggests that CE9γ4E is composed of two major species namely, the non-reduced whole molecule and a non-covalently associated molecule which, under the conditions of the analysis, breaks apart into two equal units labeled "halfmers". Interestingly, no major differences in bio-analytical profiles of these two mAbs were observed by SEC, IEF, SDS-PAGE (reduced) and ELISA. The amounts of "halfmer" in CE9γ4PE are less than 1% by either RP-HPLC or SDS-PAGE (non-reduced). FIG. 18 shows the SDS-PAGE (non-reduced) analysis of monomer and "halfmer" in solutions of CE9γ4PE and CE9γ4E. The amount of "halfmer" in CE9γ4E remained constant relative to initial testing over the three months at any of the conditions tested. "Halfmer" content in CE9γ4PE remained under 2% at all time conditions tested. No major differences in stability between CE9γ4E and CE9γ4PE were observed at 5° and 40° C.). CE9γ4E solution stored under diffused light is slightly less stable than CE9γ4PE. The data suggests that the "halfmer" in CE9γ4E does not have a significant effect on the overall stability of the whole molecule. No major differences in the physical stability of CE9γ4PE and CE9γ4E solutions were observed.

Affinity and Stoichiometry of CD4 mAbs by Surface Plasmon Resonance

Figure 19:
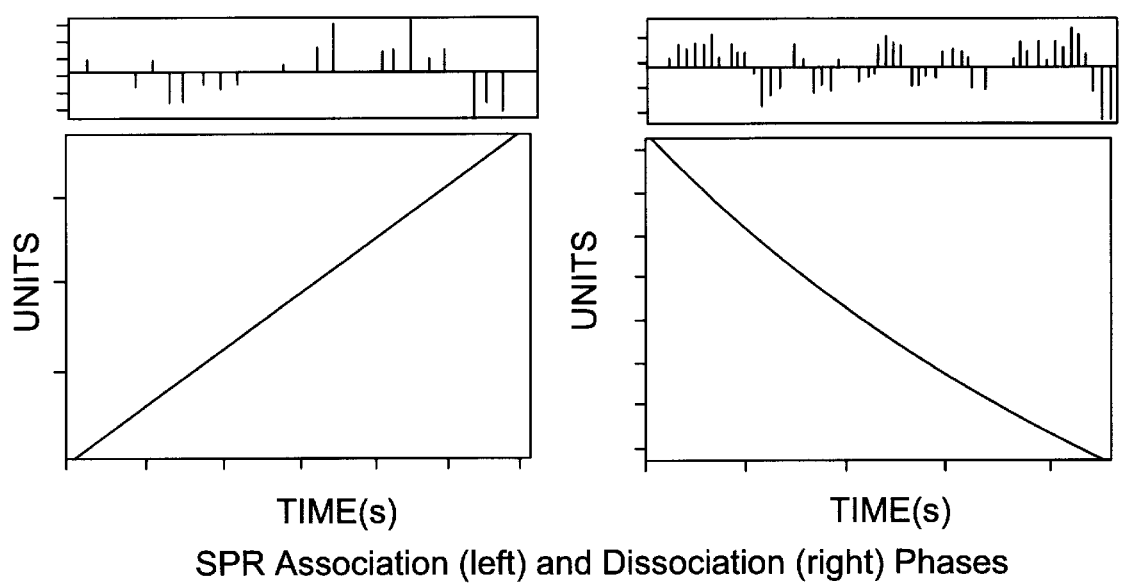
FIG. 19 contains data for the association and dissociation phases of the SPR progress curves.

The stoichiometry of binding of soluble CD4 to immobilized mAbs can be determined by saturation binding experiments on BIAcore (Pharmacia). Data for the association and dissociation phases of the SPR progress (FIG. 19) were analyzed directly using the integrated form of the rate equations as described in O'Shannessey et al., *Anal. Biochem.*, 212:467–468 (1993). A summary of the binding data, expressed as moles CD4/mole mAb is presented in Table 3. It can be seen from this data that in all cases, the stoichiometry of binding is greater than 1.5:1. Given that BIAcore is a solid phase interaction system and that the immobilization protocol is random, these results suggest that both antigen binding sites of each mAb are functional. Thus, the stoichiometry of CD4 binding was the same for all mAbs and close to the theoretical value of 2.0. Furthermore, affinity measurements show the affinity to be the same for all mAb complexes, namely approximately 1.0 nM.

TABLE 3

Stoichiometry and Affinity of Binding Measured by Surface Plasmon Resonance

| Antibody | BIAcore Stoichiometry | Affinity (nM 25° C.) |
|---|---|---|
| CE9.1 | 1.56 | 0.99 |
| CE9γ4 | 1.61 | 1.34 |
| CE9γ4E | 1.72 | 1.43 |
| CE9γ4λK | 1.67 | 1.08 |
| CE9γ4PE |  | 1.09 |

EXAMPLE 6

In Vitro Biological Evaluation of CE9γ4PE

Summary

CE9.1, CE9"4PE, and the other gamma 4 derivatives were compared for activity mediated by the Fab region (MLR) and the Fc domain (Fc receptor binding, ADCC, and CDC). Fab dependent activity (MLR) did not differ among the mAbs but they were distinguished in their Fc receptor binding properties. The unmodified gamma 4 derivative CE9γ4 showed surprisingly strong binding to Fc receptors, but the E mutation in CEγ4E and CE9γ4PE ablated this binding as well as ADCC activity.

Effect of mAbs on Mixed Lymphocyte Responses (MLR)

A three way mixed lymphocyte response (MLR) assay was performed to determine the effect of the mAb constructs on allo-antigen driven T cell proliferation and EL-2 production. MLRs are dependent on the presence CD4⁺ T cells, and a large proportion of the response is dependent on the participation of the CD4 receptor through its interaction with MHC Class II molecules on antigen presenting cells. The MLR response is an in vitro correlate of aspects of transplant rejection in vivo. In terms of other pharmacological agents, MLRs are also blocked by immunosuppressive agents such as cyclosporin A.

Figure 20:
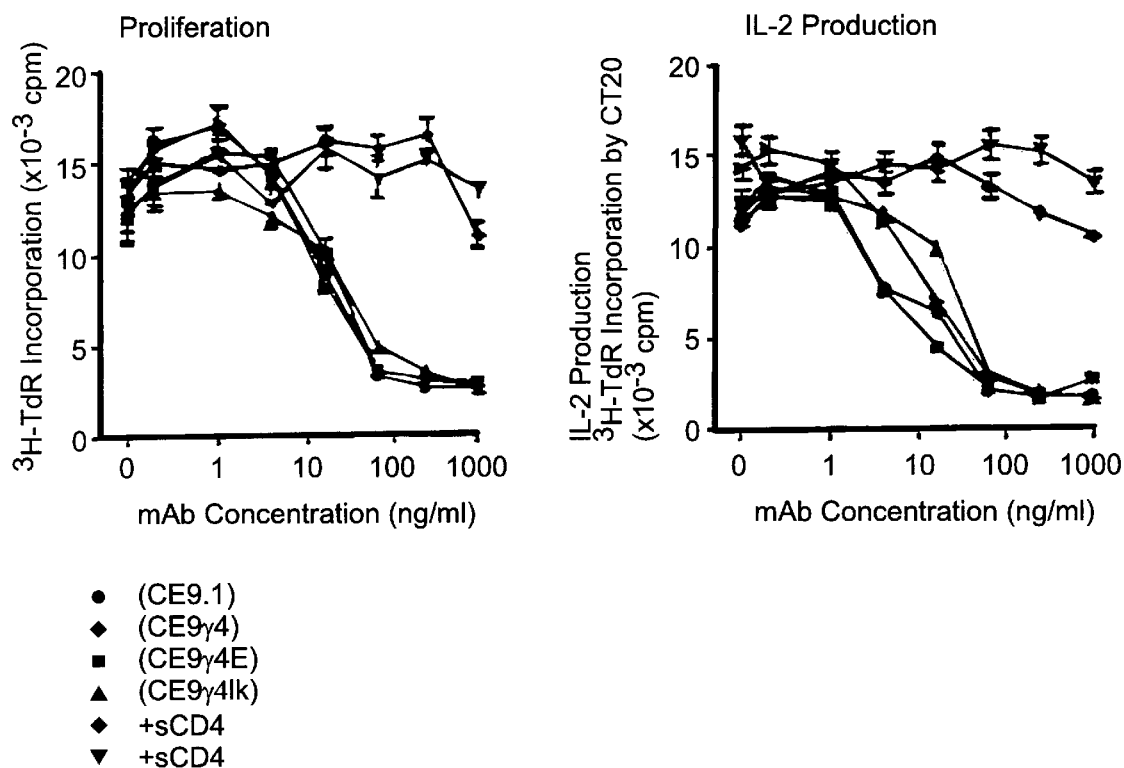
FIG. 20 shows the effect of CD4 mAb constructs in primary MLR.

All mAb constructs were equivalent in their ability to block MLR, read out both as proliferative response of T cells and IL-2 production (FIG. 20 and Table 4). Thus, grafting of V domains of CE9.1 onto human λ4 structures, and the "P & E" substitutions in the hinge and CH2 domains did not affect the ability of the mAbs to block CD4-dependent T cell responses in vitro.

TABLE 4

Effect of mAbs on MLR - Summary

| Antibody | Proliferation (IC50) | IL-2 Production (IC50) |
|---|---|---|
| CE9.1 | 20 ng/ml | 5 ng/ml |
| CE9γ4 | 20 ng/ml | 5 ng/ml |
| CE9γ4E | 20 ng/ml | 10 ng/ml |
| CE9γ4λK | 20 ng/ml | 20 ng/ml |
| CE9γ4PE | 20 ng/ml | ND |

Conclusion

All mAbs are equivalent in the inhibition of MLR.

Fc Receptor Binding Properties of mAbs

Validation of Assay for Determination of Fc Receptor Binding

CE9γ4PE was designed to be devoid of FcR binding activities. To measure this activity, an assay was developed based on FcR and CD4 mediated attachment of cells through bridging via mAbs. This assay measures the CD4 and FcR binding functions of mAbs simultaneously, as an in vitro correlate of FcR and mAb-mediated depletion of CD4 cells in vivo.

Figure 21:
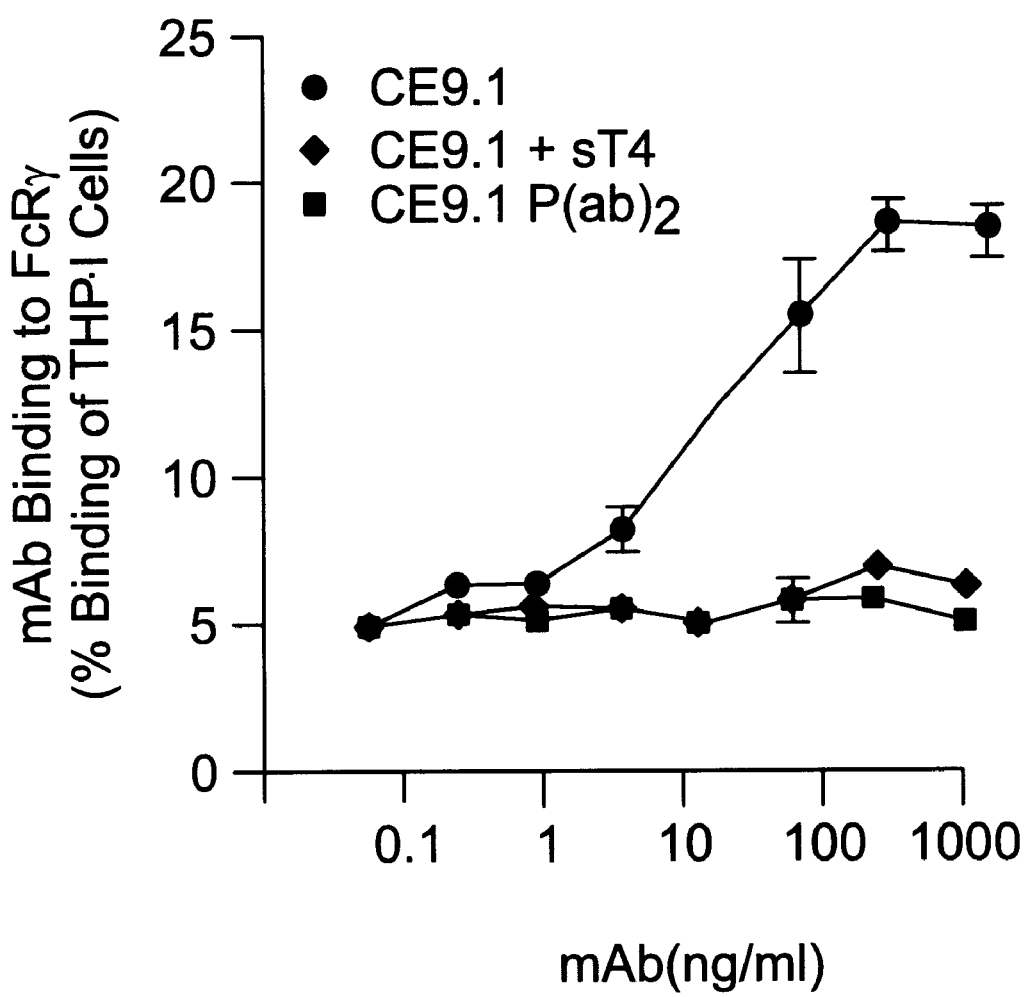
FIG. 21 shows the adhesion of IFN-T induced monocytic cell line THP-1 to CD4$^+$ fibroblast transfectants.

FIG. 21 demonstrates that CE9.1 facilitates adhesion of FcR-expressing monocytic cells (IFN-γ-induced THP-1 cells) to $CD4^+$ fibroblasts (CD4 transfected fibroblast cell line) in an adhesion assay. Binding is dependent on the Fc-domains of the mAb CE9.1, since the truncated F(ab')2 could not facilitate binding. Binding also requires the antigen recognition site of the CE9.1 because its occupation with sCD4 blocks cell-cell attachment.

Determination of Fc Receptor Binding Activities of mAbs mAbs CE9.1 (IgG1), CE9γ4 (IgG4), CE9γ4λK (IgG4 λK hybrid), CE9γ4E (IgG4, E mutant) and CE9γ4PE (IgG4, PE mutant) were evaluated for their ability to bind, simultaneously, cell surface CD4 and FcR.

Figure 22:
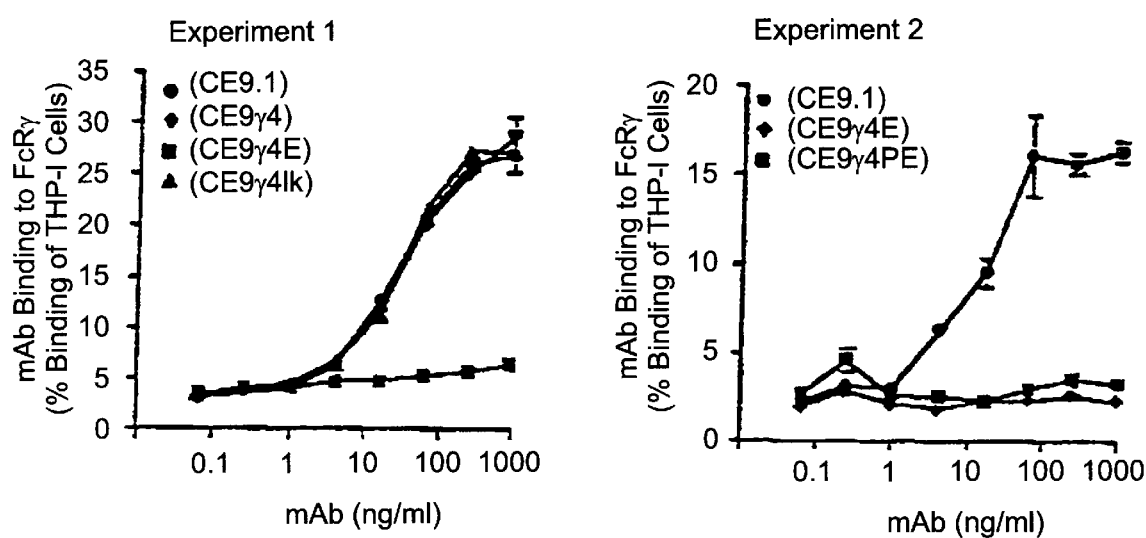
FIG. 22 depicts FcR and CD4$^-$ mediated adhesion of CE9.1, CE9γ4, CE9γ4E and CE9γ4γK.

As was hoped, CE9.1 had good binding activity in this assay. Surprisingly, the IgG4 constructs CE9γ4 and CE9γ4λK retained sufficient affinity for FcR that they were indistinguishable from CE9.1 in this assay. Activity in this assay was lost only when the "E" substitution was introduced as in CE9γ4E and CE9γ4PE (see FIG. 22).

In vitro C1q Binding Properties of CE9γ4PE

The complement system contains, among its various functional components, the ability to interact with certain types of antibodies in a manner which leads to cell lysis and destruction. Human IgG1 antibodies normally possess the capability to bind C1q and deplete target cells bearing surface antigens for which they have specificity. Other human isotypes such as IgG4 exhibit reduced ability to bind C1q and thus would be unable to deplete target cells. The engineering of CE9γ4PE in a gamma 4 construct would, in theory, achieve the objective of preventing complement fixation and allow the antibody to bind to CD4 target cells eliminating potential destructive side effects.

Figure 23:
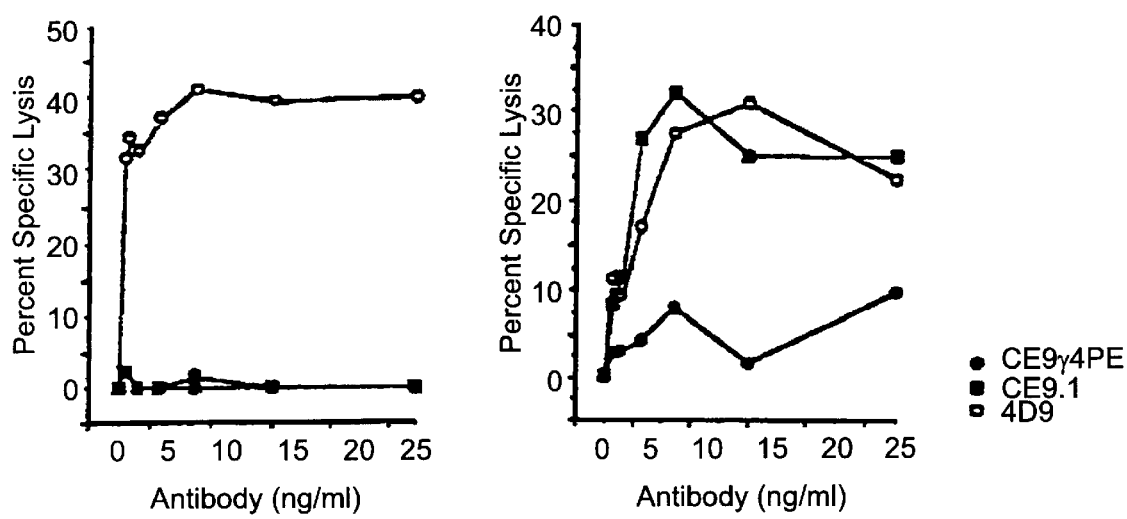
FIG. 23 shows CDC and ADCC results with CE9γ4PE, CE9.1 and a murine fixing mAb to HuCD4.

Comparison of CDC effector properties of CE9γ4PE and CE9.1 were accomplished using the classical method of complement mediated cytolysis of chromium labeled $CD4^+$ SupT1 cells in the presence of rabbit complement. In these studies, a murine complement fixing mAb to HuCD4, 4D9 (IgG2a), was used as a positive control. Both CE9.1 and CE9γ4PE were ineffective in fixing rabbit complement (FIG. 23). It was noted earlier that CE9.1 binds C1q poorly and thus unable to fix human complement. These results show that both constructs are unable to promote cell lysis through complement effector mechanisms.

In vitro ADCC Effector Properties of CE9γ4PE

Cells with cytotoxic potential that can bind mAbs via FcR can mediate ADCC directed to antibody-coated target cells. Human T helper cells expressing the CD4 molecule are recognized by mAb CE9.1 which triggers cytolytic attack by FcR-bearing killer cells, granulocytes and/or macrophages. The objective in the engineering of CE9γ4PE was to remove the ability of the mAb to bind to FcRs, which would eliminate the ability of accessory cells to mediate depletion of CD4 target cells, while still allowing the mAb to remain immunosuppressive.

Comparison of ADCC effector properties of CE9γ4PE and CE9.1 were accomplished using the classical method of cell-mediated cytolysis of chromium labeled $CD4^+$ SupT1 cells. The murine CD4 mAb 4D9 (IgG2a,K) was chosen as a positive control. Effector cells were human peripheral blood leukocytes obtained from a buffy coat. FIG. 12 shows the abilities of both mAbs 4D9 and CE9.1 to mediate specific lysis of $CD4^+$ cells. Under identical conditions, CE9γ4PE had very little effect.

These results show that CE9γ4PE is unable to mediate cell lysis through either FcR or complement mechanisms.

EXAMPLE 7

Comparative PK Analysis of CE9γ4E and CE9γ4PE

Comparative pharmacokinetics of two lead λ4 mAbs, CE9γ4E and CE9γ4PE, was investigated in male Sprague-Dawley rats. CE9γ4E or CE9γ4PE was administered as an iv bolus dose at 1 mg/kg (four animals per group), and blood samples were taken for 4 weeks post dose. Plasma CE9γ4E and CE9γ4PE concentrations were determined using a sCD4/anti-human IgG sandwich ELISA designed to confirm not only the presence of circulating human IgG, but also the ability to bind recombinant human soluble CD4.

Figure 24:
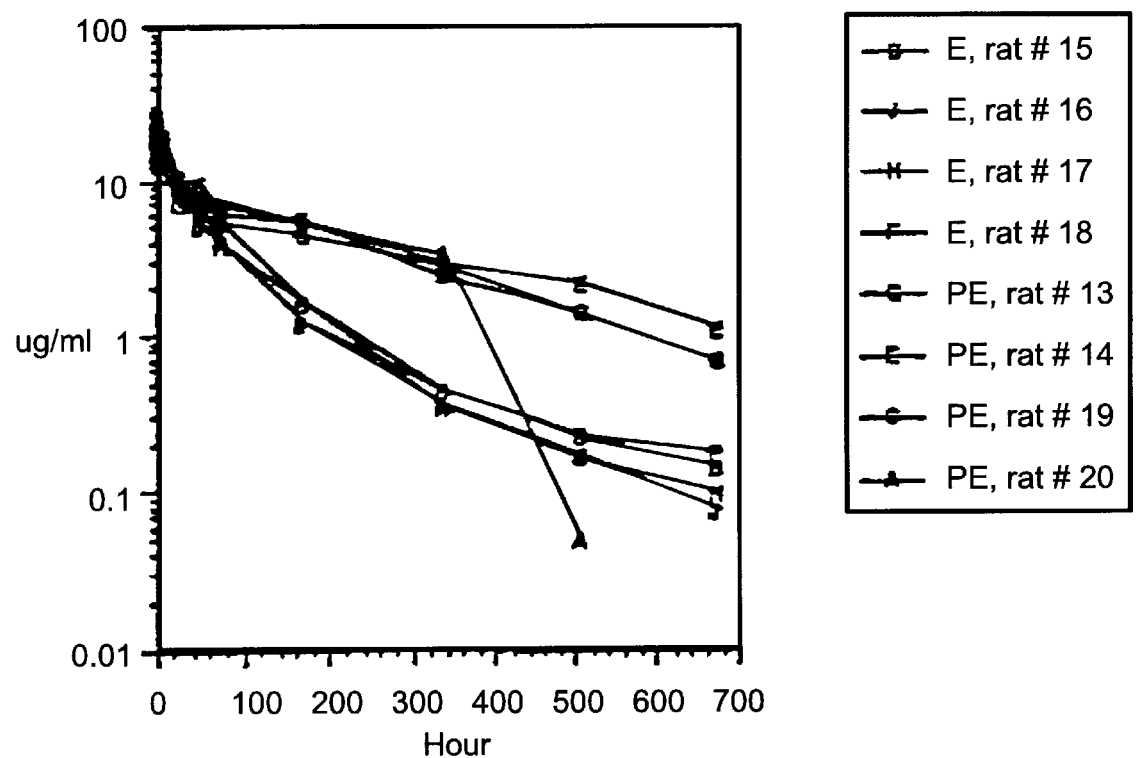
FIG. 24 shows plasma concentrations following 1 mg/kg in bolus of CE9γ4E and CE9γ4PE in mice Sprague-Dawley rats.

Following a 1 mg/kg intravenous bolus administration of CD4 mAb, CE9γ4E plasma concentrations declined in a triphasic manner, and CE9γ4PE plasma concentrations declined in a biphasic manner (FIG. 24). For comparative purposes, and due to an insufficient number of data points to adequately describe the terminal phase for CE9γ4E, all plasma concentration-time profiles were analyzed using a biphasic model. Small inter-subject variability was observed. The predominant secondary phase $t_{1/2}$ was approximately 4 days for CE9γ4E, and 9 days for CE9γ4PE, and accounted for 67% and 93%, respectively, of the total area under the plasma concentration-time curve. The apparent plasma clearance for CE9γ4PE was low (6.4 ml/hr/kg), and was approximately half the clearance of CE9γ4E (1.0 ml/hr/kg). Thus, the pharmacokinetic characteristics of the PE mutant γ4 mAb, CE9γ4PE, are similar to other humanized Ti mAbs in rats.

The long circulating half-life of functionally intact CE9γ4PE in the rat also suggests that CE9γ4PE is likely to be effective over an extended period of time when administered to man.

These results confirm that the PE mutant CE9γ4PE has a 2-fold lower plasma clearance and a longer half-life than CE9γE mutant in the rat.

TABLE 5

Pharmacokinetic parameters (Mean ± SD) of CE9γ4E
and CE9γ4PE following a 1 mg/kg iv bolus to make Sprague-Dawley rats

| CD4 mAb | CL (ml/hr/kg) | AUC$_{0\text{-inf}}$ (μg × (hr/ml) | MRT (hr) | T$_{½}^{-1}$ (hr) | T$_{½}^{-2}$ (hr) | % AUC$_2$ | V$_{SS}$ (ml/kg) |
|---|---|---|---|---|---|---|---|
| CE9γ4E  | 0.999 ± 137   | 1010 ± 130 | 109 ± 12   | 15.2 ± 3.8 | 97.7 ± 29.5 | 55.7 ± 14.2 | 109 ± 14 |
| CE9γ4E  | 1.32 ± 0.30   | 760 ± 138  | 79.5 ± 16.0 | 16.6 ± 6.9 | 95.3 ± 30.8 | 52.1 ± 20.0 | 103 ± 18 |
| CE9γ4PE | 0.410 ± 0.074 | 2500 ± 440 | 295 ± 43   | 9.9 ± 3.3  | 224 ± 33    | 93.4 ± 2.2  | 119 ± 16 |

Abbreviations of pharmacokinetic parameters: CL = total plasma clearance; AUC$_{0\text{-inf}}$ total area under the plasma concentration versus time curve; MRT = mean residence time; T$_{½}^{-1}$ = apparent half-life in the initial phase; T$_{½}^{-2}$ = apparent half-life in the secondary phase; % AUC$_2$ = percentage of the area under the plasma concentration versus time curve during the secondary phase; V$_{SS}$ = volume of distribution at steady state.

Based on these results, CE9γ4PE should be suitable for therapeutic use, e.g., by i.v. administration. Also, other routes of administration may also be suitable.

EXAMPLE 8

In Vivo Pharmacological Studies in HuCD4$^+$ Transgenic Mice

Description of HuCD4 Transgenic Mice

Introduction

The high decree of species specificity of CE91 and CE9γ4PE complicates assessment of efficacy in vivo. For CE9.1 pharmacological response could be readily monitored, in the chimp, through a dose-dependent depletion of CD4+cells. The expected absence of this activity in CE9γ4PE induced us to use other means to assess efficacy. In particular, efficacy is being studied in HuCD4 transgenic mice. Studies in this system are described below.

HuCD4$^+$ Transgenics

In the HuCD4 transgenic mice developed at UCSF (Killeen et al., EMBO J., 12:1547–53 (1993)), the endogenous MuCD4 gene was disrupted by homologous recombination and a human CD4 mini-transgene was introduced under the regulation of the MuCD4 promoter. In these mice, which have now been cross-bred to homozygosity, HuCD4 substitutes for MuCD4. HuCD4 restores positive and negative selection in the thymus, leading the production of single positive peripheral CD4$^+$ or CD8$^+$ T cells, at levels computable to those found in normal mice. Moreover, compared to the MuCD4 knockout parent, mature HuCD4 T cells demonstrate properties akin to their normal murine counterparts: (1) in vivo, serum IgG levels are restored to normal levels and (2) these animals show the appropriate MHC-dependent responses in in vitro NMR.

The genetic background of these mice is somewhat complex due to the need to use different strains of embryonic stem cells and mice and in the original knockout and transgenic experiments. The original knockout/transgenic mice were subsequently bred to homozygosity in the MHC locus, and the mice in current use at SB are of the H-2$^{dd}$ haplotype.

Results have shown that a good response to a foreign antigen, ovalbumin, is obtained in these HuCD4 mice, and initial studies have demonstrated in vivo activity for CE9γ4PE.

Preliminary Evaluation of CE9γ4PE in HuCD4 Transgenic Mice

Figure 25:
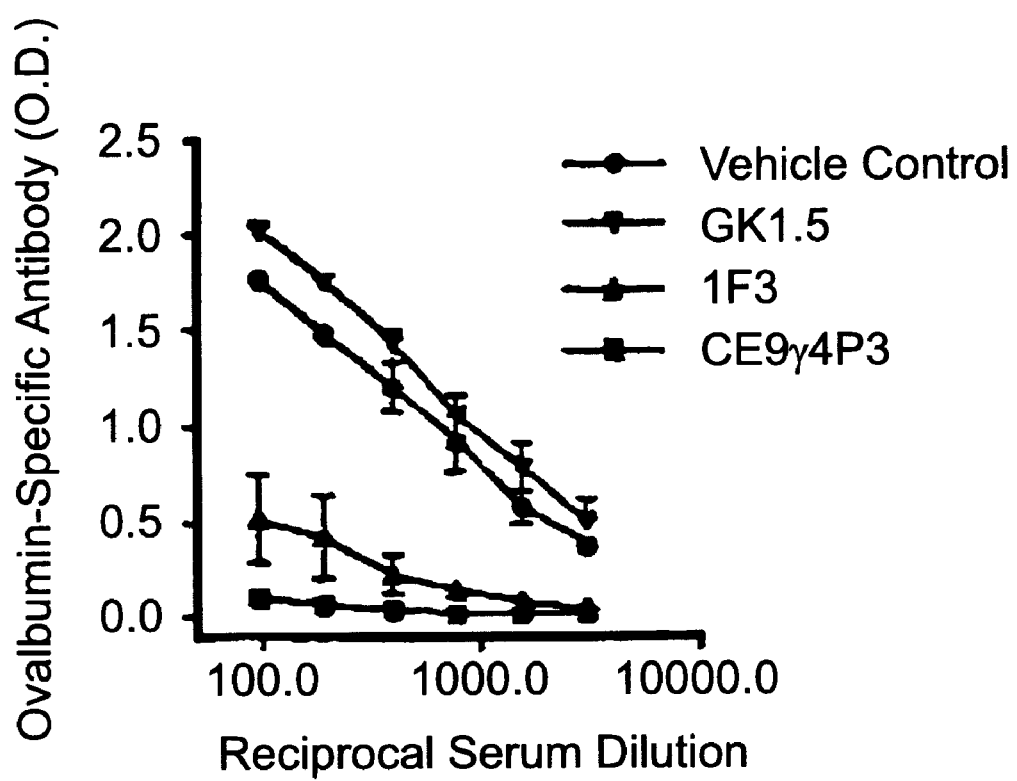
FIG. 25 depicts the effect of treatment with mAbs in ovalbumin-specific antibody response in HuCD4 transgenic mice.

Twelve HuCD4-transgenic mice (H-2$^{dd}$) were received, and used to compare CE9γ4PE with IF3 (murine anti-human CD4) and GK1.5. Mice were dosed on day −2, −1 and day 0 with 1 mg of antibody i.p. and immunized with OVA 3 hr following the last dose. Mice were sacrificed 2 weeks later and serum and cells evaluated for functional activity. The OVA-specific antibody response is shown in FIG. 25. As expected the mAb to mouse CD4 (GK 1.5) had no effect on the humoral response, whereas both mAbs to HuCD4 blocked this response. CE9γ4PE was the more dramatic of the two mAbs.

All groups of mice responded to Con A and LS, however, there was some variation in the response to ovalbumin and in the MLR. This may have been due to the fact that this batch of animals contained both male and female mice and were of different ages.

MuCD4 −/− (CD4 knockout) mice and HuCD4 +/+ (transgenic mice) were treated with CE9.1, CE9γ4PE or saline. The study was carried out over a 28 day period, with samples taken at days 1, 3, 7, 14 and 28. Three color flow cytometric analysis of splenocytes from these mice were used to follow the fate of CD4$^+$ and CD8$^+$ T cells. To examine T cell levels, the following antibodies were used: CD3-PE, OKT4-FITC, CD8-TC. To follow the fate of T and B cells in these mice the following antibodies were used: CD3-PE, CD2-FITC, CD45-TC. To follow the fate of CE9.1 or CE9γ4PE coated cells, the following mAb panel was used: OKT4-PE, Leu3a-FITC, CD3-TC.

The data showed that in both CE9.1 and CE9γ4PE treated transgenic mice (HuCD4 +/+), all CD4$^+$ cells were coated with antibody on day 1. Coating persisted for a few days and was no longer detectable by day 28. The total number of CD4+cells treated in CE9.1 treated mice was decreased significantly, even at day 28. By contrast, CE9γ4PE treated mice showed no decreases in total CD4$^+$ cells. Both antibodies showed evidence of CD4 receptor modulation. Although there was a reciprocal increase in the percentage of CD8$^+$ cells in the CE9.1 treated mice, there was no evidence that these absolute numbers had been significantly affected by the treatment. CD8$^+$ cell numbers were likewise unaffected in CE9γ4PE treated mice. In all experiments, with either antibody, the number of B cells remained constant.

In Vivo Studies in Chimpanzees

Six chimpanzees were examined for depletion of CD4$^+$ T cells and/or modulation of the CD4 receptor from the cell surface after infusions of increasing doses of antibody CE9γ4PE, up to 15 mg/kg. Peripheral blood samples were taken from each chimpanzee three weeks and two weeks prior to the start of the study to establish baseline levels for CD4$^+$ T cells. In addition to CD4$^+$ cells, CD3$^+$ and CD8$^+$ cell levels were also measured by flow cytometry. The mAb OKT4, which binds to a different part of the CD4 molecule and does not compete for binding with CE9γ4PE, was used as a control. By subtraction of CD8$^+$ counts from total CD3$^+$ counts a theoretical value for the number of CD4$^+$ T cells could be calculated. By comparing this value with the CD4+ cells measured suing OKT4, CD4 receptor modulation could be distinguished from CD4+ cell depletion.

At the start of the study, each chimp received an i.v. infusion of saline. Blood samples were taken immediately following infusion and 3 and 14 days later. CE9γ4PE (0.05 mg/kg) was infused into each chimp and blood samples taken 3 and 14 days later. CD4+ cells were monitored and if they were within the normal range, the next level dose of CE9γ4PE was given. In all, each chimp received the following protocol: saline, 0.05 mg/kg CE9γ4PE, 1.5 mg/kg CE9γ4PE, saline, 15 mg/kg CE9γ4PE.

No effects on CD4 levels were seen after infusions of saline or CE9γ4PE at 0.05 mg/kg. At 1.5 mg/kg, CD4+ cell coating was observed and a transient and partial modulation of CD4 receptors from the cells surface, although no CD4+ cell depletion, was seen. At 15 mg/ml of CE9γ4PE, no CD4+cell depletion was observed in any of the animals, although significant modulation was seen in all animals. The modulatory effect was transient and recovered to baseline in 14–21 days. No adverse effects were seen in any animal. CE9γ4PE could be detected on the cell surface up to 2 days after administration and in the serum.

CE9γ4PE was designed to be a non-depleting antibody and no depletion was observed in any animal, even at the relatively high dose of 15 mg/kg. CE9γ4PE was stable in the sera of chimpanzees and remained in circulation for up to 21 days.

Use

Antibodies produced in the manner described above, or by equivalent techniques, can be purified by a combination of affinity and size exclusion chromatography for characterization in functional biological assays. These assays include determination of specificity and binding affinity as well as effector function associated with the expressed isotype, e.g., ADCC, or complement fixation. Such antibodies may be used as passive or active therapeutic agents against a number of human diseases which involve CD4 expression and T cells, including B cell lymphoma, infectious diseases including AIDS, autoimmune and inflammatory diseases, and transplantation. The antibodies can be used either in their native form, or as part of an antibody/chelate, antibody/drug or antibody/toxin complex. Additionally, whole antibodies or antibody fragments ($Fab_2$, Fab, Fv) may be used as imaging reagents or as potential vaccines or immunogens in active immunotherapy for the generation of anti-idiotypic responses.

The amount of antibody useful to produce a therapeutic effect can be determined by standard techniques well known to those of ordinary skill in the art. The antibodies will generally be provided by standard technique within a pharmaceutically acceptable buffer, and may be administered by any desired route. Because of the efficacy of the presently claimed antibodies and their tolerance by humans it is possible to administer these antibodies repetitively in order to combat various diseases or disease states within a human.

The anti-CD4 recombinant antibodies (or fragments thereof) of this invention are also useful for inducing immunomodulation, e.g., inducing suppression of a human's or animal's immune system. This invention therefore relates to a method of prophylactically or therapeutically inducing immunomodulation in a human or other animal in need thereof by administering an effective, non-toxic amount of such an antibody of this invention to such human or other animal.

The ability of the compounds of this invention to induce immunomodulation may be demonstrated in standard tests used for this purpose, for example, a mixed lymphocyte reaction test or a test measuring inhibition of T cell proliferation measured by thymidine uptake.

The fact that the antibodies of this invention have utility in inducing immunosuppression means that they are useful in the treatment or prevention of resistance to or rejection of transplanted organs or tissues (e.g., kidney, heart, lung, bone marrow, skin, cornea, etc.); the treatment or prevention of autoimmune, inflammatory, proliferative and hyperproliferative diseases, and of cutaneous manifestations of immunologically medicated diseases (e.g., rheumatoid arthritis, lupus erythematosus, systemic lupus erythematosus, Hashimotos thyroiditis, multiple sclerosis, myasthenia gravis, type 1 diabetes, uveitis, nephrotic syndrome, psoriasis, atopical dermatitis, contact dermatitis and further eczematous dermatitides, seborrheic dermatitis, Lichen planus, Pemplugus, bullous pemphicjus, Epidermolysis bullosa, urticaria, angioedemas, vasculitides, erythema, cutaneous eosinophilias, Alopecia areata, etc.); the treatment of reversible obstructive airways disease, intestinal inflammations and allergies (e.g., Coeliac disease, proctitis, eosinophilia gastroenteritis, mastocytosis, Crohn's disease and ulcerative colitis) and food-related allergies (e.g., migraine, rhinitis and eczema). Also, the subject antibodies have potential utility for treatment of non-autoimmune conditions wherein immunomodulation is desirable, e.g., graft-versus-host disease (GVHD), transplant rejection, asthma, HIV, leukemia, lymphoma, among others.

One skilled in the art would be able, by routine experimentation, to determine what an effective, non-toxic amount of antibody would be for the purpose of inducing immunosuppression. Generally, however, an effective dosage will be in the range of about 0.05 to 100 milligrams per kilogram body weight per day.

The antibodies (or fragments thereof) of this invention should also be useful for treating tumors in a mammal. More specifically, they should be useful for reducing tumor size, inhibiting tumor growth and/or prolonging the survival time of tumor-bearing animals. Accordingly, this invention also relates to a method of treating tumors in a human or other animal by administering to such human or animal an effective, non-toxic amount of an antibody. One skilled in the art would be able, by routine experimentation, to determine what an effective, non-toxic amount of antibody would be for the purpose of treating carcinogenic tumors. Generally, however, an effective dosage is expected to be in the range of about 0.05 to 100 milligrams per kilogram body weight per day.

The antibodies of the invention may be administered to a human or other animal in accordance with the aforementioned methods of treatment in an amount sufficient to produce such effect to a therapeutic or prophylactic degree. Such antibodies of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The route of administration of the antibody (or fragment thereof) of the invention may be oral, parenteral, by inhalation or topical. The term parenteral as used herein includes intravenous, intramuscular, subcutaneous, rectal, vaginal or intraperitoneal administration. The subcutaneous and intramuscular forms of parenteral administration are generally preferred.

The daily parenteral and oral dosage regimens for employing compounds of the invention to prophylactically or therapeutically induce immunosuppression, or to therapeutically treat carcinogenic tumors will generally be in the range of about 0.05 to 100, but preferably about 0.5 to 10, milligrams per kilogram body weight per day.

The antibody of the invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 10 to 100 milligrams.

The antibody of the invention may also be administered topically. By topical administration is meant non-systemic administration and includes the application of an antibody (or fragment thereof) compound of the invention externally to the epidermis, to the buccal cavity and instillation of such an antibody into the ear, eye and nose, and where it does not significantly enter the blood stream. By systemic administration is meant oral, intravenous, intraperitoneal and intramuscular administration. The amount of an antibody required for therapeutic or prophylactic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

Formulations

While it is possible for an antibody or fragment thereof to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation.

The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 90–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

It will be recognized by one of skill in the art that the optimal quantity and spacing of individual dosages of an antibody or fragment thereof of the invention will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of an antibody or fragment thereof of the invention given per day for a defined number of days, can be ascertained by those skilled in the art using conventional course of treatment determination tests.

Without further elaboration, it is believed that one skilled in the art can, using the preceding description, utilize the present invention to its fullest extent. The following are, therefore, to be construed as merely illustrative examples and not a limitation of the scope of the present invention in any way.

Capsule Composition

A pharmaceutical composition of this invention in the form of a capsule is prepared by filling a standard two-piece hard gelatin capsule with 50 mg. of an antibody or fragment thereof of the invention, in powdered form, 100 mg. of lactose, 32 mg. of talc and 8 mg. of magnesium stearate.

Injectable Parenteral Composition

A pharmaceutical composition of this invention in a form suitable for administration by injection is prepared by stirring 1.5% by weight of an antibody or fragment thereof of the invention in 10 by volume propylene glycol and water. The solution is sterilized by filtration.

Ointment Composition

Antibody or fragment thereof of the invention 1.0 g.

White soft paraffin to 100.0 g.

The antibody or fragment thereof of the invention is dispersed in a small volume of the vehicle to produce a smooth, homogeneous product. Collapsible metal tubes are then filled with the dispersion.

Topical Cream Composition

Antibody or fragment thereof of the invention 1.0 g.

Polawax GP 200 20.0 g.

Lanolin Anhydrous 2.0 g.

White Beeswax 2.5 g.

Methyl hydroxybenzoate 0.1 g.

Distilled Water to 100.0 g.

The polawax, beeswax and lanolin are heated together at 60° C. A solution of methyl hydroxybenzoate is added and homogenization is achieved using high speed stirring. The temperature is then allowed to fall to 50° C. The antibody or fragment thereof of the invention is then added and dispersed throughout, and the composition is allowed to cool with slow speed stirring.

Topical Lotion Composition

Antibody or fragment thereof of the invention 1.0 g.

Sorbitan Monolaurate 0.6 g. Polysorbate 20 0.6 g.

Cetostearyl Alcohol 1.2 g. Glycerin 6.0 g.

Methyl Hydroxybenzoate 0.2 g.

Purified Water B.P. to 100.00 ml. (B.P.=British Pharmacopeia)

The methyl hydroxybenzoate and glycerin are dissolved in 70 ml. of the water at 75° C. The sorbitan monolaurate, polysorbate 20 and cetostearyl alcohol are melted together at 75° C. and added to the aqueous solution. The resulting emulsion is homogenized, allowed to cool with continuous stirring and the antibody or fragment thereof of the invention is added as a suspension in the remaining water. The whole suspension is stirred until homogenized.

Eye Drop Composition

Antibody or fragment thereof of the invention 0.5 g.

Methyl Hydroxybenzoate 0.01 g.

Propyl Hydroxybenzoate 0.04 g.

Purified Water B.P. to 100.00 ml.

The methyl and propyl hydroxybenzoates are dissolved in 70 ml. purified water at 75° C. and the resulting solution is allowed to cool. The antibody or fragment thereof of the invention is then added, and the solution is sterilized by filtration through a membrane filter (0.022 µm pore size), and packed aseptically into suitable sterile containers.

Composition for Administration by Inhalation

For an aerosol container with a capacity of 15–20 ml: mix 10 mg. of an antibody or fragment thereof of the invention with 0.2–0.5% of a lubricating agent, such as polysorbate 85 or oleic acid, and disperse such mixture in a propellant, such as freon, preferably in a combination of (1,2 dichlorotetrafluoroethane) and difluorochloromethane and put into an appropriate aerosol container adapted for either intranasal or oral inhalation administration. Composition for Administration by Inhalation For an aerosol container with a capacity of 15–20 ml: dissolve 10 mg. of an antibody or fragment thereof of the invention in ethanol (6–8 ml.), add 0.1–0.2% of a lubricating agent, such as polysorbate 85 or oleic acid; and disperse such in a propellant, such as freon, preferably in combination of (1.2 dichlorotetrafluoroethane) and difluorochloromethane, and put into an appropriate aerosol container adapted for either intranasal or oral inhalation administration.

The antibodies and pharmaceutical compositions of the invention are particularly useful for parenteral administration, i.e., subcutaneously, intramuscularly or intravenously. The compositions for parenteral administration will commonly comprise a solution of an antibody or fragment thereof of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well-known sterilization techniques. The compositions may contain pharmaceutically acceptable auxiliary substances as required to approximate physiological conditions such as pH adjusting and buffering agents, etc. The concentration of the antibody or fragment thereof of the invention in such pharmaceutical formulation can vary widely, i.e., from less than about 0.5%, usually at or at least about 1% to as much as 15 or 20% by weight, and will be selected primarily based on fluid volumes, viscosities, etc., according to the particular mode of administration selected.

Thus, a pharmaceutical composition of the invention for intramuscular injection could be prepared to contain 1 mL sterile buffered water, and 50 mg. of an antibody or fragment thereof of the invention. Similarly, a pharmaceutical composition of the invention for intravenous infusion could be made up to contain 250 ml. of sterile Ringer's solution, and 150 mg. of an antibody or fragment thereof of the invention. Actual methods for preparing parenterally administrable compositions are well-known or will be apparent to those skilled in the art, and are described in more detail in, for example, *Remington's Pharmaceutical Science,* 15th ed., Mack Publishing Company, Easton, Pa., hereby incorporated by reference herein.

The antibodies (or fragments thereof) of the invention can be lyophilized for storage and reconstituted in a suitable carrier prior to use. This technique has been shown to be effective with conventional immune globulins and art-known lyophilization and reconstitution techniques can be employed.

Depending on the intended result, the pharmaceutical composition of the invention can be administered for prophylactic and/or therapeutic treatments. In therapeutic application, compositions are administered to a patient already suffering from a disease, in an amount sufficient to cure or at least partially arrest the disease and its complications. In prophylactic applications, compositions containing the present antibodies or a cocktail thereof are administered to a patient not already in a disease state to enhance the patient's resistance.

Single or multiple administrations of the pharmaceutical compositions can be carried out with dose levels and pattern being selected by the treating physician. In any event, the pharmaceutical composition of the invention should provide a quantity of the altered antibodies (or fragments thereof) of the invention sufficient to effectively treat the patient.

It should also be noted that the antibodies of this invention may be used for the design and synthesis of either peptide or non-peptide compounds (mimetics) which would be useful in the same therapy as the antibody. See, e.g., Saragovi et al., *Science,* 253:792–795 (1991).

Deposit

Strain XL1 Blue, Anti-CD4 in TCAE6 which expresses CE9.1 has been deposited with the ATCC and assigned number 69030. This deposit was made on Jul. 9, 1992.

Applicants' and their assignees acknowledge their responsibility to replace these cultures should they die before the end of the term of a patent issued hereon, 5 years after the last request for a culture, or 30 years, whichever is the longer, and its responsibility to notify the depository of the issuance of such a patent, at which time the deposit will be made irrevocably available to the public. Until that time the deposit will be made available to the Commissioner of Patents under the terms of 37 C.F.R. Section 1-14 and 35 U.S.C. Section 112.

SEQUENCE LISTING (1) GENERAL INFORMATION:

(iii) NUMBER OF SEQUENCES: 59

(2) INFORMATION FOR SEQ ID NO:1:

(i) SEQUENCE CHARACTERISTICS:
      (A) LENGTH: 420 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Monkey (viii) POSITION IN GENOME:
      (A) CHROMOSOME/SEGMENT: light variable domain of CE9.1

(ix) FEATURE:
      (A) NAME/KEY: CDS
      (B) LOCATION: 4..420

(ix) FEATURE:
      (A) NAME/KEY: mat_peptide
      (B) LOCATION: 61..420

(xi) SEQUENCE DESCRIPTION: SEQ ID NO:1:

```
GAC ATG AAA CAC CTG TGG TTC TTC CTC CTC CTG GTG GCA GCC CCC AGA         48
    Met Lys His Leu Trp Phe Phe Leu Leu Leu Val Ala Ala Pro Arg
    -19             -15                 -10                  -5

TGG GTC TTG TCC CAG GTG CAG CTG CAG GAG GCG GGC CCA GGA CTG GTG         96
Trp Val Leu Ser Gln Val Gln Leu Gln Glu Ala Gly Pro Gly Leu Val
                    1               5                  10

AAG CCT TCG GAG ACC CTG TCC CTC ACC TGC AGT GTC TCT GGT GGC TCC        144
Lys Pro Ser Glu Thr Leu Ser Leu Thr Cys Ser Val Ser Gly Gly Ser
                15                  20                  25

ATC AGC GGT GAC TAT TAT TGG TTC TGG ATC CGC CAG TCC CCA GGG AAG        192
Ile Ser Gly Asp Tyr Tyr Trp Phe Trp Ile Arg Gln Ser Pro Gly Lys
        30                  35                  40

GGA CTG GAG TGG ATC GGC TAC ATC TAT GGC AGT GGT GGG GGC ACC AAT        240
Gly Leu Glu Trp Ile Gly Tyr Ile Tyr Gly Ser Gly Gly Gly Thr Asn
45                  50                  55                  60

TAC AAT CCC TCC CTC AAC AAT CGA GTC TCC ATT TCA ATA GAC ACG TCC        288
Tyr Asn Pro Ser Leu Asn Asn Arg Val Ser Ile Ser Ile Asp Thr Ser
                65                  70                  75

AAG AAC CTC TTC TCC CTG AAA CTG AGG TCT GTG ACC GCC GCG GAC ACG        336
Lys Asn Leu Phe Ser Leu Lys Leu Arg Ser Val Thr Ala Ala Asp Thr
            80                  85                  90

GCC GTC TAT TAC TGT GCG AGT AAT ATA TTG AAA TAT CTT CAC TGG TTA        384
Ala Val Tyr Tyr Cys Ala Ser Asn Ile Leu Lys Tyr Leu His Trp Leu
                95                 100                 105

TTA TAC TGG GGC CAG GGA GTC CTG GTC ACC GTC TCC                        420
Leu Tyr Trp Gly Gln Gly Val Leu Val Thr Val Ser
    110                 115                 120
```

(2) INFORMATION FOR SEQ ID NO:2:

(i) SEQUENCE CHARACTERISTICS:
      (A) LENGTH: 139 amino acids
      (B) TYPE: amino acid
      (D) TOPOLOGY: linear (ii) MOLECULE TYPE: protein (xi) SEQUENCE DESCRIPTION: SEQ ID NO:2:

```
Met Lys His Leu Trp Phe Phe Leu Leu Leu Val Ala Ala Pro Arg Trp
-19             -15                 -10                 -5

Val Leu Ser Gln Val Gln Leu Gln Glu Ala Gly Pro Gly Leu Val Lys
            1               5                   10

Pro Ser Glu Thr Leu Ser Leu Thr Cys Ser Val Ser Gly Gly Ser Ile
        15              20                  25

Ser Gly Asp Tyr Tyr Trp Phe Trp Ile Arg Gln Ser Pro Gly Lys Gly
30              35                  40                  45

Leu Glu Trp Ile Gly Tyr Ile Tyr Gly Ser Gly Gly Thr Asn Tyr
                50              55                  60

Asn Pro Ser Leu Asn Asn Arg Val Ser Ile Ser Ile Asp Thr Ser Lys
            65              70                  75

Asn Leu Phe Ser Leu Lys Leu Arg Ser Val Thr Ala Ala Asp Thr Ala
            80              85                  90

Val Tyr Tyr Cys Ala Ser Asn Ile Leu Lys Tyr Leu His Trp Leu Leu
    95              100                 105

Tyr Trp Gly Gln Gly Val Leu Val Thr Val Ser
110             115                 120
```

(2) INFORMATION FOR SEQ ID NO:3:

(i) SEQUENCE CHARACTERISTICS:
      (A) LENGTH: 387 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Monkey (viii) POSITION IN GENOME:
      (A) CHROMOSOME/SEGMENT: heavy variable domain of CE9.1

(ix) FEATURE:
      (A) NAME/KEY: CDS
      (B) LOCATION: 4..387

(ix) FEATURE:
      (A) NAME/KEY: mat_peptide
      (B) LOCATION: 61..387

(xi) SEQUENCE DESCRIPTION: SEQ ID NO:3:

```
ACC ATG GCC TGG GCT CTG CTG CTC CTC GGC CTC CTT GCT CAC TTT ACA       48
    Met Ala Trp Ala Leu Leu Leu Leu Gly Leu Leu Ala His Phe Thr
    -19             -15                 -10                 -5

GAC TCT GCG GCC TCC TAT GAG TTG AGT CAG CCT CGC TCA GTG TCC GTG       96
Asp Ser Ala Ala Ser Tyr Glu Leu Ser Gln Pro Arg Ser Val Ser Val
                1               5                   10

TCC CCA GGA CAG ACG GCC GGG TTC ACC TGT GGG GGA GAC AAC GTT GGA      144
Ser Pro Gly Gln Thr Ala Gly Phe Thr Cys Gly Gly Asp Asn Val Gly
        15                  20                  25

AGG AAA AGT GTA CAG TGG TAC CAG CAG AAG CCA CCG CAG GCC CCT GTG      192
Arg Lys Ser Val Gln Trp Tyr Gln Gln Lys Pro Pro Gln Ala Pro Val
30                  35                  40

CTG GTC ATC TAT GCT GAC AGC GAA CGG CCC TCA GGG ATC CCT GCG CGA      240
Leu Val Ile Tyr Ala Asp Ser Glu Arg Pro Ser Gly Ile Pro Ala Arg
45                  50                  55                  60

TTC TCT GGC TCC AAC TCA GGG AAC ACC GCC ACC CTG ACC ATC AGC GGG      288
Phe Ser Gly Ser Asn Ser Gly Asn Thr Ala Thr Leu Thr Ile Ser Gly
```

```
                    65                  70                  75
GTC GAG GCC GGG GAT GAG GCT GAC TAT TAC TGT CAG GTG TGG GAC AGT        336
Val Glu Ala Gly Asp Glu Ala Asp Tyr Tyr Cys Gln Val Trp Asp Ser
                80                  85                  90

ACT GCT GAT CAT TGG GTC TTC GGC GGA GGG ACC CGG CTG ACC GTC CTA        384
Thr Ala Asp His Trp Val Phe Gly Gly Gly Thr Arg Leu Thr Val Leu
        95                 100                 105

GGT                                                                    387
Gly (2) INFORMATION FOR SEQ ID NO:4:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Trp Ala Leu Leu Leu Leu Gly Leu Leu Ala His Phe Thr Asp
-19             -15                 -10                 -5

Ser Ala Ala Ser Tyr Glu Leu Ser Gln Pro Arg Ser Val Ser Val Ser
            1               5                   10

Pro Gly Gln Thr Ala Gly Phe Thr Cys Gly Gly Asp Asn Val Gly Arg
        15                  20                  25

Lys Ser Val Gln Trp Tyr Gln Gln Lys Pro Pro Gln Ala Pro Val Leu
    30              35                  40                  45

Val Ile Tyr Ala Asp Ser Glu Arg Pro Ser Gly Ile Pro Ala Arg Phe
            50                  55                  60

Ser Gly Ser Asn Ser Gly Asn Thr Ala Thr Leu Thr Ile Ser Gly Val
                65                  70                  75

Glu Ala Gly Asp Glu Ala Asp Tyr Tyr Cys Gln Val Trp Asp Ser Thr
            80                  85                  90

Ala Asp His Trp Val Phe Gly Gly Gly Thr Arg Leu Thr Val Leu Gly
        95                 100                 105

(2) INFORMATION FOR SEQ ID NO:5:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (viii) POSITION IN GENOME:
        (A) CHROMOSOME/SEGMENT: lambda variable and constant
            domains in CE9.1

(ix) FEATURE:
        (A) NAME/KEY: CDS
        (B) LOCATION: 1..702

(ix) FEATURE:
        (A) NAME/KEY: mat_peptide
        (B) LOCATION: 1..702

(xi) SEQUENCE DESCRIPTION: SEQ ID NO:5:

ATG GCC TGG GCT CTG CTG CTC CTC GGC CTC CTT GCT CAC TTT ACA GAC        48
Met Ala Trp Ala Leu Leu Leu Leu Gly Leu Leu Ala His Phe Thr Asp
```

```
      1               5                    10                   15
TCT GCG GCC TCC TAT GAG TTG AGT CAG CCT CGC TCA GTG TCC GTG TCC      96
Ser Ala Ala Ser Tyr Glu Leu Ser Gln Pro Arg Ser Val Ser Val Ser
                     20                  25                  30

CCA GGA CAG ACG GCC GGG TTC ACC TGT GGG GGA GAC AAC GTT GGA AGG     144
Pro Gly Gln Thr Ala Gly Phe Thr Cys Gly Gly Asp Asn Val Gly Arg
             35                  40                  45

AAA AGT GTA CAG TGG TAC CAG CAG AAG CCA CCG CAG GCC CCT GTG CTG     192
Lys Ser Val Gln Trp Tyr Gln Gln Lys Pro Pro Gln Ala Pro Val Leu
         50                  55                  60

GTC ATC TAT GCT GAC AGC GAA CGG CCC TCA GGG ATC CCT GCG CGA TTC     240
Val Ile Tyr Ala Asp Ser Glu Arg Pro Ser Gly Ile Pro Ala Arg Phe
     65                  70                  75                  80

TCT GGC TCC AAC TCA GGG AAC ACC GCC ACC CTG ACC ATC AGC GGG GTC     288
Ser Gly Ser Asn Ser Gly Asn Thr Ala Thr Leu Thr Ile Ser Gly Val
                     85                  90                  95

GAG GCC GGG GAT GAG GCT GAC TAT TAC TGT CAG GTG TGG GAC AGT ACT     336
Glu Ala Gly Asp Glu Ala Asp Tyr Tyr Cys Gln Val Trp Asp Ser Thr
                 100                 105                 110

GCT GAT CAT TGG GTC TTC GGC GGA GGG ACC CGG CTG ACC GTC CTA GGT     384
Ala Asp His Trp Val Phe Gly Gly Gly Thr Arg Leu Thr Val Leu Gly
             115                 120                 125

CAG CCC AAG GCT GCC CCC TCG GTC ACT CTG TTC CCG CCC TCC TCT GAG     432
Gln Pro Lys Ala Ala Pro Ser Val Thr Leu Phe Pro Pro Ser Ser Glu
         130                 135                 140

GAG CTT CAA GCC AAC AAG GCC ACA CTG GTG TGT CTC ATA AGT GAC TTC     480
Glu Leu Gln Ala Asn Lys Ala Thr Leu Val Cys Leu Ile Ser Asp Phe
145                 150                 155                 160

TAC CCG GGA GCC GTG ACA GTG GCC TGG AAG GCA GAT AGC AGC CCC GTC     528
Tyr Pro Gly Ala Val Thr Val Ala Trp Lys Ala Asp Ser Ser Pro Val
                 165                 170                 175

AAG GCG GGA GTG GAG ACC ACC ACA CCC TCC AAA CAA AGC AAC AAC AAG     576
Lys Ala Gly Val Glu Thr Thr Thr Pro Ser Lys Gln Ser Asn Asn Lys
             180                 185                 190

TAC GCG GCC AGC AGC TAC CTG AGC CTG ACG CCT GAG CAG TGG AAG TCC     624
Tyr Ala Ala Ser Ser Tyr Leu Ser Leu Thr Pro Glu Gln Trp Lys Ser
         195                 200                 205

CAC AGA AGC TAC AGC TGC CAG GTC ACG CAT GAA GGG AGC ACC GTG GAG     672
His Arg Ser Tyr Ser Cys Gln Val Thr His Glu Gly Ser Thr Val Glu
     210                 215                 220

AAG ACA GTG GCC CCT ACA GAA TGT TCA TGA                             702
Lys Thr Val Ala Pro Thr Glu Cys Ser *
225                 230
```

(2) INFORMATION FOR SEQ ID NO:6:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ala Trp Ala Leu Leu Leu Leu Gly Leu Leu Ala His Phe Thr Asp
 1               5                  10                  15

Ser Ala Ala Ser Tyr Glu Leu Ser Gln Pro Arg Ser Val Ser Val Ser
             20                  25                  30

Pro Gly Gln Thr Ala Gly Phe Thr Cys Gly Gly Asp Asn Val Gly Arg
         35                  40                  45
```

```
Lys Ser Val Gln Trp Tyr Gln Gln Lys Pro Pro Gln Ala Pro Val Leu
 50                  55                  60

Val Ile Tyr Ala Asp Ser Glu Arg Pro Ser Gly Ile Pro Ala Arg Phe
 65                  70                  75                  80

Ser Gly Ser Asn Ser Gly Asn Thr Ala Thr Leu Thr Ile Ser Gly Val
                 85                  90                  95

Glu Ala Gly Asp Glu Ala Asp Tyr Tyr Cys Gln Val Trp Asp Ser Thr
                100                 105                 110

Ala Asp His Trp Val Phe Gly Gly Gly Thr Arg Leu Thr Val Leu Gly
                115                 120                 125

Gln Pro Lys Ala Ala Pro Ser Val Thr Leu Phe Pro Pro Ser Ser Glu
        130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
                180                 185                 190

Tyr Ala Ala Ser Ser Tyr Leu Ser Leu Thr Pro Glu Gln Trp Lys Ser
            195                 200                 205

His Arg Ser Tyr Ser Cys Gln Val Thr His Glu Gly Ser Thr Val Glu
        210                 215                 220

Lys Thr Val Ala Pro Thr Glu Cys Ser
225                 230
```

(2) INFORMATION FOR SEQ ID NO:7:

(i) SEQUENCE CHARACTERISTICS:
        (A) LENGTH: 1404 base pairs
        (B) TYPE: nucleic acid
        (C) STRANDEDNESS: single
        (D) TOPOLOGY: linear (ii) MOLECULE TYPE: DNA (genomic)

(viii) POSITION IN GENOME:
        (A) CHROMOSOME/SEGMENT: heavy chain variable and constant
            gamma 4

(ix) FEATURE:
        (A) NAME/KEY: CDS
        (B) LOCATION: 1..1404

(ix) FEATURE:
        (A) NAME/KEY: mat_peptide
        (B) LOCATION: 1..1404

(xi) SEQUENCE DESCRIPTION: SEQ ID NO:7:

```
ATG AAA CAC CTG TGG TTC TTC CTC CTC CTG GTG GCA GCC CCC AGA TGG      48
Met Lys His Leu Trp Phe Phe Leu Leu Leu Val Ala Ala Pro Arg Trp
 1               5                  10                  15

GTC TTG TCC CAG GTG CAG CTG CAG GAG TCG GGC CCA GGA CTG GTG AAG      96
Val Leu Ser Gln Val Gln Leu Gln Glu Ser Gly Pro Gly Leu Val Lys
                 20                  25                  30

CCT TCG GAG ACC CTG TCC CTC ACC TGC AGT GTC TCT GGT GGC TCC ATC     144
Pro Ser Glu Thr Leu Ser Leu Thr Cys Ser Val Ser Gly Gly Ser Ile
         35                  40                  45

AGC GGT GAC TAT TAT TGG TTC TGG ATC CGC CAG TCC CCA GGG AAG GGA     192
Ser Gly Asp Tyr Tyr Trp Phe Trp Ile Arg Gln Ser Pro Gly Lys Gly
     50                  55                  60

CTG GAG TGG ATC GGC TAC ATC TAT GGC AGT GGT GGG GGC ACC AAT TAC     240
Leu Glu Trp Ile Gly Tyr Ile Tyr Gly Ser Gly Gly Gly Thr Asn Tyr
```

```
                65                    70                    75                    80
AAT CCC TCC CTC AAC AAT CGA GTC TCC ATT TCA ATA GAC ACG TCC AAG         288
Asn Pro Ser Leu Asn Asn Arg Val Ser Ile Ser Ile Asp Thr Ser Lys
                    85                    90                    95

AAC CTC TTC TCC CTG AAA CTG AGG TCT GTG ACC GCC GCG GAC ACG GCC         336
Asn Leu Phe Ser Leu Lys Leu Arg Ser Val Thr Ala Ala Asp Thr Ala
            100                   105                   110

GTC TAT TAC TGT GCG AGT AAT ATA TTG AAA TAT CTT CAC TGG TTA TTA         384
Val Tyr Tyr Cys Ala Ser Asn Ile Leu Lys Tyr Leu His Trp Leu Leu
            115                   120                   125

TAC TGG GGC CAG GGA GTC CTG GTC ACC GTC TCC TCA GCT AGC ACC AAG         432
Tyr Trp Gly Gln Gly Val Leu Val Thr Val Ser Ser Ala Ser Thr Lys
    130                   135                   140

GGC CCA TCC GTC TTC CCC CTG GCG CCC TGC TCC AGG AGC ACC TCC GAG         480
Gly Pro Ser Val Phe Pro Leu Ala Pro Cys Ser Arg Ser Thr Ser Glu
145                   150                   155                   160

AGC ACA GCC GCC CTG GGC TGC CTG GTC AAG GAC TAC TTC CCC GAA CCG         528
Ser Thr Ala Ala Leu Gly Cys Leu Val Lys Asp Tyr Phe Pro Glu Pro
            165                   170                   175

GTG ACG GTG TCG TGG AAC TCA GGC GCC CTG ACC AGC GGC GTG CAC ACC         576
Val Thr Val Ser Trp Asn Ser Gly Ala Leu Thr Ser Gly Val His Thr
            180                   185                   190

TTC CCG GCT GTC CTA CAG TCC TCA GGA CTC TAC TCC CTC AGC AGC GTG         624
Phe Pro Ala Val Leu Gln Ser Ser Gly Leu Tyr Ser Leu Ser Ser Val
            195                   200                   205

GTG ACC GTG CCC TCC AGC AGC TTG GGC ACG AAG ACC TAC ACC TGC AAC         672
Val Thr Val Pro Ser Ser Ser Leu Gly Thr Lys Thr Tyr Thr Cys Asn
    210                   215                   220

GTA GAT CAC AAG CCC AGC AAC ACC AAG GTG GAC AAG AGA GTT GAG TCC         720
Val Asp His Lys Pro Ser Asn Thr Lys Val Asp Lys Arg Val Glu Ser
225                   230                   235                   240

AAA TAT GGT CCC CCA TGC CCA TCA TGC CCA GCA CCT GAG TTC CTG GGG         768
Lys Tyr Gly Pro Pro Cys Pro Ser Cys Pro Ala Pro Glu Phe Leu Gly
            245                   250                   255

GGA CCA TCA GTC TTC CTG TTC CCC CCA AAA CCC AAG GAC ACT CTC ATG         816
Gly Pro Ser Val Phe Leu Phe Pro Pro Lys Pro Lys Asp Thr Leu Met
            260                   265                   270

ATC TCC CGG ACC CCT GAG GTC ACG TGC GTG GTG GTG GAC GTG AGC CAG         864
Ile Ser Arg Thr Pro Glu Val Thr Cys Val Val Val Asp Val Ser Gln
            275                   280                   285

GAA GAC CCC GAG GTC CAG TTC AAC TGG TAC GTG GAT GGC GTG GAG GTG         912
Glu Asp Pro Glu Val Gln Phe Asn Trp Tyr Val Asp Gly Val Glu Val
    290                   295                   300

CAT AAT GCC AAG ACA AAG CCG CGG GAG GAG CAG TTC AAC AGC ACG TAC         960
His Asn Ala Lys Thr Lys Pro Arg Glu Glu Gln Phe Asn Ser Thr Tyr
305                   310                   315                   320

CGT GTG GTC AGC GTC CTC ACC GTC CTG CAC CAG GAC TGG CTG AAC GGC        1008
Arg Val Val Ser Val Leu Thr Val Leu His Gln Asp Trp Leu Asn Gly
            325                   330                   335

AAG GAG TAC AAG TGC AAG GTC TCC AAC AAA GGC CTC CCG TCC TCC ATC        1056
Lys Glu Tyr Lys Cys Lys Val Ser Asn Lys Gly Leu Pro Ser Ser Ile
            340                   345                   350

GAG AAA ACC ATC TCC AAA GCC AAA GGG CAG CCC CGA GAG CCA CAG GTG        1104
Glu Lys Thr Ile Ser Lys Ala Lys Gly Gln Pro Arg Glu Pro Gln Val
            355                   360                   365

TAC ACC CTG CCC CCA TCC CAG GAG GAG ATG ACC AAG AAC CAG GTC AGC        1152
Tyr Thr Leu Pro Pro Ser Gln Glu Glu Met Thr Lys Asn Gln Val Ser
            370                   375                   380

CTG ACC TGC CTG GTC AAA GGC TTC TAC CCC AGC GAC ATC GCC GTG GAG        1200
Leu Thr Cys Leu Val Lys Gly Phe Tyr Pro Ser Asp Ile Ala Val Glu
```

```
Leu Thr Cys Leu Val Lys Gly Phe Tyr Pro Ser Asp Ile Ala Val Glu
385                 390                 395                 400

TGG GAG AGC AAT GGG CAG CCG GAG AAC AAC TAC AAG ACC ACG CCT CCC       1248
Trp Glu Ser Asn Gly Gln Pro Glu Asn Asn Tyr Lys Thr Thr Pro Pro
                405                 410                 415

GTG CTG GAC TCC GAC GGC TCC TTC TTC CTC TAC AGC AGG CTA ACC GTG       1296
Val Leu Asp Ser Asp Gly Ser Phe Phe Leu Tyr Ser Arg Leu Thr Val
            420                 425                 430

GAC AAG AGC AGG TGG CAG GAG GGG AAT GTC TTC TCA TGC TCC GTG ATG       1344
Asp Lys Ser Arg Trp Gln Glu Gly Asn Val Phe Ser Cys Ser Val Met
        435                 440                 445

CAT GAG GCT CTG CAC AAC CAC TAC ACA CAG AAG AGC CTC TCC CTG TCT       1392
His Glu Ala Leu His Asn His Tyr Thr Gln Lys Ser Leu Ser Leu Ser
    450                 455                 460

CTG GGT AAA TGA                                                       1404
Leu Gly Lys *
465

(2) INFORMATION FOR SEQ ID NO:8:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:8:

Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
            20                  25                  30

Pro Ser Glu Thr Leu Ser Leu Thr Cys Ser Val Ser Gly Gly Ser Ile
        35                  40                  45

Ser Gly Asp Tyr Tyr Trp Phe Trp Ile Arg Gln Ser Pro Gly Lys Gly
    50                  55                  60

Leu Glu Trp Ile Gly Tyr Ile Tyr Gly Ser Gly Gly Thr Asn Tyr
65                  70                  75                  80

Asn Pro Ser Leu Asn Asn Arg Val Ser Ile Ser Ile Asp Thr Ser Lys
                85                  90                  95

Asn Leu Phe Ser Leu Lys Leu Arg Ser Val Thr Ala Ala Asp Thr Ala
            100                 105                 110

Val Tyr Tyr Cys Ala Ser Asn Ile Leu Lys Tyr Leu His Trp Leu Leu
        115                 120                 125

Tyr Trp Gly Gln Gly Val Leu Val Thr Val Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240
```

```
Lys Tyr Gly Pro Pro Cys Pro Ser Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
            275                 280                 285

Glu Asp Pro Glu Val Gln Phe Asn Trp Tyr Val Asp Gly Val Glu Val
        290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Gln Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
            435                 440                 445

His Glu Ala Leu His Asn His Tyr Thr Gln Lys Ser Leu Ser Leu Ser
450                 455                 460

Leu Gly Lys
465

(2) INFORMATION FOR SEQ ID NO:9:

(i) SEQUENCE CHARACTERISTICS:
        (A) LENGTH: 1404 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (viii) POSITION IN GENOME:
        (A) CHROMOSOME/SEGMENT: heavy chain gamma 4 with the E
            mutation (ix) FEATURE:
        (A) NAME/KEY: CDS
        (B) LOCATION: 1..1404

(ix) FEATURE:
        (A) NAME/KEY: mat_peptide
        (B) LOCATION: 1..1404

(xi) SEQUENCE DESCRIPTION: SEQ ID NO:9:

ATG AAA CAC CTG TGG TTC TTC CTC CTC CTG GTG GCA GCC CCC AGA TGG        48
Met Lys His Leu Trp Phe Phe Leu Leu Leu Val Ala Ala Pro Arg Trp
  1               5                  10                  15

GTC TTG TCC CAG GTG CAG CTG CAG GAG TCG GGC CCA GGA CTG GTG AAG        96
```

-continued

```
              Val Leu Ser Gln Val Gln Leu Gln Glu Ser Gly Pro Gly Leu Val Lys
                           20                  25                  30

CCT TCG GAG ACC CTG TCC CTC ACC TGC AGT GTC TCT GGT GGC TCC ATC       144
Pro Ser Glu Thr Leu Ser Leu Thr Cys Ser Val Ser Gly Gly Ser Ile
            35                  40                  45

AGC GGT GAC TAT TAT TGG TTC TGG ATC CGC CAG TCC CCA GGG AAG GGA       192
Ser Gly Asp Tyr Tyr Trp Phe Trp Ile Arg Gln Ser Pro Gly Lys Gly
 50                  55                  60

CTG GAG TGG ATC GGC TAC ATC TAT GGC AGT GGT GGG GGC ACC AAT TAC       240
Leu Glu Trp Ile Gly Tyr Ile Tyr Gly Ser Gly Gly Gly Thr Asn Tyr
 65                  70                  75                  80

AAT CCC TCC CTC AAC AAT CGA GTC TCC ATT TCA ATA GAC ACG TCC AAG       288
Asn Pro Ser Leu Asn Asn Arg Val Ser Ile Ser Ile Asp Thr Ser Lys
                85                  90                  95

AAC CTC TTC TCC CTG AAA CTG AGG TCT GTG ACC GCC GCG GAC ACG GCC       336
Asn Leu Phe Ser Leu Lys Leu Arg Ser Val Thr Ala Ala Asp Thr Ala
            100                 105                 110

GTC TAT TAC TGT GCG AGT AAT ATA TTG AAA TAT CTT CAC TGG TTA TTA       384
Val Tyr Tyr Cys Ala Ser Asn Ile Leu Lys Tyr Leu His Trp Leu Leu
        115                 120                 125

TAC TGG GGC CAG GGA GTC CTG GTC ACC GTC TCC TCA GCT AGC ACC AAG       432
Tyr Trp Gly Gln Gly Val Leu Val Thr Val Ser Ser Ala Ser Thr Lys
    130                 135                 140

GGG CCA TCC GTC TTC CCC CTG GCG CCC TGC TCC AGG AGC ACC TCC GAG       480
Gly Pro Ser Val Phe Pro Leu Ala Pro Cys Ser Arg Ser Thr Ser Glu
145                 150                 155                 160

AGC ACA GCC GCC CTG GGC TGC CTG GTC AAG GAC TAC TTC CCC GAA CCG       528
Ser Thr Ala Ala Leu Gly Cys Leu Val Lys Asp Tyr Phe Pro Glu Pro
                165                 170                 175

GTG ACG GTG TCG TGG AAC TCA GGC GCC CTG ACC AGC GGC GTG CAC ACC       576
Val Thr Val Ser Trp Asn Ser Gly Ala Leu Thr Ser Gly Val His Thr
            180                 185                 190

TTC CCG GCT GTC CTA CAG TCC TCA GGA CTC TAC TCC CTC AGC AGC GTG       624
Phe Pro Ala Val Leu Gln Ser Ser Gly Leu Tyr Ser Leu Ser Ser Val
        195                 200                 205

GTG ACC GTG CCC TCC AGC AGC TTG GGC ACG AAG ACC TAC ACC TGC AAC       672
Val Thr Val Pro Ser Ser Ser Leu Gly Thr Lys Thr Tyr Thr Cys Asn
    210                 215                 220

GTA GAT CAC AAG CCC AGC AAC ACC AAG GTG GAC AAG AGA GTT GAG TCC       720
Val Asp His Lys Pro Ser Asn Thr Lys Val Asp Lys Arg Val Glu Ser
225                 230                 235                 240

AAA TAT GGT CCC CCA TGC CCA TCA TGC CCA GCA CCT GAG TTC GAG GGG       768
Lys Tyr Gly Pro Pro Cys Pro Ser Cys Pro Ala Pro Glu Phe Glu Gly
                245                 250                 255

GGA CCA TCA GTC TTC CTG TTC CCC CCA AAA CCC AAG GAC ACT CTC ATG       816
Gly Pro Ser Val Phe Leu Phe Pro Pro Lys Pro Lys Asp Thr Leu Met
            260                 265                 270

ATC TCC CGG ACC CCT GAG GTC ACG TGC GTG GTG GTG GAC GTG AGC CAG       864
Ile Ser Arg Thr Pro Glu Val Thr Cys Val Val Val Asp Val Ser Gln
        275                 280                 285

GAA GAC CCC GAG GTC CAG TTC AAC TGG TAC GTG GAT GGC GTG GAG GTG       912
Glu Asp Pro Glu Val Gln Phe Asn Trp Tyr Val Asp Gly Val Glu Val
    290                 295                 300

CAT AAT GCC AAG ACA AAG CCG CGG GAG GAG CAG TTC AAC AGC ACG TAC       960
His Asn Ala Lys Thr Lys Pro Arg Glu Glu Gln Phe Asn Ser Thr Tyr
305                 310                 315                 320

CGT GTG GTC AGC GTC CTC ACC GTC CTG CAC CAG GAC TGG CTG AAC GGC       1008
Arg Val Val Ser Val Leu Thr Val Leu His Gln Asp Trp Leu Asn Gly
                325                 330                 335
```

```
AAG GAG TAC AAG TGC AAG GTC TCC AAC AAA GGC CTC CCG TCC TCC ATC        1056
Lys Glu Tyr Lys Cys Lys Val Ser Asn Lys Gly Leu Pro Ser Ser Ile
            340                 345                 350

GAG AAA ACC ATC TCC AAA GCC AAA GGG CAG CCC CGA GAG CCA CAG GTG        1104
Glu Lys Thr Ile Ser Lys Ala Lys Gly Gln Pro Arg Glu Pro Gln Val
            355                 360                 365

TAC ACC CTG CCC CCA TCC CAG GAG GAG ATG ACC AAG AAC CAG GTC AGC        1152
Tyr Thr Leu Pro Pro Ser Gln Glu Glu Met Thr Lys Asn Gln Val Ser
        370                 375                 380

CTG ACC TGC CTG GTC AAA GGC TTC TAC CCC AGC GAC ATC GCC GTG GAG        1200
Leu Thr Cys Leu Val Lys Gly Phe Tyr Pro Ser Asp Ile Ala Val Glu
385                 390                 395                 400

TGG GAG AGC AAT GGG CAG CCG GAG AAC AAC TAC AAG ACG ACG CCT CCC        1248
Trp Glu Ser Asn Gly Gln Pro Glu Asn Asn Tyr Lys Thr Thr Pro Pro
                405                 410                 415

GTG CTG GAC TCC GAC GGC TCC TTC TTC CTC TAC AGC AGG CTA ACC GTG        1296
Val Leu Asp Ser Asp Gly Ser Phe Phe Leu Tyr Ser Arg Leu Thr Val
            420                 425                 430

GAC AAG AGC AGG TGG CAG GAG GGG AAT GTC TTC TCA TGC TCC GTG ATG        1344
Asp Lys Ser Arg Trp Gln Glu Gly Asn Val Phe Ser Cys Ser Val Met
        435                 440                 445

CAT GAG GCT CTG CAC AAC CAC TAC ACA CAG AAG AGC CTC TCC CTG TCT        1392
His Glu Ala Leu His Asn His Tyr Thr Gln Lys Ser Leu Ser Leu Ser
450                 455                 460

CTG GGT AAA TGA                                                        1404
Leu Gly Lys *
465

(2) INFORMATION FOR SEQ ID NO:10:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:10:

Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
            20                  25                  30

Pro Ser Glu Thr Leu Ser Leu Thr Cys Ser Val Ser Gly Gly Ser Ile
        35                  40                  45

Ser Gly Asp Tyr Tyr Trp Phe Trp Ile Arg Gln Ser Pro Gly Lys Gly
    50                  55                  60

Leu Glu Trp Ile Gly Tyr Ile Tyr Gly Ser Gly Gly Thr Asn Tyr
65                  70                  75                  80

Asn Pro Ser Leu Asn Asn Arg Val Ser Ile Ser Ile Asp Thr Ser Lys
                85                  90                  95

Asn Leu Phe Ser Leu Lys Leu Arg Ser Val Thr Ala Ala Asp Thr Ala
            100                 105                 110

Val Tyr Tyr Cys Ala Ser Asn Ile Leu Lys Tyr Leu His Trp Leu Leu
        115                 120                 125

Tyr Trp Gly Gln Gly Val Leu Val Thr Val Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
```

```
                    165                 170                 175
Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200             205

Val Thr Val Pro Ser Ser Ser Leu Gly Thr Lys Thr Tyr Thr Cys Asn
            210                 215             220

Val Asp His Lys Pro Ser Asn Thr Lys Val Asp Lys Arg Val Glu Ser
225                     230              235                 240

Lys Tyr Gly Pro Pro Cys Pro Ser Cys Pro Ala Pro Glu Phe Glu Gly
                245                 250                 255

Gly Pro Ser Val Phe Leu Phe Pro Pro Lys Pro Lys Asp Thr Leu Met
            260                 265             270

Ile Ser Arg Thr Pro Glu Val Thr Cys Val Val Val Asp Val Ser Gln
            275                 280             285

Glu Asp Pro Glu Val Gln Phe Asn Trp Tyr Val Asp Gly Val Glu Val
290                     295             300

His Asn Ala Lys Thr Lys Pro Arg Glu Glu Gln Phe Asn Ser Thr Tyr
305                     310             315                 320

Arg Val Val Ser Val Leu Thr Val Leu His Gln Asp Trp Leu Asn Gly
            325                 330                 335

Lys Glu Tyr Lys Cys Lys Val Ser Asn Lys Gly Leu Pro Ser Ser Ile
            340                 345             350

Glu Lys Thr Ile Ser Lys Ala Lys Gly Gln Pro Arg Glu Pro Gln Val
            355                 360             365

Tyr Thr Leu Pro Pro Ser Gln Glu Glu Met Thr Lys Asn Gln Val Ser
            370                 375             380

Leu Thr Cys Leu Val Lys Gly Phe Tyr Pro Ser Asp Ile Ala Val Glu
385                     390             395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
                420                 425             430

Asp Lys Ser Arg Trp Gln Glu Gly Asn Val Phe Ser Cys Ser Val Met
            435                 440             445

His Glu Ala Leu His Asn His Tyr Thr Gln Lys Ser Leu Ser Leu Ser
    450                 455             460

Leu Gly Lys
465

(2) INFORMATION FOR SEQ ID NO:11:

(i) SEQUENCE CHARACTERISTICS:
        (A) LENGTH: 1404 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (viii) POSITION IN GENOME:
        (A) CHROMOSOME/SEGMENT: heavy chain gamma 4 with the P and E
            mutation (ix) FEATURE:
        (A) NAME/KEY: CDS
```

-continued (B) LOCATION: 1..1404

(ix) FEATURE:
    (A) NAME/KEY: mat_peptide
    (B) LOCATION: 1..1404

(xi) SEQUENCE DESCRIPTION: SEQ ID NO:11:

```
ATG AAA CAC CTG TGG TTC TTC CTC CTC CTG GTG GCA GCC CCC AGA TGG        48
Met Lys His Leu Trp Phe Phe Leu Leu Leu Val Ala Ala Pro Arg Trp
 1               5                   10                  15

GTC TTG TCC CAG GTG CAG CTG CAG GAG TCG GGC CCA GGA CTG GTG AAG        96
Val Leu Ser Gln Val Gln Leu Gln Glu Ser Gly Pro Gly Leu Val Lys
                20                  25                  30

CCT TCG GAG ACC CTG TCC CTC ACC TGC AGT GTC TCT GGT GGC TCC ATC       144
Pro Ser Glu Thr Leu Ser Leu Thr Cys Ser Val Ser Gly Gly Ser Ile
            35                  40                  45

AGC GGT GAC TAT TAT TGG TTC TGG ATC CGC CAG TCC CCA GGG AAG GGA       192
Ser Gly Asp Tyr Tyr Trp Phe Trp Ile Arg Gln Ser Pro Gly Lys Gly
        50                  55                  60

CTG GAG TGG ATC GGC TAC ATC TAT GGC AGT GGT GGG GGC ACC AAT TAC       240
Leu Glu Trp Ile Gly Tyr Ile Tyr Gly Ser Gly Gly Gly Thr Asn Tyr
 65                 70                  75                  80

AAT CCC TCC CTC AAC AAT CGA GTC TCC ATT TCA ATA GAC ACG TCC AAG       288
Asn Pro Ser Leu Asn Asn Arg Val Ser Ile Ser Ile Asp Thr Ser Lys
                85                  90                  95

AAC CTC TTC TCC CTG AAA CTG AGG TCT GTG ACC GCC GCG GAC ACG GCC       336
Asn Leu Phe Ser Leu Lys Leu Arg Ser Val Thr Ala Ala Asp Thr Ala
            100                 105                 110

GTC TAT TAC TGT GCG AGT AAT ATA TTG AAA TAT CTT CAC TGG TTA TTA       384
Val Tyr Tyr Cys Ala Ser Asn Ile Leu Lys Tyr Leu His Trp Leu Leu
        115                 120                 125

TAC TGG GGC CAG GGA GTC CTG GTC ACC GTC TCC TCA GCT AGC ACC AAG       432
Tyr Trp Gly Gln Gly Val Leu Val Thr Val Ser Ser Ala Ser Thr Lys
130                 135                 140

GGG CCA TCC GTC TTC CCC CTG GCG CCC TGC TCC AGG AGC ACC TCC GAG       480
Gly Pro Ser Val Phe Pro Leu Ala Pro Cys Ser Arg Ser Thr Ser Glu
145                 150                 155                 160

AGC ACA GCC GCC CTG GGC TGC CTG GTC AAG GAC TAC TTC CCC GAA CCG       528
Ser Thr Ala Ala Leu Gly Cys Leu Val Lys Asp Tyr Phe Pro Glu Pro
                165                 170                 175

GTG ACG GTG TCG TGG AAC TCA GGC GCC CTG ACC AGC GGC GTG CAC ACC       576
Val Thr Val Ser Trp Asn Ser Gly Ala Leu Thr Ser Gly Val His Thr
            180                 185                 190

TTC CCG GCT GTC CTA CAG TCC TCA GGA CTC TAC TCC CTC AGC AGC GTG       624
Phe Pro Ala Val Leu Gln Ser Ser Gly Leu Tyr Ser Leu Ser Ser Val
        195                 200                 205

GTG ACC GTG CCC TCC AGC AGC TTG GGC ACG AAG ACC TAC ACC TGC AAC       672
Val Thr Val Pro Ser Ser Ser Leu Gly Thr Lys Thr Tyr Thr Cys Asn
    210                 215                 220

GTA GAT CAC AAG CCC AGC AAC ACC AAG GTG GAC AAG AGA GTT GAG TCC       720
Val Asp His Lys Pro Ser Asn Thr Lys Val Asp Lys Arg Val Glu Ser
225                 230                 235                 240

AAA TAT GGT CCC CCA TGC CCA CCA TGC CCA GCA CCT GAG TTC GAG GGG       768
Lys Tyr Gly Pro Pro Cys Pro Pro Cys Pro Ala Pro Glu Phe Glu Gly
                245                 250                 255

GGA CCA TCA GTC TTC CTG TTC CCC CCA AAA CCC AAG GAC ACT CTC ATG       816
Gly Pro Ser Val Phe Leu Phe Pro Pro Lys Pro Lys Asp Thr Leu Met
            260                 265                 270

ATC TCC CGG ACC CCT GAG GTC ACG TGC GTG GTG GTG GAC GTG AGC CAG       864
Ile Ser Arg Thr Pro Glu Val Thr Cys Val Val Val Asp Val Ser Gln
        275                 280                 285
```

```
GAA GAC CCC GAG GTC CAG TTC AAC TGG TAC GTG GAT GGC GTG GAG GTG              912
Glu Asp Pro Glu Val Gln Phe Asn Trp Tyr Val Asp Gly Val Glu Val
    290                 295                 300

CAT AAT GCC AAG ACA AAG CCG CGG GAG GAG CAG TTC AAC AGC ACG TAC              960
His Asn Ala Lys Thr Lys Pro Arg Glu Glu Gln Phe Asn Ser Thr Tyr
305                 310                 315                 320

CGT GTG GTC AGC GTC CTC ACC GTC CTG CAC CAG GAC TGG CTG AAC GGC             1008
Arg Val Val Ser Val Leu Thr Val Leu His Gln Asp Trp Leu Asn Gly
                    325                 330                 335

AAG GAG TAC AAG TGC AAG GTC TCC AAC AAA GGC CTC CCG TCC TCC ATC             1056
Lys Glu Tyr Lys Cys Lys Val Ser Asn Lys Gly Leu Pro Ser Ser Ile
                340                 345                 350

GAG AAA ACC ATC TCC AAA GCC AAA GGG CAG CCC CGA GAG CCA CAG GTG             1104
Glu Lys Thr Ile Ser Lys Ala Lys Gly Gln Pro Arg Glu Pro Gln Val
            355                 360                 365

TAC ACC CTG CCC CCA TCC CAG GAG GAG ATG ACC AAG AAC CAG GTC AGC             1152
Tyr Thr Leu Pro Pro Ser Gln Glu Glu Met Thr Lys Asn Gln Val Ser
Tyr
370                 375                 380

CTG ACC TGC CTG GTC AAA GGC TTC TAC CCC AGC GAC ATC GCC GTG GAG             1200
Leu Thr Cys Leu Val Lys Gly Phe Tyr Pro Ser Asp Ile Ala Val Glu
385                 390                 395                 400

TGG GAG AGC AAT GGG CAG CCG GAG AAC AAC TAC AAG ACC ACG CCT CCC             1248
Trp Glu Ser Asn Gly Gln Pro Glu Asn Asn Tyr Lys Thr Thr Pro Pro
                405                 410                 415

GTG CTG GAC TCC GAC GGC TCC TTC TTC CTC TAC AGC AGG CTA ACC GTG             1296
Val Leu Asp Ser Asp Gly Ser Phe Phe Leu Tyr Ser Arg Leu Thr Val
                420                 425                 430

GAC AAG AGC AGG TGG CAG GAG GGG AAT GTC TTC TCA TGC TCC GTG ATG             1344
Asp Lys Ser Arg Trp Gln Glu Gly Asn Val Phe Ser Cys Ser Val Met
            435                 440                 445

CAT GAG GCT CTG CAC AAC CAC TAC ACA CAG AAG AGC CTC TCC CTG TCT             1392
His Glu Ala Leu His Asn His Tyr Thr Gln Lys Ser Leu Ser Leu Ser
        450                 455                 460

CTG GGT AAA TGA                                                             1404
Leu Gly Lys *
465
```

(2) INFORMATION FOR SEQ ID NO:12:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:12:

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Ser Val Ser Gly Gly Ser Ile
        35                  40                  45

Ser Gly Asp Tyr Tyr Trp Phe Trp Ile Arg Gln Ser Pro Gly Lys Gly
    50                  55                  60

Leu Glu Trp Ile Gly Tyr Ile Tyr Gly Ser Gly Gly Thr Asn Tyr
65                  70                  75                  80

Asn Pro Ser Leu Asn Asn Arg Val Ser Ile Ser Ile Asp Thr Ser Lys
                85                  90                  95
```

```
Asn Leu Phe Ser Leu Lys Leu Arg Ser Val Thr Ala Ala Asp Thr Ala
                100                 105                 110

Val Tyr Tyr Cys Ala Ser Asn Ile Leu Lys Tyr Leu His Trp Leu Leu
        115                 120                 125

Tyr Trp Gly Gln Gly Val Leu Val Thr Val Ser Ser Ala Ser Thr Lys
        130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Lys Thr Tyr Thr Cys Asn
        210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Glu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Gln Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
                420                 425                 430

Asp Lys Ser Arg Trp Gln Glu Gly Asn Val Phe Ser Cys Ser Val Met
                435                 440                 445

His Glu Ala Leu His Asn His Tyr Thr Gln Lys Ser Leu Ser Leu Ser
        450                 455                 460

Leu Gly Lys
465

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
```

(D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:
        (A) CHROMOSOME/SEGMENT: VH1 leader sequence (xi) SEQUENCE DESCRIPTION: SEQ ID NO:13:

ACTAAGTCGA CATGGACTGG ACCTGG                                              26

(2) INFORMATION FOR SEQ ID NO:14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:
        (A) CHROMOSOME/SEGMENT: VH2 leader sequence (xi) SEQUENCE DESCRIPTION: SEQ ID NO:14:

ACTAAGTCGA CATGGACATA CTTTGTTCCA C                                        31

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:
        (A) CHROMOSOME/SEGMENT: VH3 leader sequence (xi) SEQUENCE DESCRIPTION: SEQ ID NO:15:

ACTAAGTCGA CATGGAGTTT GGGCTGAGC                                           29

(2) INFORMATION FOR SEQ ID NO:16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:

(A) CHROMOSOME/SEGMENT: VH4 leader sequence (xi) SEQUENCE DESCRIPTION: SEQ ID NO:16:

ACTAAGTCGA CATGAAACAC CTGTGGTTCT T                              31

(2) INFORMATION FOR SEQ ID NO:17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:
        (A) CHROMOSOME/SEGMENT: VH5 leader sequence (xi) SEQUENCE DESCRIPTION: SEQ ID NO:17:

ACTAAGTCGA CATGGGGTCA ACCGCCATCC T                              31

(2) INFORMATION FOR SEQ ID NO:18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:
        (A) CHROMOSOME/SEGMENT: VH6 leader sequence (xi) SEQUENCE DESCRIPTION: SEQ ID NO:18:

ACTAAGTCGA CATGTCTGTC TCCTTCCTCA T                              31

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:
        (A) CHROMOSOME/SEGMENT: VH1 leader sequence with MluI site (xi) SEQUENCE DESCRIPTION: SEQ ID NO:19:

GGCAGCAGCY ACGCGTGCCC ACTCCGAGGT                                30

(2) INFORMATION FOR SEQ ID NO:20:

(i) SEQUENCE CHARACTERISTICS:

(A) LENGTH: 30 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:
        (A) CHROMOSOME/SEGMENT: VH2 leader sequence with MluI site (xi) SEQUENCE DESCRIPTION: SEQ ID NO:20:

GACCGTCCCG ACGCGTGTYT TGTCCCAGGT                                30

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:
        (A) CHROMOSOME/SEGMENT: VH3 leader sequence with MluI site (xi) SEQUENCE DESCRIPTION: SEQ ID NO:21:

GCTATTTTCA CGCGTGTCCA GTGTGAG                                    27

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:
        (A) CHROMOSOME/SEGMENT: VH4 leader sequence with MluI site (xi) SEQUENCE DESCRIPTION: SEQ ID NO:22:

GCGGCTCCCA CGCGTGTCCT GTCCCAG                                    27

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:

```
        (A) ORGANISM: Human or Monkey (viii) POSITION IN GENOME:
        (A) CHROMOSOME/SEGMENT: VH5 leader sequence with MluI site (xi) SEQUENCE DESCRIPTION: SEQ ID NO:23:

GGCTGTTCTC ACGCGTGTCT GTGCCGAGGT                              30

(2) INFORMATION FOR SEQ ID NO:24:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(iv) ANTI-SENSE: NO (vi) ORIGINAL SOURCE:
         (A) ORGANISM: Human or Monkey (viii) POSITION IN GENOME:
         (A) CHROMOSOME/SEGMENT: VH1,3a,5 primer with Xho I site (xi) SEQUENCE DESCRIPTION: SEQ ID NO:24:

CAGGTGCAGC TGCTCGAGTC TGG                                     23

(2) INFORMATION FOR SEQ ID NO:25:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(iv) ANTI-SENSE: NO (vi) ORIGINAL SOURCE:
         (A) ORGANISM: Human or Monkey (viii) POSITION IN GENOME:
         (A) CHROMOSOME/SEGMENT: VH2 primer with Xho I site (xi) SEQUENCE DESCRIPTION: SEQ ID NO:25:

CAGGTCAACT TACTCGAGTC TGG                                     23

(2) INFORMATION FOR SEQ ID NO:26:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(iv) ANTI-SENSE: NO (vi) ORIGINAL SOURCE:
         (A) ORGANISM: Human or Monkey (viii) POSITION IN GENOME:
         (A) CHROMOSOME/SEGMENT: VH3b primer with XhoI site (xi) SEQUENCE DESCRIPTION: SEQ ID NO:26:

GAGGTGCAGC TGCTCGAGTC TGG                                     23
```

(2) INFORMATION FOR SEQ ID NO:27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (viii) POSITION IN GENOME:
        (A) CHROMOSOME/SEGMENT: VH4 primer with XhoI site (xi) SEQUENCE DESCRIPTION: SEQ ID NO:27:

CAGGTGCAGC TGCTCGAGTC GGG                                     23

(2) INFORMATION FOR SEQ ID NO:28:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:
        (A) CHROMOSOME/SEGMENT: VH6 primer with XhoI site (xi) SEQUENCE DESCRIPTION: SEQ ID NO:28:

CAGGTACAGC TGCTCGAGTC AGG                                     23

(2) INFORMATION FOR SEQ ID NO:29:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (vi) ORIGINAL SOURCE:
        (A) ORGANISM: Human or Monkey (viii) POSITION IN GENOME:
        (A) CHROMOSOME/SEGMENT: IgG1-4 primer with NheI site (xi) SEQUENCE DESCRIPTION: SEQ ID NO:29:

GGCGGATGCG CTAGCTGAGG AGACGG                                 26

(2) INFORMATION FOR SEQ ID NO:30:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:

(A) ORGANISM: Human or Monkey (viii) POSITION IN GENOME:
            (A) CHROMOSOME/SEGMENT: kappa light chain primer with
                Bgl II site (xi) SEQUENCE DESCRIPTION: SEQ ID NO:30:

ATCACAGATC TCTCACCATG GTGTTGCAGA CCCAGGTC                               38

(2) INFORMATION FOR SEQ ID NO:31:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: NO (viii) POSITION IN GENOME:
            (A) CHROMOSOME/SEGMENT: kappa light chain primer with
                Bgl II site (xi) SEQUENCE DESCRIPTION: SEQ ID NO:31:

ATCACAGATC TCTCACCATG GRGWCCCCWG CKCAGCT                                37

(2) INFORMATION FOR SEQ ID NO:32:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: NO (vi) ORIGINAL SOURCE:
            (A) ORGANISM: Human or Monkey (viii) POSITION IN GENOME:
            (A) CHROMOSOME/SEGMENT: kappa light chain primer
                with Bgl II site (xi) SEQUENCE DESCRIPTION: SEQ ID NO:32:

ATCACAGATC TCTCACCATG GACATGAGGG TCCCCGCTCA G                           41

(2) INFORMATION FOR SEQ ID NO:33:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: NO (vi) ORIGINAL SOURCE:
            (A) ORGANISM: Human or Monkey (viii) POSITION IN GENOME:
            (A) CHROMOSOME/SEGMENT: kappa light chain primer with
                Bgl II site (xi) SEQUENCE DESCRIPTION: SEQ ID NO:33:

ATCACAGATC TCTCACCATG GACACVAGGG CCCCCACTCA G                           41

```
(2) INFORMATION FOR SEQ ID NO:34:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:
        (A) CHROMOSOME/SEGMENT: lambda light chain primer with
            Bgl II site (xi) SEQUENCE DESCRIPTION: SEQ ID NO:34:

ATCACAGATC TCTCACCATG GCCTGGGCTC TGCTGCTCC                       39

(2) INFORMATION FOR SEQ ID NO:35:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:
        (A) CHROMOSOME/SEGMENT: lambda light chain primer with
            Bgl II site (xi) SEQUENCE DESCRIPTION: SEQ ID NO:35:

ATCACAGATC TCTCACCATG GCCTGGGCTC CACTACTTC                       39

(2) INFORMATION FOR SEQ ID NO:36:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: Human or Monkey (viii) POSITION IN GENOME:
        (A) CHROMOSOME/SEGMENT: lambda light chain primer with
            Bgl II site (xi) SEQUENCE DESCRIPTION: SEQ ID NO:36:

ATCACAGATC TCTCACCATG ACCTGCTCCC CTCTCCTCC                       39

(2) INFORMATION FOR SEQ ID NO:37:

(i) SEQUENCE CHARACTERISTICS:
        (A) LENGTH: 39 base pairs
        (B) TYPE: nucleic acid
        (C) STRANDEDNESS: single
```

(D) TOPOLOGY: linear (ii) MOLECULE TYPE: DNA (genomic)

(iv) ANTI-SENSE: NO (vi) ORIGINAL SOURCE:
         (A) ORGANISM: Human or Monkey (viii) POSITION IN GENOME:
         (A) CHROMOSOME/SEGMENT: lambda light chain primer with
             Bgl II site (xi) SEQUENCE DESCRIPTION: SEQ ID NO:37:

ATCACAGATC TCTCACCATG GCCTGGACTC CTCTCTTTC                               39

(2) INFORMATION FOR SEQ ID NO:38:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (ii) MOLECULE TYPE: DNA (genomic)

(iv) ANTI-SENSE: NO (vi) ORIGINAL SOURCE:
         (A) ORGANISM: Human or Monkey (viii) POSITION IN GENOME:
         (A) CHROMOSOME/SEGMENT: lambda light chain primer with
             Bgl II site (xi) SEQUENCE DESCRIPTION: SEQ ID NO:38:

ATCACAGATC TCTCACCATG ACTTGGACCC CACTCCTC                                38

(2) INFORMATION FOR SEQ ID NO:39:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (genomic)

(iv) ANTI-SENSE: YES (vi) ORIGINAL SOURCE:
         (A) ORGANISM: Human or Monkey (viii) POSITION IN GENOME:
         (A) CHROMOSOME/SEGMENT: kappa light chain primer with Kpn1
             and BsiW1 sites (xi) SEQUENCE DESCRIPTION: SEQ ID NO:39:

CCGTTTGATT TCCAGCTTGG TACCTCCACC GAACGT                                  36

(2) INFORMATION FOR SEQ ID NO:40:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(iv) ANTI-SENSE: YES (vi) ORIGINAL SOURCE:

(A) ORGANISM: Human or Monkey (viii) POSITION IN GENOME:
          (A) CHROMOSOME/SEGMENT: kappa light chain primer with Kpn1
              and BsiW1 sites (xi) SEQUENCE DESCRIPTION: SEQ ID NO:40:

TGCAGCATCC GTACGTTTGA TTTCCAGCTT                                           30

(2) INFORMATION FOR SEQ ID NO:41:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (genomic)

(iv) ANTI-SENSE: YES (vi) ORIGINAL SOURCE:
          (A) ORGANISM: Human or Monkey (viii) POSITION IN GENOME:
          (A) CHROMOSOME/SEGMENT: lambda light chain primer with
              HindIII and Kpn1 sites (xi) SEQUENCE DESCRIPTION: SEQ ID NO:41:

ACCTAGGACG GTAAGCTTGG TACCTCCGCC                                           30

(2) INFORMATION FOR SEQ ID NO:42:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (genomic)

(iv) ANTI-SENSE: YES (vi) ORIGINAL SOURCE:
          (A) ORGANISM: Human or Monkey (viii) POSITION IN GENOME:
          (A) CHROMOSOME/SEGMENT: lambda light chain primer with Kpn 1

(xi) SEQUENCE DESCRIPTION: SEQ ID NO:42:

ACCTAGGACG GTCASSTTGG TACCTCCGCC GAACAC                                    36

(2) INFORMATION FOR SEQ ID NO:43:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(iv) ANTI-SENSE: YES (vi) ORIGINAL SOURCE:
          (A) ORGANISM: Human or Monkey (viii) POSITION IN GENOME:
          (A) CHROMOSOME/SEGMENT: lambda light chain primer with
              AvrII site (xi) SEQUENCE DESCRIPTION: SEQ ID NO:43:

```
CTTGGGCTGA CCTAGGACGG TCAGCCG                                              27

(2) INFORMATION FOR SEQ ID NO:44:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(iv) ANTI-SENSE: NO (viii) POSITION IN GENOME:
         (A) CHROMOSOME/SEGMENT: VH1 heavy chain variable region (xi) SEQUENCE DESCRIPTION: SEQ ID NO:44:

CCATGGACTG GACCTGG                                                         17

(2) INFORMATION FOR SEQ ID NO:45:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iv) ANTI-SENSE: NO (viii) POSITION IN GENOME:
         (A) CHROMOSOME/SEGMENT: VH2 heavy chain variable region (xi) SEQUENCE DESCRIPTION: SEQ ID NO:45:

ATGGACATAC TTTGTTCCAC                                                      20

(2) INFORMATION FOR SEQ ID NO:46:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iv) ANTI-SENSE: NO (viii) POSITION IN GENOME:
         (A) CHROMOSOME/SEGMENT: VH3 heavy chain variable region (xi) SEQUENCE DESCRIPTION: SEQ ID NO:46:

CCATGGAGTT TGGGCTGAGC                                                      20

(2) INFORMATION FOR SEQ ID NO:47:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iv) ANTI-SENSE: NO (viii) POSITION IN GENOME:
         (A) CHROMOSOME/SEGMENT: VH4 heavy chain variable region (xi) SEQUENCE DESCRIPTION: SEQ ID NO:47:
```

```
ATGAAACACC TGTGGTTCTT                                                    20
```

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (viii) POSITION IN GENOME:
        (A) CHROMOSOME/SEGMENT: VH5 heavy chain variable region (xi) SEQUENCE DESCRIPTION: SEQ ID NO:48:

```
ATGGGGTCAA CCGCCATCCT                                                    20
```

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (viii) POSITION IN GENOME:
        (A) CHROMOSOME/SEGMENT: VH6 heavy chain variable region (xi) SEQUENCE DESCRIPTION: SEQ ID NO:49:

```
ATGTCTGTCT CCTTCCTCAT                                                    20
```

(2) INFORMATION FOR SEQ ID NO:50:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (viii) POSITION IN GENOME:
        (A) CHROMOSOME/SEGMENT: IgM heavy chain constant region (xi) SEQUENCE DESCRIPTION: SEQ ID NO:50:

```
TTGGGGCGGA TGCACT                                                        16
```

(2) INFORMATION FOR SEQ ID NO:51:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (viii) POSITION IN GENOME:
        (A) CHROMOSOME/SEGMENT: IgG1-4 heavy chain constant region (xi) SEQUENCE DESCRIPTION: SEQ ID NO:51:

GATGGGCCCT TGGTGGA                                                    17

(2) INFORMATION FOR SEQ ID NO:52:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(viii) POSITION IN GENOME:
          (A) CHROMOSOME/SEGMENT: Kappa light chain variable region (xi) SEQUENCE DESCRIPTION: SEQ ID NO:52:

GATGACCCAG TCTCCAKCCT C                                               21

(2) INFORMATION FOR SEQ ID NO:53:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(viii) POSITION IN GENOME:
          (A) CHROMOSOME/SEGMENT: Lambda light chain variable region (xi) SEQUENCE DESCRIPTION: SEQ ID NO:53:

CTCAYTYRCT GCMCAGGGTC C                                               21

(2) INFORMATION FOR SEQ ID NO:54:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (genomic)

(iv) ANTI-SENSE: YES (viii) POSITION IN GENOME:
          (A) CHROMOSOME/SEGMENT: kappa light chain constant region (xi) SEQUENCE DESCRIPTION: SEQ ID NO:54:

AAGACAGATG GTGCAGCCA                                                  19

(2) INFORMATION FOR SEQ ID NO:55:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(iv) ANTI-SENSE: YES (viii) POSITION IN GENOME:
          (A) CHROMOSOME/SEGMENT: lambda light chain constant region (xi) SEQUENCE DESCRIPTION: SEQ ID NO:55:

GGAACAGAGT GACCGAGGGG                                                 20

(2) INFORMATION FOR SEQ ID NO:56:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(viii) POSITION IN GENOME:
        (A) CHROMOSOME/SEGMENT: PCR primer for human gamma 4
            constant region (xi) SEQUENCE DESCRIPTION: SEQ ID NO:56:

GGGGGGATCC TCATTTACCC AGAGACAGGG                                30

(2) INFORMATION FOR SEQ ID NO:57:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(viii) POSITION IN GENOME:
        (A) CHROMOSOME/SEGMENT: PCR primer for Human gamma 4
            constant region (xi) SEQUENCE DESCRIPTION: SEQ ID NO:57:

GGGGGCTAGC ACCAAGGGCC CATCCGTCTT C                              31

(2) INFORMATION FOR SEQ ID NO:58:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (genomic)

(viii) POSITION IN GENOME:
        (A) CHROMOSOME/SEGMENT: PCR mutagenesis of human gamma 4

(xi) SEQUENCE DESCRIPTION: SEQ ID NO:58:

CCGGGAGATC ATGAGAGTGT CCTTGGGTTT TGGGGGGAAC AGGAAGACTG ATGGTCCCCC   60

CTCGAACTCA GGTGCTGGGC ATGGTGGGCA TGGGGG                             96

(2) INFORMATION FOR SEQ ID NO:59:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(viii) POSITION IN GENOME:
        (A) CHROMOSOME/SEGMENT: PCR mutagenesis of human gamma 4

(xi) SEQUENCE DESCRIPTION: SEQ ID NO:59:

TCCTCAGCTA GCACCAAGGG GCCATCC                                    27

Other embodiments are within the following claims.

We claim:

1. A chimeric antibody specific to human CD4 which comprises the variable light chain sequence set forth in SEQ. ID. NO. 5 and a heavy chain sequence selected from the group consisting of the gamma-4 heavy chain sequence set forth in SEQ. ID. NO. 7, the gamma-4 heavy chain sequence set forth in SEQ. ID. NO. 9, and the gamma-4 heavy chain sequence set forth in SEQ. ID. NO. 11.

2. The chimeric anti-CD4 antibody of claim 1, wherein the gamma-4 heavy chain contained therein possesses the sequence set forth in SEQ. ID. NO. 11.

3. The chimeric anti-CD4 antibody of claim 1, wherein the gamma-4 heavy chain possesses the sequence set forth in SEQ. ID. NO. 9.

4. The anti-CD4 chimeric antibody of claim 1, wherein the gamma-4 heavy chain possesses the sequence set forth in SEQ. ID NO. 7.

5. A method of treating rheumatoid arthritis in a subject comprising administering a chimeric anti-CD4 antibody according to claim 1, in an amount effective to produce immuno suppression.

6. A method of treating rheumatoid arthritis in a subject comprising administering a chimeric anti-CD4 antibody according to claim 1, in an amount effective to produce immuno suppression.

7. A method of treating rheumatoid arthritis in a subject comprising administering a chimeric anti-CD4 antibody according to claim 3, in an amount effective to produce immuno suppression.

8. A method of treating rheumatoid arthritis in a subject comprising administering a chimeric anti-CD4 antibody according to claim 4, in an amount effective to produce immuno suppression.

9. A method of treating psoriatic arthritis in a subject comprising administering an effective amount of a chimeric anti-CD4 antibody according to claim 1, to produce immuno suppression.

10. A method of treating psoriatic arthritis in a subject comprising administering an effective amount of a chimeric anti-CD4 antibody according to claim 2, to produce immuno suppression.

11. A method of treating psoriatic arthritis in a subject comprising administering an effective amount of a chimeric anti-CD4 antibody according to claim 3, to produce immuno suppression.

12. A method of treating psoriatic arthritis in a subject comprising administering an effective amount of a chimeric anti-CD4 antibody according to claim 4, to produce immuno suppression.

13. A pharmaceutical composition which comprises a chimeric anti-CD4 antibody according to claim 1, and a pharmaceutically acceptable carrier.

14. A pharmaceutical composition which comprises a chimeric anti-CD4 antibody according to claim 2, and a pharmaceutically acceptable carrier.

15. A pharmaceutical composition which comprises a chimeric anti-CD4 antibody according to claim 3, and a pharmaceutically acceptable carrier.

16. A pharmaceutical composition which comprises a chimeric anti-CD4 antibody according to claim 4, and a pharmaceutically acceptable carrier.

* * * * *

UNITED STATES PATENT AND TRADEMARK OFFICE
CERTIFICATE OF CORRECTION

PATENT NO. : 6,136,310
DATED : October 24, 2000
INVENTOR(S) : Nabil Hanna et al.

It is certified that error appears in the above-identified patent and that said Letters Patent is hereby corrected as shown below:

Column 95,
Beginning at line 23,
Claim 6 should read as follows:
A method of treading rheumatoid arthritis in a subject coprising administering a chimeric anti-CD4 antibody according to claim 2, in an amount effective to produce immunosuppression.

Signed and Sealed this

Thirteenth Day of August, 2002

Attest:

Attesting Officer

JAMES E. ROGAN
*Director of the United States Patent and Trademark Office*